(12) United States Patent
Behzadi et al.

(10) Patent No.: US 12,193,951 B2
(45) Date of Patent: Jan. 14, 2025

(54) QUANTITATIVE ASSESSMENT OF PROSTHESIS PRESS-FIT FIXATION

(71) Applicant: Kambiz Behzadi, Pleasanton, CA (US)

(72) Inventors: Kambiz Behzadi, Pleasanton, CA (US); Michael E. Woods, Brisbane, CA (US)

(73) Assignee: Kambiz Behzadi, Pleasanton, CA (US)

( * ) Notice: Subject to any disclaimer, the term of this patent is extended or adjusted under 35 U.S.C. 154(b) by 192 days.

(21) Appl. No.: 17/821,159

(22) Filed: Aug. 19, 2022

(65) Prior Publication Data

US 2023/0128395 A1 Apr. 27, 2023

Related U.S. Application Data

(60) Division of application No. 16/374,750, filed on Apr. 4, 2019, now Pat. No. 11,534,314, which is a continuation-in-part of application No. 16/030,603, filed on Jul. 9, 2018, now Pat. No. 11,298,102, which is a continuation-in-part of application No. 15/716,533, filed on Sep. 27, 2017, now Pat. No.
(Continued)

(51) Int. Cl.
*A61F 2/46* (2006.01)
*A61B 7/02* (2006.01)
*A61F 2/34* (2006.01)
*A61B 90/00* (2016.01)

(52) U.S. Cl.
CPC ............ *A61F 2/4609* (2013.01); *A61B 7/023* (2013.01); *A61F 2/34* (2013.01); *A61F 2/468* (2013.01); *A61B 2090/064* (2016.02)

(58) Field of Classification Search
CPC ........ A61F 2002/30985; A61F 2/30942; A61F 2/46; A61F 2/4603; A61F 2/4609
See application file for complete search history.

(56) References Cited

U.S. PATENT DOCUMENTS 1,455,621 A 5/1923 Joyner
2,121,193 A 6/1938 Hanicke
(Continued)

FOREIGN PATENT DOCUMENTS

EP 1433445 A1 6/2004
WO 2004045465 A1 6/2004
(Continued)

OTHER PUBLICATIONS

International Search Report for International application No. PCT/US2017/012753, mailing date May 5, 2017.
(Continued)

*Primary Examiner* — Eric S Gibson
(74) *Attorney, Agent, or Firm* — Patent Law Offices Michael E. WOODS; Michael E. Woods

(57) ABSTRACT

A system and method for quantitatively assessing a press fit value (and provide a mechanism to evaluate optimal quantitative values) of any implant/bone interface regardless the variables involved including bone site preparation, material properties of bone and implant, implant geometry and coefficient of friction of the implant-bone interface without requiring a visual positional assessment of a depth of insertion. The following description is presented to enable one of ordinary skill in the art to make and use the invention and is provided in the context of a patent application and its requirements.

13 Claims, 27 Drawing Sheets

Related U.S. Application Data 11,109,802, which is a continuation-in-part of application No. 15/687,324, filed on Aug. 25, 2017, now Pat. No. 11,191,517, said application No. 16/030,603 is a continuation-in-part of application No. 15/284,091, filed on Oct. 3, 2016, now Pat. No. 10,441,244, said application No. 15/716,533 is a continuation-in-part of application No. 15/284,091, filed on Oct. 3, 2016, now Pat. No. 10,441,244, said application No. 15/687,324 is a continuation of application No. 15/284,091, filed on Oct. 3, 2016, now Pat. No. 10,441,244, which is a continuation-in-part of application No. 15/234,782, filed on Aug. 11, 2016, now Pat. No. 10,912,655, said application No. 15/716,533 is a continuation-in-part of application No. 15/234,782, filed on Aug. 11, 2016, now Pat. No. 10,912,655, which is a continuation-in-part of application No. 15/202,434, filed on Jul. 5, 2016, now abandoned, said application No. 15/716,533 is a continuation-in-part of application No. 15/202,434, filed on Jul. 5, 2016, now abandoned.

(60) Provisional application No. 62/651,077, filed on Mar. 31, 2018, provisional application No. 62/355,657, filed on Jun. 28, 2016, provisional application No. 62/353,024, filed on Jun. 21, 2016, provisional application No. 62/277,294, filed on Jan. 11, 2016.

(56) References Cited

U.S. PATENT DOCUMENTS

| | | | |
|---|---|---|---|
| 3,412,733 | A | 11/1968 | Ross |
| 3,818,514 | A | 6/1974 | Clark |
| 3,874,003 | A | 4/1975 | Moser et al. |
| 4,135,517 | A | 1/1979 | Reale |
| 4,301,551 | A | 11/1981 | Dore et al. |
| 4,341,206 | A | 7/1982 | Perrett et al. |
| 4,457,306 | A | 7/1984 | Borzone |
| 4,530,114 | A | 7/1985 | Tepic |
| 4,608,019 | A | 8/1986 | Kumabe et al. |
| 4,608,053 | A | 8/1986 | Keller |
| 4,712,951 | A | 12/1987 | Brown |
| 4,728,329 | A | 3/1988 | Mansat |
| 5,108,400 | A | 4/1992 | Appel et al. |
| 5,133,765 | A | 7/1992 | Cuilleron |
| 5,318,570 | A | 6/1994 | Hood et al. |
| 5,358,532 | A | 10/1994 | Evans et al. |
| 5,431,657 | A | 7/1995 | Rohr |
| 5,534,006 | A | 7/1996 | Szabo et al. |
| 5,591,164 | A | 1/1997 | Nazre et al. |
| 5,665,091 | A | 9/1997 | Noble et al. |
| 5,693,088 | A | 12/1997 | Lazarus |
| 5,702,473 | A | 12/1997 | Albrektsson et al. |
| 5,713,901 | A | 2/1998 | Tock |
| 5,769,092 | A | 6/1998 | Williamson, Jr. |
| 5,806,518 | A | 9/1998 | Mittelstadt |
| 5,849,015 | A | 12/1998 | Haywood et al. |
| 5,980,528 | A | 11/1999 | Salys |
| 6,048,365 | A | 4/2000 | Burrows et al. |
| 6,110,179 | A | 8/2000 | Flivik et al. |
| 6,146,425 | A * | 11/2000 | Hoermansdoerfer ...... A61F 2/34 623/22.31 |
| 6,161,545 | A | 12/2000 | Chow |
| 6,197,062 | B1 | 3/2001 | Fenlin |
| 6,204,592 | B1 | 3/2001 | Hur |
| 6,231,612 | B1 * | 5/2001 | Balay ........ A61F 2/34 623/22.38 |
| 6,585,771 | B1 | 7/2003 | Buttermilch et al. |
| 6,659,997 | B1 | 12/2003 | Casutt |
| 7,036,211 | B1 | 5/2006 | Panks |
| 7,645,281 | B2 | 1/2010 | Marik |
| 7,875,083 | B2 | 1/2011 | Sudmann |
| 8,167,823 | B2 | 5/2012 | Nycz et al. |
| 8,328,849 | B2 | 12/2012 | Nydegger et al. |
| 8,603,100 | B2 | 12/2013 | Muller |
| 8,876,529 | B2 | 11/2014 | Mayer et al. |
| 9,211,362 | B2 | 12/2015 | Hwang et al. |
| 9,232,968 | B2 | 1/2016 | Moumene et al. |
| 9,999,518 | B2 | 6/2018 | Mani et al. |
| 10,251,663 | B2 | 4/2019 | Behzadi |
| 10,299,930 | B2 | 5/2019 | Behzadi |
| 10,849,766 | B2 * | 12/2020 | Behzadi .................... A61F 2/34 |
| 10,864,083 | B2 * | 12/2020 | Behzadi ................. B33Y 10/00 |
| 10,905,456 | B2 | 2/2021 | Behzadi |
| 10,912,655 | B2 | 2/2021 | Behzadi et al. |
| 11,026,809 | B2 | 6/2021 | Behzadi et al. |
| 11,534,314 | B2 * | 12/2022 | Behzadi ................. A61F 2/468 |
| 11,717,310 | B2 | 8/2023 | Behzadi |
| 11,974,877 | B2 | 5/2024 | Behzadi |
| 2002/0082695 | A1 | 6/2002 | Neumann |
| 2002/0183851 | A1 | 12/2002 | Spiegelberg et al. |
| 2003/0065398 | A1 | 4/2003 | Cueille et al. |
| 2003/0229357 | A1 | 12/2003 | Dye |
| 2004/0019382 | A1 | 1/2004 | Amirouche et al. |
| 2004/0044397 | A1 | 3/2004 | Stinson |
| 2004/0097952 | A1 | 5/2004 | Sarin et al. |
| 2005/0004680 | A1 | 1/2005 | Saladino et al. |
| 2005/0012610 | A1 | 1/2005 | Liao et al. |
| 2005/0015154 | A1 | 1/2005 | Lindsey et al. |
| 2005/0101962 | A1 | 5/2005 | Schwenke et al. |
| 2005/0154398 | A1 | 7/2005 | Miniaci et al. |
| 2005/0209597 | A1 | 9/2005 | Long et al. |
| 2006/0015110 | A1 | 1/2006 | Pepper |
| 2006/0142754 | A1 | 6/2006 | Irion et al. |
| 2006/0189989 | A1 | 8/2006 | Bert |
| 2006/0247638 | A1 | 11/2006 | Trieu et al. |
| 2007/0005144 | A1 | 1/2007 | Leisinger et al. |
| 2007/0162038 | A1 | 7/2007 | Tuke |
| 2007/0219641 | A1 | 9/2007 | Dorr et al. |
| 2007/0233131 | A1 | 10/2007 | Song et al. |
| 2008/0091271 | A1 | 4/2008 | Bonitati et al. |
| 2008/0109085 | A1 | 5/2008 | Tulkis et al. |
| 2008/0234833 | A1 | 9/2008 | Bandoh et al. |
| 2008/0255560 | A1 | 10/2008 | Myers et al. |
| 2009/0112265 | A1 | 4/2009 | Hudgins et al. |
| 2009/0192626 | A1 | 7/2009 | Keefer et al. |
| 2009/0248083 | A1 | 10/2009 | Patterson et al. |
| 2009/0292321 | A1 | 11/2009 | Collette |
| 2009/0316967 | A1 | 12/2009 | Dardenne et al. |
| 2010/0023014 | A1 | 1/2010 | Romagnoli et al. |
| 2010/0100011 | A1 | 4/2010 | Roche |
| 2010/0152566 | A1 | 6/2010 | Rains et al. |
| 2010/0249796 | A1 | 9/2010 | Nycz |
| 2011/0004318 | A1 | 1/2011 | Tulkis et al. |
| 2011/0178521 | A1 | 7/2011 | Siravo et al. |
| 2011/0264009 | A1 | 10/2011 | Walter et al. |
| 2012/0172939 | A1 | 7/2012 | Pedicini |
| 2012/0209277 | A1 | 8/2012 | Leparmentier et al. |
| 2012/0215257 | A1 | 8/2012 | McDevitt et al. |
| 2012/0330429 | A1 | 12/2012 | Axelson, Jr. et al. |
| 2013/0018463 | A1 | 1/2013 | Haddad et al. |
| 2013/0204264 | A1 | 8/2013 | Mani et al. |
| 2013/0211535 | A1 | 8/2013 | Cueille |
| 2013/0218160 | A1 | 8/2013 | Bjorn et al. |
| 2013/0226189 | A1 | 8/2013 | Young |
| 2013/0261762 | A1 | 10/2013 | Kennedy |
| 2014/0012391 | A1 * | 1/2014 | Gugler ................ A61F 2/30771 623/22.33 |
| 2014/0058526 | A1 * | 2/2014 | Meridew ................. A61L 27/50 623/23.5 |
| 2014/0128986 | A1 | 5/2014 | Podolsky |
| 2014/0135773 | A1 | 5/2014 | Stein et al. |
| 2014/0135791 | A1 | 5/2014 | Nikou et al. |
| 2014/0207123 | A1 | 7/2014 | Mueller |
| 2014/0257293 | A1 * | 9/2014 | Axelson, Jr. ........ A61F 2/30771 606/79 |
| 2014/0275940 | A1 | 9/2014 | Hladio et al. |
| 2014/0303743 | A1 * | 10/2014 | Choudhury ............. A61F 2/34 623/22.24 |
| 2014/0330281 | A1 | 11/2014 | Aghazadeh |
| 2014/0363481 | A1 | 12/2014 | Pasini et al. |

(56) References Cited

U.S. PATENT DOCUMENTS

| | | | |
|---|---|---|---|
| 2014/0370462 A1 | 12/2014 | Porter et al. | |
| 2014/0371897 A1 | 12/2014 | Lin et al. | |
| 2015/0005777 A1 | 1/2015 | Ferro et al. | |
| 2015/0182350 A1 | 7/2015 | Behzadi | |
| 2015/0182351 A1 | 7/2015 | Behzadi | |
| 2015/0196343 A1 | 7/2015 | Donald et al. | |
| 2015/0201918 A1 | 7/2015 | Kumar et al. | |
| 2015/0216668 A1* | 8/2015 | Smith | B33Y 80/00 623/22.24 |
| 2015/0282856 A1 | 10/2015 | Haiat et al. | |
| 2016/0029952 A1 | 2/2016 | Hunter | |
| 2016/0058519 A1 | 3/2016 | Herr | |
| 2016/0166390 A1 | 6/2016 | Dye et al. | |
| 2016/0206430 A1 | 7/2016 | Grostefon et al. | |
| 2016/0206433 A1 | 7/2016 | Grostefon et al. | |
| 2016/0220315 A1 | 8/2016 | Falardeau et al. | |
| 2016/0310077 A1 | 10/2016 | Hunter et al. | |
| 2016/0338751 A1 | 11/2016 | Kellar et al. | |
| 2017/0056205 A1 | 3/2017 | Biegun et al. | |
| 2017/0095313 A1 | 4/2017 | van der Weide et al. | |
| 2017/0196506 A1* | 7/2017 | Behzadi | A61B 7/023 |
| 2017/0196701 A1 | 7/2017 | Behzadi et al. | |
| 2017/0196704 A1 | 7/2017 | Behzadi et al. | |
| 2017/0196705 A1 | 7/2017 | Behzadi | |
| 2017/0196706 A1 | 7/2017 | Behzadi | |
| 2017/0196707 A1 | 7/2017 | Behzadi | |
| 2017/0196708 A1 | 7/2017 | Behzadi et al. | |
| 2017/0196710 A1 | 7/2017 | Behzadi | |
| 2017/0196711 A1* | 7/2017 | Behzadi | A61B 17/320068 |
| 2017/0290666 A1* | 10/2017 | Behzadi | A61F 2/34 |
| 2017/0290667 A1* | 10/2017 | Behzadi | A61B 17/72 |
| 2017/0325972 A1 | 11/2017 | Steif | |
| 2017/0340448 A1* | 11/2017 | Behzadi | A61F 2/30771 |
| 2017/0340456 A1* | 11/2017 | Behzadi | A61F 2/4657 |
| 2017/0354505 A1 | 12/2017 | Behzadi | |
| 2018/0049891 A1 | 2/2018 | Termanini | |
| 2018/0116740 A1 | 5/2018 | Gogarty et al. | |
| 2018/0235764 A1 | 8/2018 | Moore et al. | |
| 2018/0235765 A1 | 8/2018 | Welker et al. | |
| 2018/0296364 A1 | 10/2018 | Harris et al. | |
| 2018/0325695 A1 | 11/2018 | Wozencroft | |
| 2019/0336307 A1 | 11/2019 | Sungu et al. | |
| 2020/0069279 A1* | 3/2020 | Behzadi | A61F 2/30942 |
| 2020/0069280 A1* | 3/2020 | Behzadi | A61F 2/28 |
| 2020/0205988 A1* | 7/2020 | Behzadi | A61B 17/60 |
| 2020/0261232 A1* | 8/2020 | Mistry | A61F 2/34 |
| 2020/0297499 A1* | 9/2020 | Behzadi | A61B 17/72 |
| 2022/0249236 A1 | 8/2022 | Matyas et al. | |
| 2023/0128395 A1* | 4/2023 | Behzadi | A61F 2/468 606/100 |

FOREIGN PATENT DOCUMENTS

| | | | |
|---|---|---|---|
| WO | 2007096476 A2 | 8/2007 | |
| WO | 2017029173 A1 | 2/2017 | |
| WO | 2018031752 A1 | 2/2018 | |

OTHER PUBLICATIONS

Written Opinion of the International Searching Authority for International application No. PCT/US2017/012753 with mailing date of May 5, 2017.
International Search Report for International application No. PCT/US2017/046261, mailing date Oct. 18, 2017.
Written Opinion of the International Searching Authority for International application No. PCT/US2017/046261, mailing date Oct. 18, 2017.
PCT International Search Report for International application No. PCT/US17/26417, mailed Jul. 3, 2017.
PCT Written Opinion of The International Searching Authority for International application No. PCT/US17/26417 mailed Jul. 3, 2017.
International Search Report regarding International application No. PCT/US2017/037042 dated Oct. 6, 2017.
Written Opinion of the International Searching Authority regarding International application No. PCT/US2017/037042 dated Oct. 6, 2017.
U.S. Appl. No. 17/807,268, filed Jun. 16, 2022, Kambiz Behzadi et al.
U.S. Appl. No. 17/823,955, filed Aug. 31, 2022, Kambiz Behzadi.
U.S. Appl. No. 18/656,225, filed May 6, 2024, Kambiz Behzadi.
U.S. Appl. No. 18/656,291, filed May 6, 2024, Kambiz Behzadi.
U.S. Appl. No. 62/277,294, filed Jan. 11, 2016, Kambiz Behzadi.
U.S. Appl. No. 62/353,024, filed Jun. 21, 2016, Kambiz Behzadi.
U.S. Appl. No. 62/355,657, filed Jun. 28, 2016, Kambiz Behzadi.
U.S. Appl. No. 62/373,515, filed Aug. 11, 2016, Kambiz Behzadi.
U.S. Appl. No. 62/651,077, filed Mar. 31, 2018, Kambiz Behzadi.
U.S. Appl. No. 62/742,851, filed Oct. 8, 2018, Kambiz Behzadi.
U.S. Appl. No. 62/743,042, filed Oct. 9, 2018, Kambiz Behzadi et al.
U.S. Appl. No. 15/202,434, filed Jul. 5, 2016, Kambiz Behzadi.
U.S. Appl. No. 15/234,782, filed Aug. 11, 2016, Kambiz Behzadi et al.
U.S. Appl. No. 15/234,880, filed Aug. 11, 2016, Kambiz Behzadi et al.
U.S. Appl. No. 15/235,032, filed Aug. 11, 2016, Kambiz Behzadi et al.
U.S. Appl. No. 15/235,053, filed Aug. 11, 2016, Kambiz Behzadi.
U.S. Appl. No. 15/284,091, filed Oct. 3, 2016, Kambiz Behzadi.
U.S. Appl. No. 15/362,675, filed Nov. 28, 2016, Kambiz Behzadi.
U.S. Appl. No. 15/396,785, filed Jan. 2, 2017, Kambiz Behzadi et al.
U.S. Appl. No. 15/398,996, filed Jan. 5, 2017, Kambiz Behzadi.
U.S. Appl. No. 15/453,219, filed Mar. 8, 2017, Kambiz Behzadi.
U.S. Appl. No. 15/592,229, filed May 11, 2017, Kambiz Behzadi.
U.S. Appl. No. 15/687,324, filed Aug. 25, 2017, Kambiz Behzadi.
U.S. Appl. No. 15/716,529, filed Sep. 27, 2017, Kambiz Behzadi et al.
U.S. Appl. No. 15/716,533, filed Sep. 27, 2017, Kambiz Behzadi.
U.S. Appl. No. 16/030,603, filed Jul. 9, 2018, Kambiz Behzadi.
U.S. Appl. No. 16/030,824, filed Jul. 9, 2018, Kambiz Behzadi.
U.S. Appl. No. 16/154,033, filed Oct. 8, 2018, Kambiz Behzadi et al.
U.S. Appl. No. 16/276,639, filed Feb. 15, 2019, Kambiz Behzadi.
U.S. Appl. No. 16/278,085, filed Feb. 16, 2019, Kambiz Behzadi.
U.S. Appl. No. 16/278,668, filed Feb. 18, 2019, Kambiz Behzadi.
U.S. Appl. No. 16/374,750, filed Apr. 4, 2019, Kambiz Behzadi et al.
U.S. Appl. No. 16/375,736, filed Apr. 4, 2019, Kambiz Behzadi et al.
U.S. Appl. No. 16/571,180, filed Sep. 15, 2019, Kambiz Behzadi.
U.S. Appl. No. 16/586,960, filed Sep. 28, 2019, Kambiz Behzadi.
U.S. Appl. No. 16/589,099, filed Sep. 30, 2019, Kambiz Behzadi.
U.S. Appl. No. 16/595,341, filed Oct. 7, 2019, Kambiz Behzadi.
U.S. Appl. No. 16/596,410, filed Oct. 8, 2019, Kambiz Behzadi et al.
U.S. Appl. No. 16/819,092, filed Mar. 14, 2020, Kambiz Behzadi et al.
U.S. Appl. No. 16/842,415, filed Apr. 7, 2020, Kambiz Behzadi.
U.S. Appl. No. 16/945,908, filed Aug. 2, 2020, Kambiz Behzadi et al.
U.S. Appl. No. 17/010,769, filed Sep. 2, 2020, Kambiz Behzadi et al.
U.S. Appl. No. 17/164,780, filed Feb. 1, 2021, Kambiz Behzadi.
U.S. Appl. No. 17/238,148, filed Apr. 22, 2021, Kambiz Behzadi.
U.S. Appl. No. 17/446,985, filed Sep. 7, 2021, Kambiz Behzadi.
U.S. Appl. No. 17/449,245, filed Sep. 28, 2021, Kambiz Behzadi.
U.S. Appl. No. 17/457,761, filed Dec. 6, 2021, Kambiz Behzadi.
U.S. Appl. No. 17/586,359, filed Jan. 27, 2022, Kambiz Behzadi.
U.S. Appl. No. 17/587,389, filed Jan. 28, 2022, Kambiz Behzadi.
U.S. Appl. No. 17/587,835, filed Jan. 28, 2022, Kambiz Behzadi et al.
U.S. Appl. No. 17/588,793, filed Jan. 31, 2022, Kambiz Behzadi.
U.S. Appl. No. 17/807,232, filed Jun. 16, 2022, Kambiz Behzadi et al.
U.S. Appl. No. 17/807,328, filed Jun. 16, 2022, Kambiz Behzadi.

(56) References Cited

OTHER PUBLICATIONS

U.S. Appl. No. 17/814,807, filed Jul. 25, 2022, Kambiz Behzadi et al.
U.S. Appl. No. 18/175,534, filed Feb. 27, 2023, Kambiz Behzadi et al.
U.S. Appl. No. 18/175,912, filed Feb. 28, 2023, Kambiz Behzadi et al.
U.S. Appl. No. 18/236,335, filed Aug. 21, 2023, Kambiz Behzadi et al.

* cited by examiner

QUANTITATIVE ASSESSMENT OF PROSTHESIS PRESS-FIT FIXATION

CROSS REFERENCE TO RELATED APPLICATIONS

This Application is a Division of application Ser. No. 16/374,750 filed on Apr. 4, 2019; Application Ser. No. 16/374,750 is a Continuation-in-part of application Ser. No. 16/030,603 filed on Jul. 9, 2018; Application Ser. No. 16/030,603 claims the benefit of U.S. Provisional Application 62/651,077 filed on Mar. 31, 2018; Application Ser. No. 16/030,603 is a Continuation-in-part of application Ser. No. 15/716,533 filed on Sep. 27, 2017; Application Ser. No. 15/716,533 is a Continuation-in-part of application Ser. No. 15/687,324 filed on Aug. 25, 2017; Application Ser. No. 15/687,324 is a Continuation of application Ser. No. 15/284,091 filed on Oct. 3, 2016; Application Ser. No. 15/284,091 is a Continuation-in-part of application Ser. No. 15/234,782 filed on Aug. 11, 2016; Application Ser. No. 15/234,782 is a Continuation-in-part of application Ser. No. 15/202,434 filed on Jul. 5, 2016; Application Ser. No. 15/202,434 claims the benefit of U.S. Provisional Application 62/277,294 filed on Jan. 11, 2016; Application Ser. No. 15/234,782 claims the benefit of U.S. Provisional Application 62/355,657 filed on Jun. 28, 2016; Application Ser. No. 15/234,782 claims the benefit of U.S. Provisional Application 62/353,024 filed on Jun. 21, 2016; and all of these identified applications, including parent applications, are hereby expressly incorporated by reference thereto in their entireties for all purposes.

FIELD OF THE INVENTION

The present invention relates generally to assessing a quality of a press-fit installation of a structure, and more specifically, but not exclusively, to quantitative assessment of prosthesis press-fit fixation into a bone cavity, for example, assessment of press-fit fixation of an acetabular cup into a prepared (e.g., relatively under-reamed acetabulum) bone cavity.

BACKGROUND OF THE INVENTION

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also be inventions.

Initial stability of metal backed acetabular components is an important factor in an ultimate success of cement-less hip replacement surgery. The press fit technique, which involves impaction of an oversized (relative to a prepared cavity in an acetabulum) porous coated acetabular cup into an undersized cavity (relative to the prosthesis to be installed) of bone produces primary stability through cavity deformation and frictional forces, and has shown excellent long term results. This press fit technique avoids use of screw fixation associated with risk of neurovascular injury, fretting and metallosis, and egress of particulate debris and osteolysis.

However, it has been difficult to assess a primary implant stability due to complex nature of bone-implant interface, or to evaluate an optimal press fit fixation. The initial interaction of the implant with bone is due the circumferential surface interference at the aperture transitioning to compression of the cavity with deeper insertion. A compromise exists between seating the cup enough to get sufficient primary stability and avoiding fracture of bone. There is no quantitative method in current clinical practice to assess the primary stability of the implant, with surgeons relying solely on their qualitative proprioceptive senses (tactile, auditory, and visual) to determine point of optimal press fit fixation.

Four factors associated with difficulty obtaining optimal press fit fixation: i) no current method exists to gauge the resulting stress field in bone during the impaction of an oversized implant; ii) the material properties of bone (bone density) vary significantly based on age and sex of the patient, and are unknown to the surgeon; iii) current mallet based techniques for impaction do not allow surgeons to control (quantify and increment) the magnitude of force using in installation; and iv) surgeons are charged with the difficult task of: a) applying and modulating magnitude of force; b) deciding when to stop application of force; and c) assessing a quality of press fit fixation all simultaneously in their "mind's eye" during the process of impaction.

A significance of this problem on patients, medical practice and economy is great. Although Total Hip Replacement (THR) is widely recognized as a successful operation, 3 to 25% of operations fail requiring revision surgery. Aseptic loosening of press fit THR components is one of the most common causes of failure at 50% to 90% and closely associated with insufficient initial fixation. Inadequate stabilization may lead to late presentation of aseptic loosening due to formation of fibrous tissue and over stuffing the prosthesis may lead to occult and/or frank peri-prosthetic fractures. The cost of poor initial press fit fixation resulting from (loosening, occult fractures, subsidence, fretting, metallosis, and infections) maybe under reported however estimated to be in tens of billions of dollars. Over 400,000 total hip replacements are done in US every year, over 80% of which are done by surgeons who do less than ten per year. The limitations of this procedure produce frustration and anxiety for surgeons, physical and emotional pain for patients, at great costs to society.

Initial implant fixation can be measured by pullout, lever out, and torsional test in vitro; however, these methods have minimal utility in a clinical setting in that they are destructive. Vibration analysis, where secure and loose implants can be distinguished by the differing frequency responses of the implant bone interface, has been successfully employed in evaluating fixation of dental implants however, this technology has not been easily transferable to THR surgery, and currently has no clinical utility.

In clinical practice, surgeons err on the side of not overstuffing the prosthesis which leads to a smaller under ream (or line to line ream) and screw fixation with attendant risks.

Finally, several visual tracking methods (Computer Navigation, Fluoroscopy, MAKO Robotics) are utilized to assess the depth of cup insertion during impaction in order to guide application of force; however, these techniques, from and engineering perspective, are considered to be open loop, where the feedback response to the surgeon is not a force (sensory) response, and therefore does not provide any information about the stress response of the cavity.

A system and method is needed to quantitatively assess a press fit value (and provide a mechanism to evaluate optimal quantitative values) of any implant/bone interface regardless the variables involved including bone site preparation, material properties of bone and implant, implant geometry and coefficient of friction of the implant-bone interface without requiring a visual positional assessment of a depth of insertion.

BRIEF SUMMARY OF THE INVENTION

Disclosed is a system and method for quantitatively assessing a press fit value (and provide a mechanism to evaluate optimal quantitative values) of any implant/bone interface regardless the variables involved including bone site preparation, material properties of bone and implant, implant geometry and coefficient of friction of the implant-bone interface without requiring a visual positional assessment of a depth of insertion.

The following summary of the invention is provided to facilitate an understanding of some of the technical features related to installation of an acetabular cup prosthesis into a relatively undersized prepared cavity in an acetabulum, and is not intended to be a full description of the present invention. A full appreciation of the various aspects of the invention can be gained by taking the entire specification, claims, drawings, and abstract as a whole. The present invention is applicable to other press fit fixation systems, including installation of different prostheses into different locations, and installation of other structures into an elastic substrate.

Some embodiments of the proposed technology may enable a standardization of: a) application of force; and b) assessment of quality of fixation in joint replacement surgery, such that surgeons of all walks of life, whether they perform five or 500 hip replacements per year, will produce consistently superior/optimum/perfect results with respect to press fit fixation of implants in bone.

From the surgeon perspective this standardization process will level the playing field between the more and less experienced surgeons, leading to less stress and anxiety for the surgeons affecting their mental wellness. From the patient perspective there will be a decrease in the number of complications and ER admissions leading to decrease in morbidity and mortality. From an economic perspective there will be a significant cost savings for the government and insurance companies due to a decrease in the number of readmissions and revision surgery's, particularly since revision surgery in orthopedics accounts for up to 30% of a 50-billion-dollar industry.

To address this deficiency, some embodiments and related applications have considered a novel means of accessing and processing various force responses of bone (Invasive Sensing Mechanism) and propose that this mechanism can guide application of force to the bone cavity, to obtain optimal press fit technologically without reliance on surgeon's proprioception. There are several possible outcomes of this proposal, if validated, including that it may make joint replacement surgery a significantly safer operation leading to less morbidity and complications, readmissions, and revision surgery; resulting in great benefits to patients, surgeons and society in general.

An embodiment of the present invention may include a series of operations for installing a prosthesis into a relatively undersized cavity prepared in a portion of bone, including communicating, using an installation agency, a quantized applied force to a prosthesis being press-fit into the cavity; monitoring a rigidity metric and an elasticity metric of the prosthesis with respect to the cavity (some embodiments do this in real-time or near real-time without requiring imaging or position-determination technology); further processing responsive to the rigidity and elasticity metrics, including continuing to install the prosthesis at present level of applied force while monitoring the metrics when the metrics indicate that installation change is acceptable and a risk of fracture remains at an acceptable level, increasing the applied force and continuing applying the installation agency while monitoring the metrics when the metrics indicate that installation change is minimal and a risk of fracture remains at an acceptable level, or suspending operation of the installation agency when the metrics indicate that installation change is minimal when a risk of fracture increases to an unacceptable level. Some embodiments may determine rigidity/elasticity from position, or vibration spectrum in air (sound) or bone. In some embodiments, while rigidity and elasticity may be determined in several different ways, some of which are disclosed herein, some implementations may determine a quantitative assessment responsive to evaluations of both responsive rigidity and elasticity factors during controlled operation of an insertion agency communicating an application force to a prosthesis (best fixation short of fracture—BFSF). BFSF may be related to one or both of these rigidity and elasticity factors.

An apparatus for insertion of a prosthesis into a cavity formed in a portion of bone, the prosthesis relatively oversized with respect to the cavity, including an insertion device providing an insertion agency to the prosthesis, the insertion agency operating over a period, the period including an initial prosthesis insertion act with the insertion device and a subsequent prosthesis insertion act with the insertion device; and a system physically coupled to the insertion device configured to provide a parametric evaluation of an extractive force of an interface between the prosthesis and the cavity during the period, the parametric evaluation including an evaluation of a set of factors of the prosthesis with respect to the cavity, the set of factors including one or more of a rigidity factor, an elasticity factor, and a combination of the rigidity factor and the elasticity factor.

A method for an insertion of an implant into a cavity in a portion of bone, the cavity relatively undersized with respect to the implant, including a) providing, using a device, an implant insertion agency to the implant to transition the implant toward a deepen insertion into the cavity; and b) predicting, responsive to the implant insertion agency, a press-fit fixation of the implant at an interface between the implant and the cavity during the providing of the implant insertion agency.

An impact control method for installing an implant into a cavity in a portion of bone, the cavity relatively undersized with respect to the implant, including a) imparting a first initial known force to the implant; b) imparting a first subsequent known force to the implant, the first subsequent known force about equal to the first initial force; c) measuring, for each the imparted known force, an Xth number measured impact force; d) comparing the Xth measured impact force to the Xth−1 measured impact force against a predetermined threshold for a threshold test; and e) repeating steps b)-d) as long as the threshold test is negative.

A method for an automated installation of an implant into a cavity in a portion of bone, including a) initiating an application of an installation agency to the implant, the installation agency including an energy communicated to the implant moving the implant deeper into the cavity in response thereto; b) recording a set of measured response forces responsive to the installation agency; c) continuing applying and recording until a difference in successive measured responses is within a predetermined threshold to estimate no significant displacement of the implant at the energy as the implant is installed into the cavity; d) increasing the energy; e) repeating steps b)-c) until a plateau of the set of the measured response forces; and f) terminating steps b)-e) when a steady-state is detected.

A method for insertion of a prosthesis into a cavity formed in a portion of bone, the prosthesis relatively oversized with respect to the cavity, including a) applying an insertion agency to the prosthesis, the insertion agency operating over a period, the period including an initial prosthesis insertion act with the insertion device and a subsequent prosthesis insertion act with the insertion device; and b) providing a parametric evaluation of an extractive force of an interface between the prosthesis and the cavity during the period, the parametric evaluation including an evaluation of a set of factors of the prosthesis with respect to the cavity, the set of factors including one or more of a rigidity factor, an elasticity factor, and a combination of the rigidity factor and the elasticity factor.

An apparatus for installing a prosthesis into a relatively undersized prepared cavity in a portion of a bone, including a force applicator operating an insertion agency for installing the prosthesis into the cavity; a force transfer structure, coupled to the force applicator and to the prosthesis, for conveying an application force F1 to the prosthesis, the application force F1 derived from the insertion agency; a force sensing system determining a force response of the prosthesis at an interface of the prosthesis and the cavity, the force response responsive to the application force F1; and a controller, coupled to force applicator and to the force sensing system, the controller setting an operational parameter for the insertion agency, the operational parameter establishing the application force F1, the controller responsive to the force response to establish a set of parameters including one or more of a rigidity metric, an elasticity metric, and combinations thereof.

A method for installing a prosthesis into a relatively undersized cavity prepared in a portion of bone, including a) communicating an application force F1 to the prosthesis; b) monitoring a rigidity factor and an elasticity factor of the prosthesis within the cavity during application of the application force F1; c) repeating a)-b) until the rigidity factor meets a first predetermined goal; d) increasing, when the rigidity factor meets the predetermined goal, the application force F1; e) repeating a)-d) until the elasticity factor meets a second predetermined goal; and f) suspending a) when the elasticity factor meets the first goal and the rigidity factor meets the second goal.

An acetabular cup for a prepared cavity in a portion of bone, including a generally hemispherical exterior shell portion defining a generally hemispherical interior cavity; and a snubbed polar apex portion of the generally hemispherical exterior shell portion without degradation of the generally hemispherical interior cavity producing a polar gap within the prepared cavity when fully seated.

An implant for a prepared cavity in a portion of bone, including an exterior shell portion having an interior cavity; and a snubbed polar apex portion of the exterior shell portion without degradation of the interior cavity producing a polar gap within the prepared cavity when fully seated.

An apparatus for insertion of a prosthesis into a cavity formed in a portion of bone, the prosthesis relatively oversized with respect to the cavity, including means for applying an insertion agency to the prosthesis, the insertion agency operating over a period, the period including an initial prosthesis insertion act with the insertion device and a subsequent prosthesis insertion act with the insertion device; and means, physically coupled to the insertion device, for determining a parametric evaluation of an extractive force of an interface between the prosthesis and the cavity during the period, the parametric evaluation including an evaluation of a set of factors of the prosthesis with respect to the cavity, the set of factors including one or more of a rigidity factor, an elasticity factor, and a combination of the rigidity factor and the elasticity factor.

An acetabular cup for an installation into an irregularly-profiled cavity in a portion of bone, the installation having a desired orientation profile for the acetabular cup, including; an irregularly-profiled exterior shell portion defining a generally hemispherical interior cavity, said irregularly-profiled exterior shell portion complementary to the irregularly-profiled cavity; wherein said irregularly-profiled exterior shell portion is configured for a press fit fixation into the irregularly-profiled cavity; and wherein a composite of the irregularly-profiled cavity and said irregularly-profiled exterior shell cooperatively define a unique orientation key producing the desired orientation profile for the acetabular cup when installed into the irregularly-profiled cavity.

A kit for an installation of an implant into an irregularly-profiled cavity in a portion of bone, the kit including: a preoperatively-determined orientation for the implant; a body of the implant defining a body portion configured for fixation within the prepared cavity, said body portion including a body keying structure; and a bone-preparation tool configured to produce the irregularly-profiled cavity in the portion of bone, the cavity having an interior wall surface defining a cavity portion configured for receiving said body portion, said cavity portion including a cavity keying structure complementary to said body keying structure; wherein a composite of said keying structures cooperatively produce said preoperatively-determined orientation by defining a unique key imparting said preoperatively-determined orientation when said body portion is fixated within said cavity portion.

Any of the embodiments described herein may be used alone or together with one another in any combination. Inventions encompassed within this specification may also include embodiments that are only partially mentioned or alluded to or are not mentioned or alluded to at all in this brief summary or in the abstract. Although various embodiments of the invention may have been motivated by various deficiencies with the prior art, which may be discussed or alluded to in one or more places in the specification, the embodiments of the invention do not necessarily address any of these deficiencies. In other words, different embodiments of the invention may address different deficiencies that may be discussed in the specification. Some embodiments may only partially address some deficiencies or just one deficiency that may be discussed in the specification, and some embodiments may not address any of these deficiencies.

Other features, benefits, and advantages of the present invention will be apparent upon a review of the present disclosure, including the specification, drawings, and claims.

BRIEF DESCRIPTION OF THE DRAWINGS

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

FIG. 11 illustrates a comparison of F5 to F1;

FIG. 12 illustrates a comparison of ΔF5 to a predetermined threshold (e.g., 0.0);

FIG. 13 illustrates a comparison of F2 to F1;

FIG. 14 illustrates a comparison of ΔF2 to a predetermined threshold (e.g., 0.0);

FIG. 28 illustrates a top view of a circular acetabular cavity opening;

FIG. 29 illustrates a top view of a regular polygonal acetabular cavity opening;

FIG. 30 illustrates a top view of an irregular acetabular cavity opening;

DETAILED DESCRIPTION OF THE INVENTION

Figure 1:
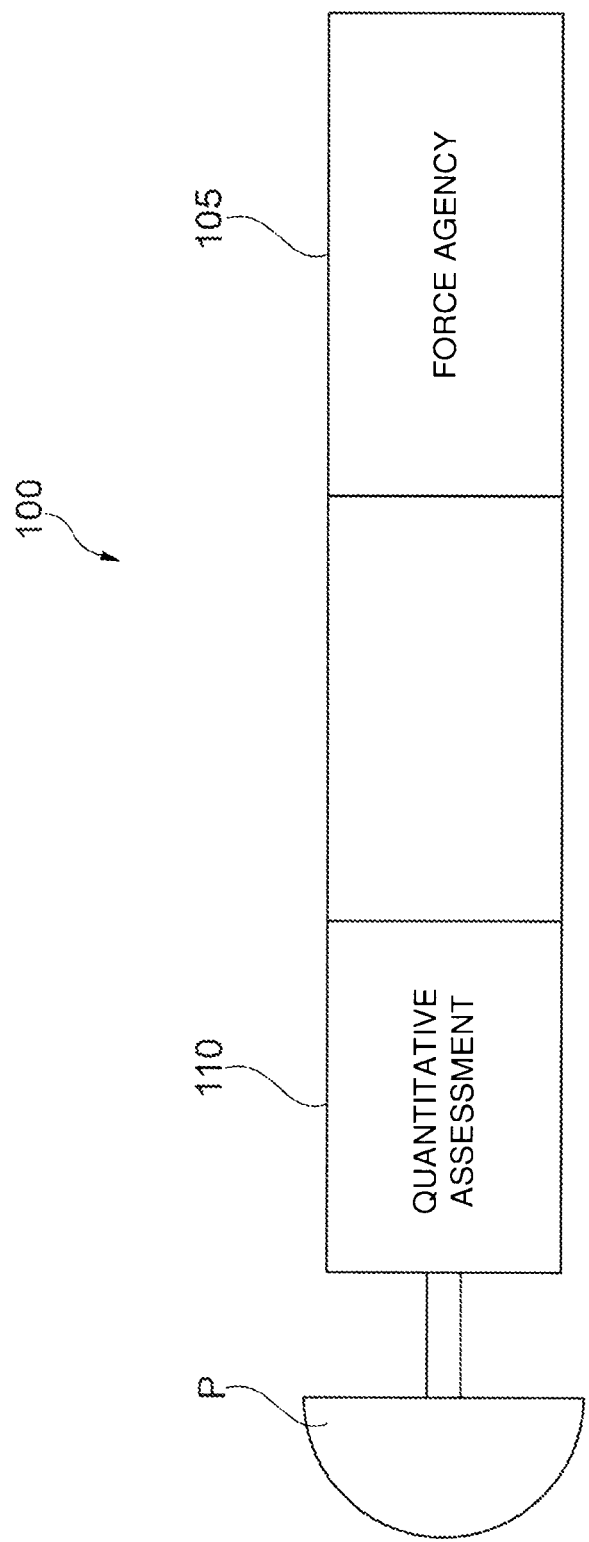
FIG. 1 illustrates an smart tool for prosthesis installation.

Embodiments of the present invention provide a system and method for quantitatively assessing a press fit value (and provide a mechanism to evaluate optimal quantitative values) of any implant/bone interface regardless the variables involved including bone site preparation, material properties of bone and implant, implant geometry and coefficient of friction of the implant-bone interface without requiring a visual positional assessment of a depth of insertion. The following description is presented to enable one of ordinary skill in the art to make and use the invention and is provided in the context of a patent application and its requirements.

Various modifications to the preferred embodiment and the generic principles and features described herein will be readily apparent to those skilled in the art. Thus, the present invention is not intended to be limited to the embodiment shown but is to be accorded the widest scope consistent with the principles and features described herein.

Definitions

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

The following definitions apply to some of the aspects described with respect to some embodiments of the invention. These definitions may likewise be expanded upon herein.

As used herein, the term "or" includes "and/or" and the term "and/or" includes any and all combinations of one or more of the associated listed items. Expressions such as "at least one of," when preceding a list of elements, modify the entire list of elements and do not modify the individual elements of the list.

As used herein, the singular terms "a," "an," and "the" include plural referents unless the context clearly dictates otherwise. Thus, for example, reference to an object can include multiple objects unless the context clearly dictates otherwise.

Also, as used in the description herein and throughout the claims that follow, the meaning of "in" includes "in" and "on" unless the context clearly dictates otherwise. It will be understood that when an element is referred to as being "on" another element, it can be directly on the other element or intervening elements may be present therebetween. In contrast, when an element is referred to as being "directly on" another element, there are no intervening elements present.

As used herein, the term "set" refers to a collection of one or more objects. Thus, for example, a set of objects can include a single object or multiple objects. Objects of a set also can be referred to as members of the set. Objects of a set can be the same or different. In some instances, objects of a set can share one or more common properties.

As used herein, the term "adjacent" refers to being near or adjoining. Adjacent objects can be spaced apart from one another or can be in actual or direct contact with one another. In some instances, adjacent objects can be coupled to one another or can be formed integrally with one another.

As used herein, the terms "connect," "connected," and "connecting" refer to a direct attachment or link. Connected objects have no or no substantial intermediary object or set of objects, as the context indicates.

As used herein, the terms "couple," "coupled," and "coupling" refer to an operational connection or linking. Coupled objects can be directly connected to one another or can be indirectly connected to one another, such as via an intermediary set of objects.

The use of the term "about" applies to all numeric values, whether or not explicitly indicated. This term generally refers to a range of numbers that one of ordinary skill in the art would consider as a reasonable amount of deviation to the recited numeric values (i.e., having the equivalent function or result). For example, this term can be construed as including a deviation of ±10 percent of the given numeric value provided such a deviation does not alter the end function or result of the value. Therefore, a value of about 1% can be construed to be a range from 0.9% to 1.1%.

As used herein, the terms "substantially" and "substantial" refer to a considerable degree or extent. When used in conjunction with an event or circumstance, the terms can refer to instances in which the event or circumstance occurs precisely as well as instances in which the event or circumstance occurs to a close approximation, such as accounting for typical tolerance levels or variability of the embodiments described herein.

As used herein, the terms "optional" and "optionally" mean that the subsequently described event or circumstance may or may not occur and that the description includes instances where the event or circumstance occurs and instances in which it does not.

As used herein, the term "bone" means rigid connective tissue that constitute part of a vertebral skeleton, including mineralized osseous tissue, particularly in the context of a living patient undergoing a prosthesis implant into a portion of cortical bone. A living patient, and a surgeon for the patient, both have significant interests in reducing attendant risks of conventional implanting techniques including fracturing/shattering the bone and improper installation and positioning of the prosthesis within the framework of the patient's skeletal system and operation.

As used herein, the term "size" refers to a characteristic dimension of an object. Thus, for example, a size of an object that is spherical can refer to a diameter of the object. In the case of an object that is non-spherical, a size of the non-spherical object can refer to a diameter of a corresponding spherical object, where the corresponding spherical object exhibits or has a particular set of derivable or measurable properties that are substantially the same as those of the non-spherical object. Thus, for example, a size of a non-spherical object can refer to a diameter of a corresponding spherical object that exhibits light scattering or other properties that are substantially the same as those of the non-spherical object. Alternatively, or in conjunction, a size of a non-spherical object can refer to an average of various orthogonal dimensions of the object. Thus, for example, a size of an object that is a spheroidal can refer to an average of a major axis and a minor axis of the object. When referring to a set of objects as having a particular size, it is contemplated that the objects can have a distribution of sizes around the particular size. Thus, as used herein, a size of a set of objects can refer to a typical size of a distribution of sizes, such as an average size, a median size, or a peak size.

As used herein, mallet or hammer refers to an orthopedic device made of stainless steel or other dense material having a weight generally a carpenter's hammer and a stonemason's lump hammer.

As used herein, an impact force for impacting an acetabular component (e.g., an acetabular cup prosthesis) includes forces from striking an impact rod multiple times with the orthopedic device that are generally similar to the forces that may be used to drive a three inch nail into a piece of lumber using the carpenter's hammer by striking the nail approximately a half-dozen times to completely seat the nail. Without limiting the preceding definition, a representative value in some instances includes a force of approximately 10 lbs./square inch.

As used herein, the term "realtime" sensing means sensing relevant parameters (e.g., force, acceleration, vibration, acoustic, and the like) during processing (e.g., installation, reaming, cutting) without stopping or suspending processing for visual evaluation of insertion depth of a prosthesis into a prepared cavity.

The following description relates to improvements in a wide-range of prostheses installations into live bones of patients of surgeons. The following discussion focuses primarily on total hip replacement (THR) in which an acetabular cup prosthesis is installed into the pelvis of the patient. This cup is complementary to a ball and stem (i.e., a femoral prosthesis) installed into an end of a femur engaging the acetabulum undergoing repair.

Embodiments of the present invention may include one of more solutions to the above problems. U.S. Pat. No. 9,168,154, expressly incorporated by reference thereto in its entirety for all purposes, includes a description of several embodiments, sometimes referred to herein as a BMD3 device, some of which illustrate a principle for breaking down large forces associated with the discrete blows of a mallet into a series of small taps, which in turn perform similarly in a stepwise fashion while being more efficient and safer. The BMD3 device produces the same displacement of the implant without the need for the large forces from the repeated impacts from the mallet. The BMD3 device may allow modulation of force required for cup insertion based on bone density, cup geometry, and surface roughness. Further, a use of the BMD3 device may result in the acetabulum experiencing less stress and deformation and the implant may experience a significantly smoother sinking pattern into the acetabulum during installation. Some embodiments of the BMD3 device may provide a superior approach to these problems, however, described herein are two problems that can be approached separately and with more basic methods as an alternative to, or in addition to, a BMD3 device. An issue of undesirable torques and moment arms is primarily related to the primitive method currently used by surgeons, which involves manually banging the mallet on the impaction plate. The amount of force utilized in this process is also non-standardized and somewhat out of control.

With respect to the impaction plate and undesirable torques, an embodiment of the present invention may include a simple mechanical solution as an alternative to some BMD3 devices, which can be utilized by the surgeon's hand or by a robotic machine. A direction of the impact may be directed or focused by any number of standard techniques (e.g., A-frame, C-arm or navigation system). Elsewhere described herein is a refinement of this process by considering directionality in the reaming process, in contrast to only considering it just prior to impaction. First, we propose to eliminate the undesirable torques by delivering the impacts by a sledgehammer device or a (hollow cylindrical mass) that travels over a stainless rod.

As noted in the background, the surgeon prepares the surface of the hipbone which includes attachment of the acetabular prosthesis to the pelvis. Conventionally, this attachment includes a manual implantation in which a mallet is used to strike a tamp that contacts some part of the acetabular prosthesis. Repeatedly striking the tamp drives the acetabular prosthesis into the acetabulum. Irrespective of whether current tools of computer navigation, fluoroscopy, robotics (and other intra-operative measuring tools) have been used, it is extremely unlikely that the acetabular prosthesis will be in the correct orientation once it has been seated to the proper depth by the series of hammer strikes. After manual implantation in this way, the surgeon then may apply a series of adjusting strikes around a perimeter of the acetabular prosthesis to attempt to adjust to the desired orientation. Currently such post-impaction result is accepted as many surgeons believe that post-impaction adjustment creates an unpredictable and unreliable change which does not therefore warrant any attempts for post-impaction adjustment.

In most cases, any and all surgeons including an inexperienced surgeon may not be able to achieve the desired orientation of the acetabular prosthesis in the pelvis by conventional solutions due to unpredictability of the orientation changes responsive to these adjusting strikes. As noted above, it is most common for any surgeon to avoid post-impaction adjustment as most surgeons understand that they do not have a reliable system or method for improving any particular orientation and could easily introduce more/greater error. The computer navigation systems, fluoroscopy, and other measuring tools are able to provide the surgeon with information about the current orientation of the prosthesis during an operation and after the prosthesis has been installed and its deviation from the desired orientation, but the navigation systems (and others) do not protect against torsional forces created by the implanting/positioning strikes. The prosthesis will find its own position in the acetabulum based on the axial and torsional forces created by the blows of the mallet. Even those navigation systems used with robotic systems (e.g., MAKO) that attempt to secure an implant in the desired orientation prior to impaction are not guaranteed to result in the installation of the implant at the desired orientation because the actual implanting forces are applied by a surgeon swinging a mallet to manually strike the tamp.

A Behzadi Medical Device (BMD) is herein described and enabled that eliminates this crude method (i.e., mallet, tamp, and surgeon-applied mechanical implanting force) of the prosthesis (e.g., the acetabular cup). A surgeon using the BMD is able to insert the prosthesis exactly where desired with proper force, finesse, and accuracy. Depending upon implementation details, the installation includes insertion of the prosthesis into patient bone, within a desired threshold of metrics for insertion depth and location) and may also include, when appropriate and/or desired, positioning at a desired orientation with the desired threshold further including metrics for insertion orientation). The use of the BMD reduces risks of fracturing and/or shattering the bone receiving the prosthesis and allows for rapid, efficient, and accurate (atraumatic) installation of the prosthesis. The BMD provides a viable interface for computer navigation assistance (also useable with all intraoperative measuring tools including fluoroscopy) during the installation as a lighter more responsive touch may be used.

The BMD encompasses many different embodiments for installation and/or positioning of a prosthesis and may be adapted for a wide range of prostheses in addition to installation and/or positioning of an acetabular prosthesis during THR, including examples of a device, which may be automated, for production and/or communication of an installation agency to a prosthesis.

FIG. 1 illustrates a smart tool 100 for prosthesis installation, including structures and methods for operation of a force agency 105 and a responsive quantitative assessment 110 with respect to installation of a prosthesis P (e.g., an acetabular cup) into a prepared cavity in a portion of bone (e.g., an acetabulum). Agency 105 may include several different types of force applicators, including vibratory insertion agencies and/or controlled impaction agencies and/or constant applied force and/or other force profile as described in the incorporated patents and applications. Quantitative assessment 110 may include a processor and sensors for evaluating parameters and functions as described herein including a rigidity metric and an elasticity metric, for press-fit fixation of prosthesis P, such as in realtime or near-realtime operation of force agency 105.

Figure 2:
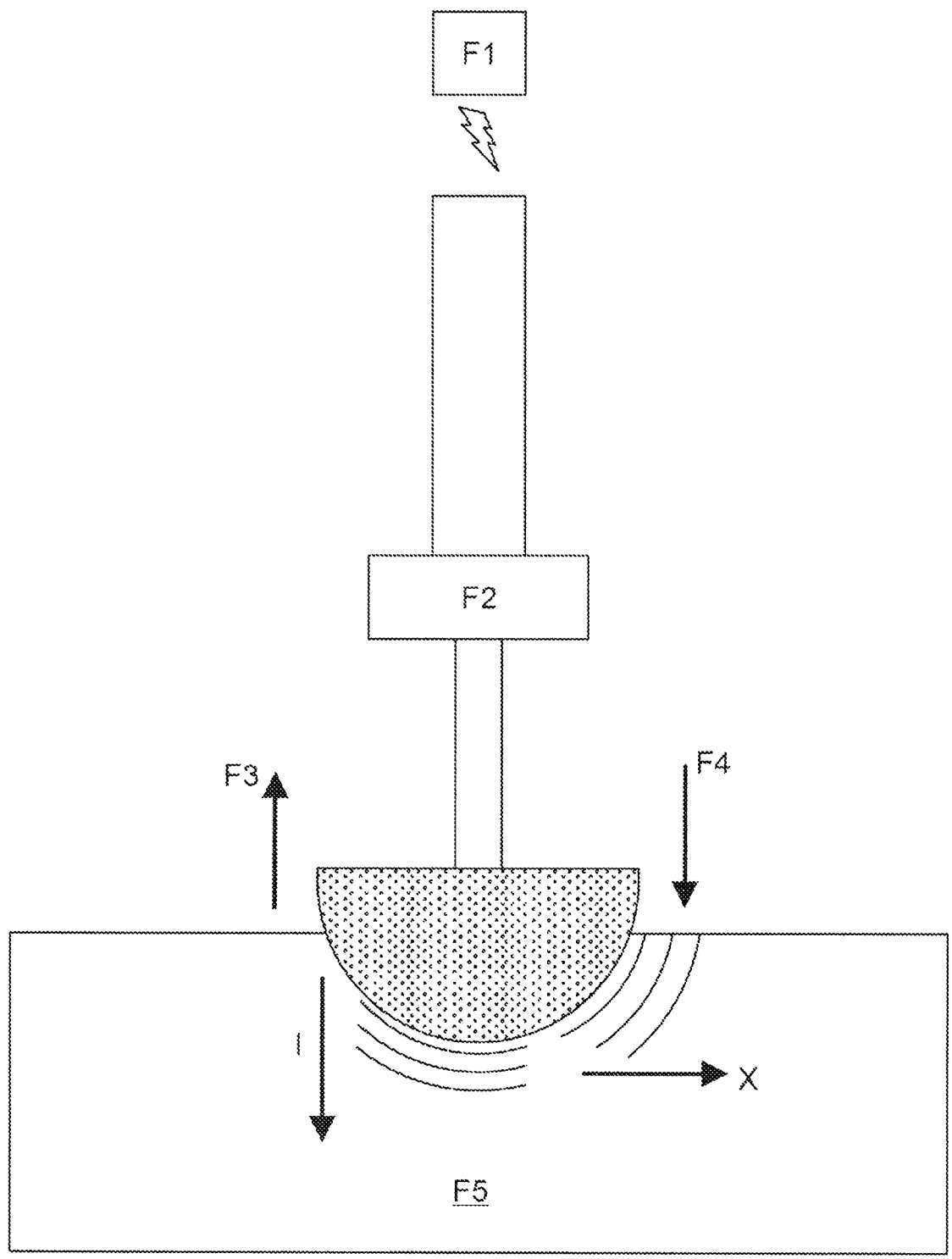
FIG. 2 illustrates an identification of forces in a press fit fixation installation of a prosthesis.

FIG. 2 illustrates an identification of forces in a press fit fixation installation of a prosthesis. These forces, as illustrated, include F1 (applied force), F2 (responsive force in smart tool), F3 (resistive force to installation), F4 (axial extractive force), and/or F5 (force in bone substrate). There may be other forces that may be measured or determined to be correlated, responsive, and/or related to these forces. In some circumstances, multiple related or correlated forces may be "fused" into a fusion force that provides a robust evaluation of the component forces, with any appropriate individual weightings of component forces in the fused force. That is some embodiments, a press-fit fixation may be assessed based upon contributions from multiple forces fused together rather than evaluations of individual forces or derivatives thereof.

When press fitting an acetabular component into an undersized cavity, one may expect to encounter three regions with distinct characteristics: (a) poor seating and poor pull out force; (b) deep insertion and good pull out force; and (c) full insertion which may also have strong fixation but includes higher (and possibly much higher) risk of fracture.

Some embodiments may exhibit relationships between extraction force (F4) and cup insertion CI with respect to similarity and proportionality to a standard stress/strain curve of material deformation.

While two collisions occur during the process of prosthesis impaction into bone in some embodiments for each force application, a proximal collision is usually elastic and typically presents a maximum value of F1 for any given impact energy E of the force application. A distal collision is conversely initially inelastic and progresses to an elastic state as insertion no longer occurs. In some experiments, force measurements in the impaction rod (F2) and bone (F5) may represent the distal collision.

Figure 3:
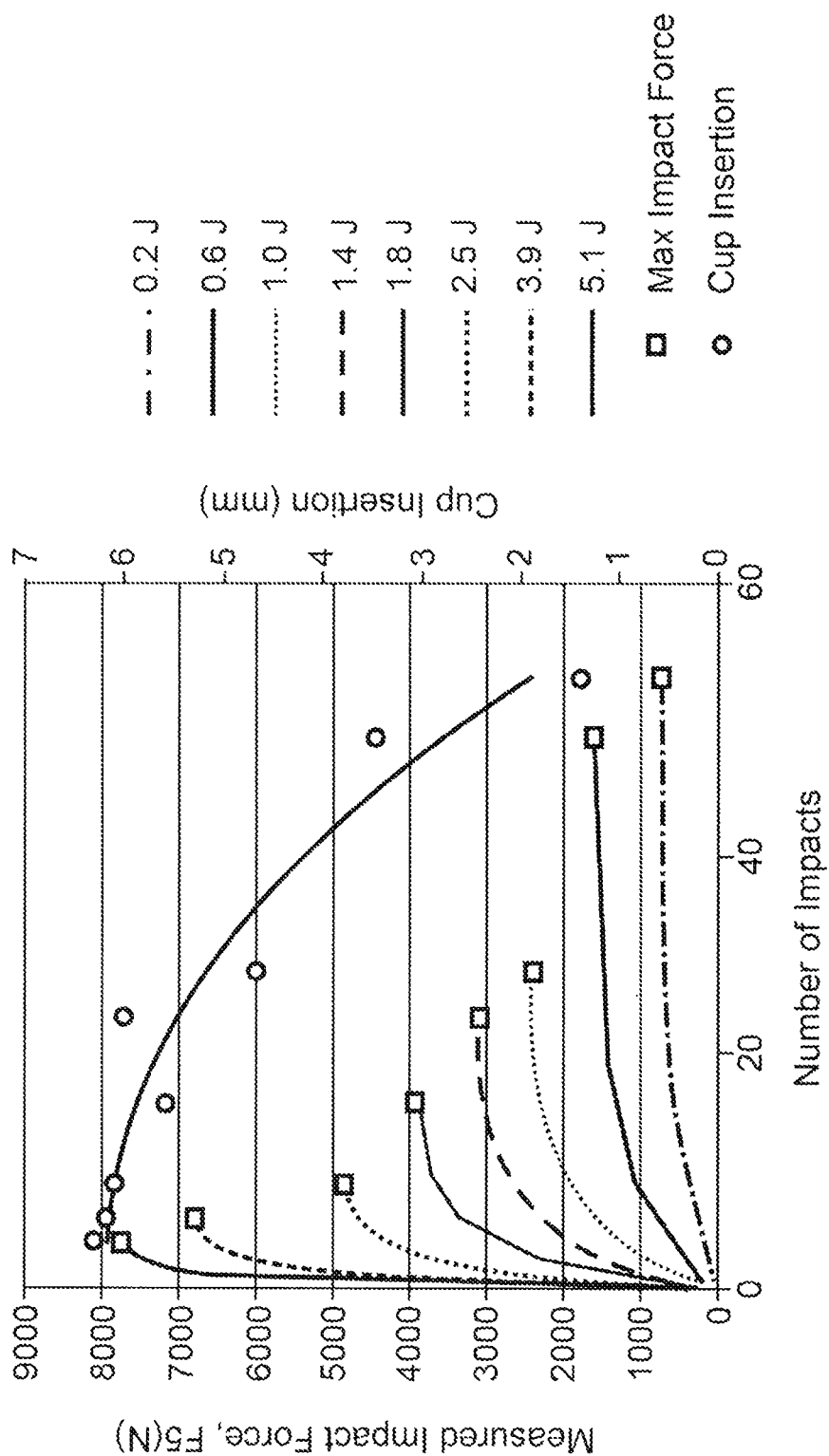
FIG. 3 illustrates a set of relationships between measured impact force (e.g., F5), number of impacts (NOI), cup insertion (CI), and impact energy Joules (J)

FIG. 3 illustrates a set of relationships between measured impact force (e.g., F2, F3, and/or F5 and/or derivatives and/or combinations thereof), number of impacts (NOI), cup insertion (CI), and impact energy Joules (J). Experiments in the study of vibratory insertion of orthopedic implants [Published Patent App. Invasive Sensing Mechanism: Pub No. 20170196506, incorporated herein by reference in its entirety for all purposes] where an oversized acetabular prosthesis, Zimmer Continum Cup (62 mm) was inserted into an undersized (61 mm) bone substitute cavity (20 lbs Urethane foam), using three different insertion techniques including controlled impaction, vibratory insertion, and constant insertion. The forces at play were considered in FIG. 2. An 8900N force gauge was placed within the polyurethane sample to measure forces in the cavity F5.

With the controlled impaction technique we tested eight-drop heights producing a range of impact energies from 0.2 J to 5.0 J corresponding to impact forces ranging from 550N to 8650N. Five replications were performed for each height, with a total sample population of 40 units. For each sample, impacts were repeated at a selected drop height until implant displacement between impacts were within the measurement error of 0.05 mm. Peak impact force in bone F5, total cup insertion CI, and number of impacts NOI to full insertion were recorded for each sample. Cup stability was measured by axial extraction force by means of a pull test using Mark 10 M5-100 test stand and force gauge. The results are shown in Table I.

TABLE I

Drop Test Results

| Drop Height (mm) | Impact Energy (J) | Maximum Impact Force in bone F5 (N) | Mean Number of Impacts | Cup Insertion (mm) | Extraction Force F4 (N) |
|---|---|---|---|---|---|
| 10 | 0.2 | 774 | 52 | 1.4 | 71 |
| 30 | 0.6 | 1641 | 47 | 3.5 | 258 |
| 50 | 1.0 | 2437 | 27 | 4.7 | 480 |
| 70 | 1.4 | 3104 | 23 | 6.0 | 676 |
| 90 | 1.8 | 3927 | 16 | 5.6 | 765 |
| 130 | 2.5 | 4870 | 9 | 6.1 | 827 |
| 200 | 3.9 | 6814 | 6 | 6.2 | 849 |
| 260 | 5.1 | 7757 | 4 | 6.3 | 867 |

These data indicate that every level of impact energy is associated with a final depth of cup insertion CI, a plateauing of the force response in bone F5 to an asymptote, and a certain rate of insertion inversely related to the number of impacts NOI required for insertion. As an example, it took 4 impacts for a maximum applied force of 7757 N to insert the cup 6.3 mm, whereas it took 52 impacts for a maximum applied force of 774N to insert the cup 1.4 mm.

Figure 4:
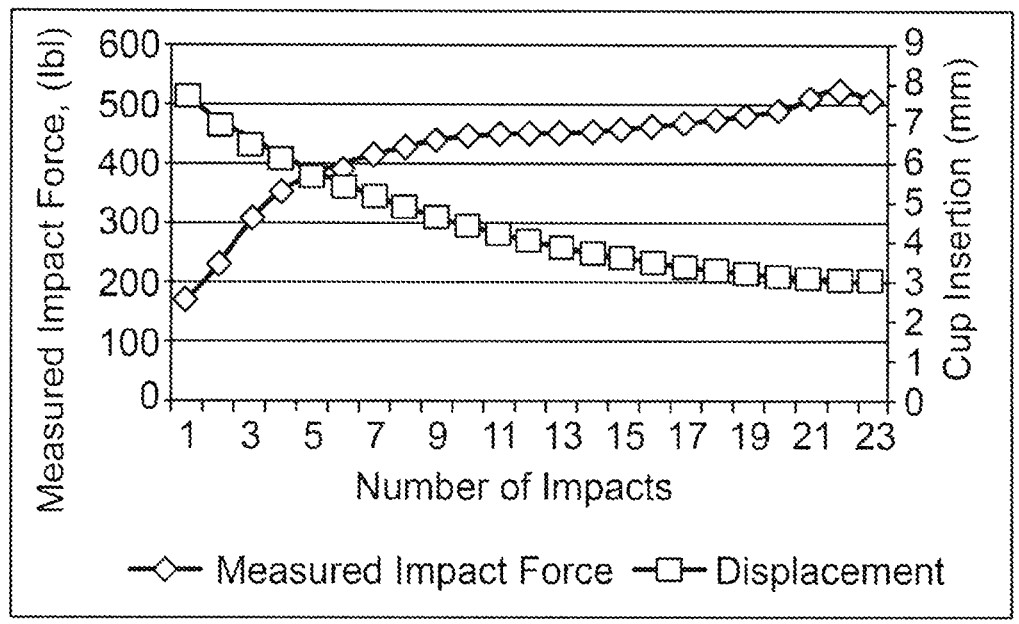
FIG. 4 illustrates a relationship of force in bone (e.g., F5) and cup insertion (CI) for 1.0 Joules (J)
Figure 5:
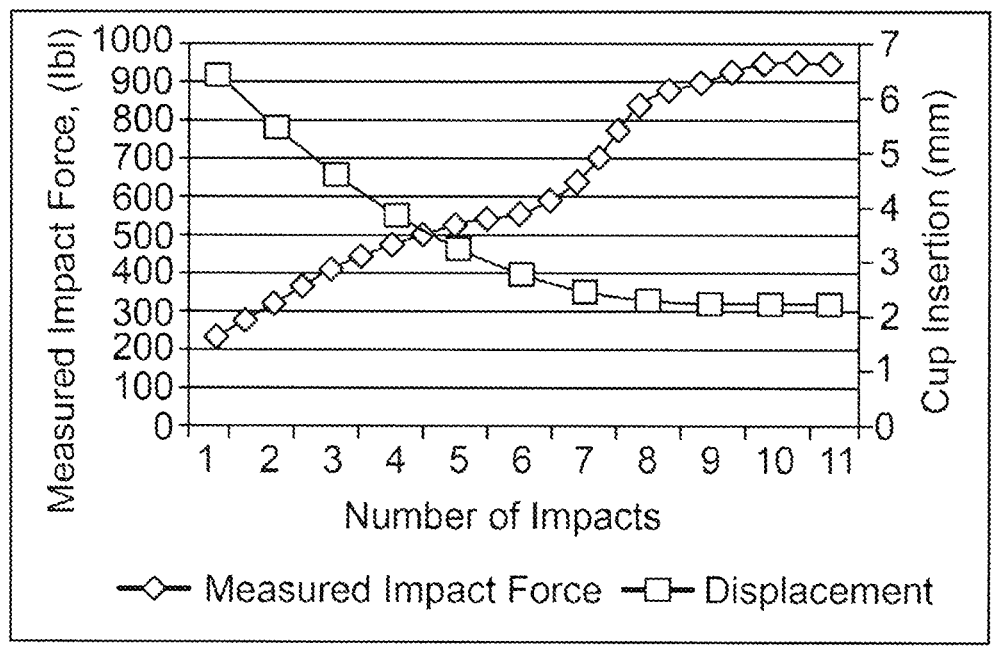
FIG. 5 illustrates a relationship of force in bone (e.g., F5) and cup insertion (CI) for 1.8 Joules (J)

FIG. 4 illustrates a relationship of force in bone (e.g., F5) and cup insertion (CI) for 1.0 Joules (J) and FIG. 5 illustrates a relationship of force in bone (e.g., F5) and cup insertion (CI) for 1.8 Joules (J). A decaying of the force response in bone F5 to an asymptote (when ΔF5 approaches 0) could be used as a parametric value guiding incremental application of energy to obtain optimal press fit fixation of implants. This phenomena is identified herein as the rigidity factor (or rigidity metric) which appears to reach a maximum for any given impact energy.

Figure 6:
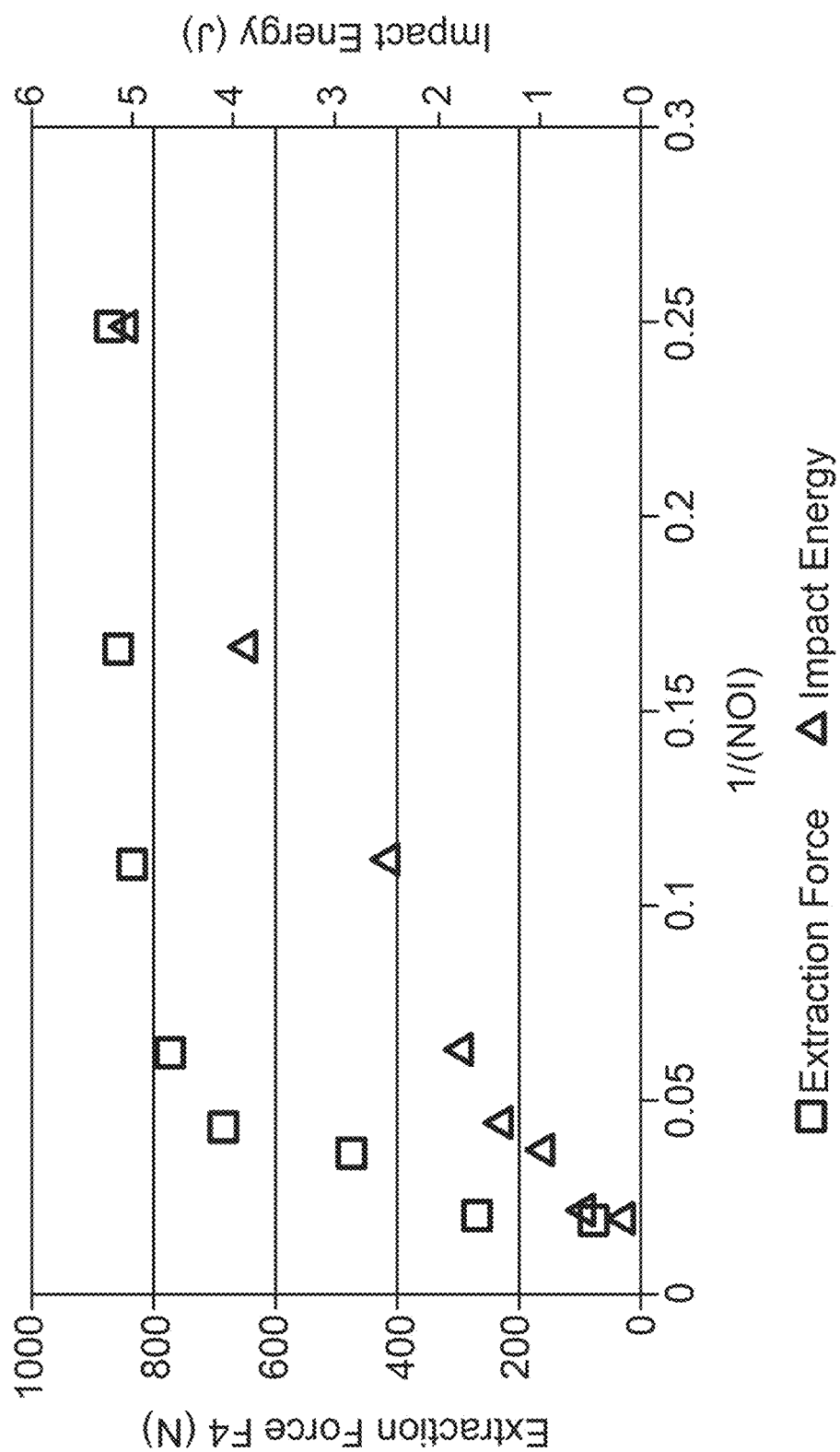
FIG. 6 illustrates a relationship between a rate of insertion (1/NOI), extractive force (e.g., F4), and impact energy.

FIG. 6 illustrates a relationship between a rate of insertion (1/NOI), extractive force (e.g., F4), and impact energy. A direct relationship was observed between rate of insertion, inversely related to number of impacts NOI, and the extractive force F4, and this phenomenon is termed an elasticity factor (or elasticity metric), which appears to provide a real-time estimation of the extractive force of the implant/bone interface, as well as an indirect measure of the elastic/plastic behavior of the aperture of bone. A decaying rate of insertion is considered and appears inversely related to a number of impacts and suggests an ultimate stress point of the cavity aperture.

Figure 7:
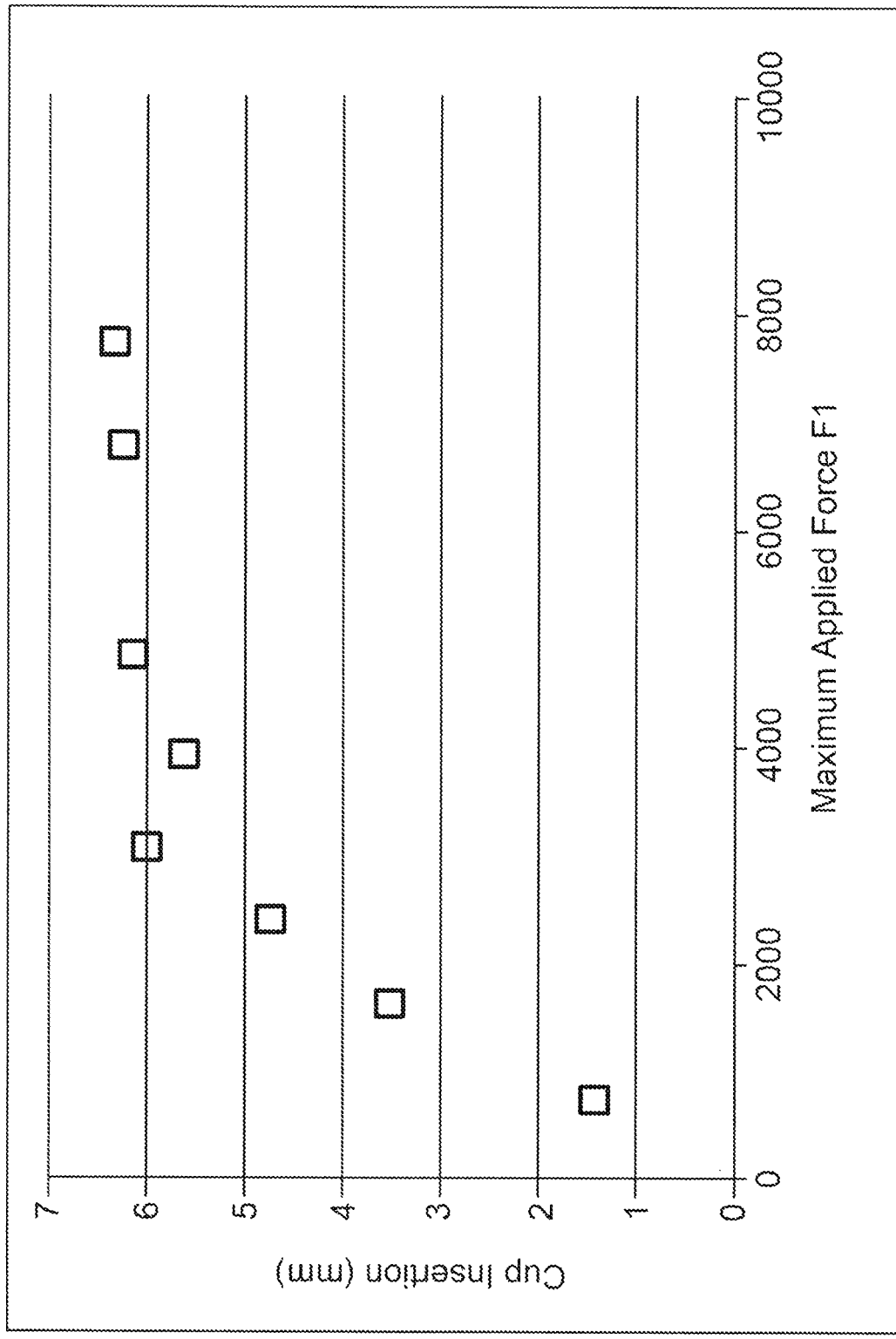
FIG. 7 illustrates a relationship between maximum applied force (e.g., F1) and cup insertion (CI)
Figure 8:
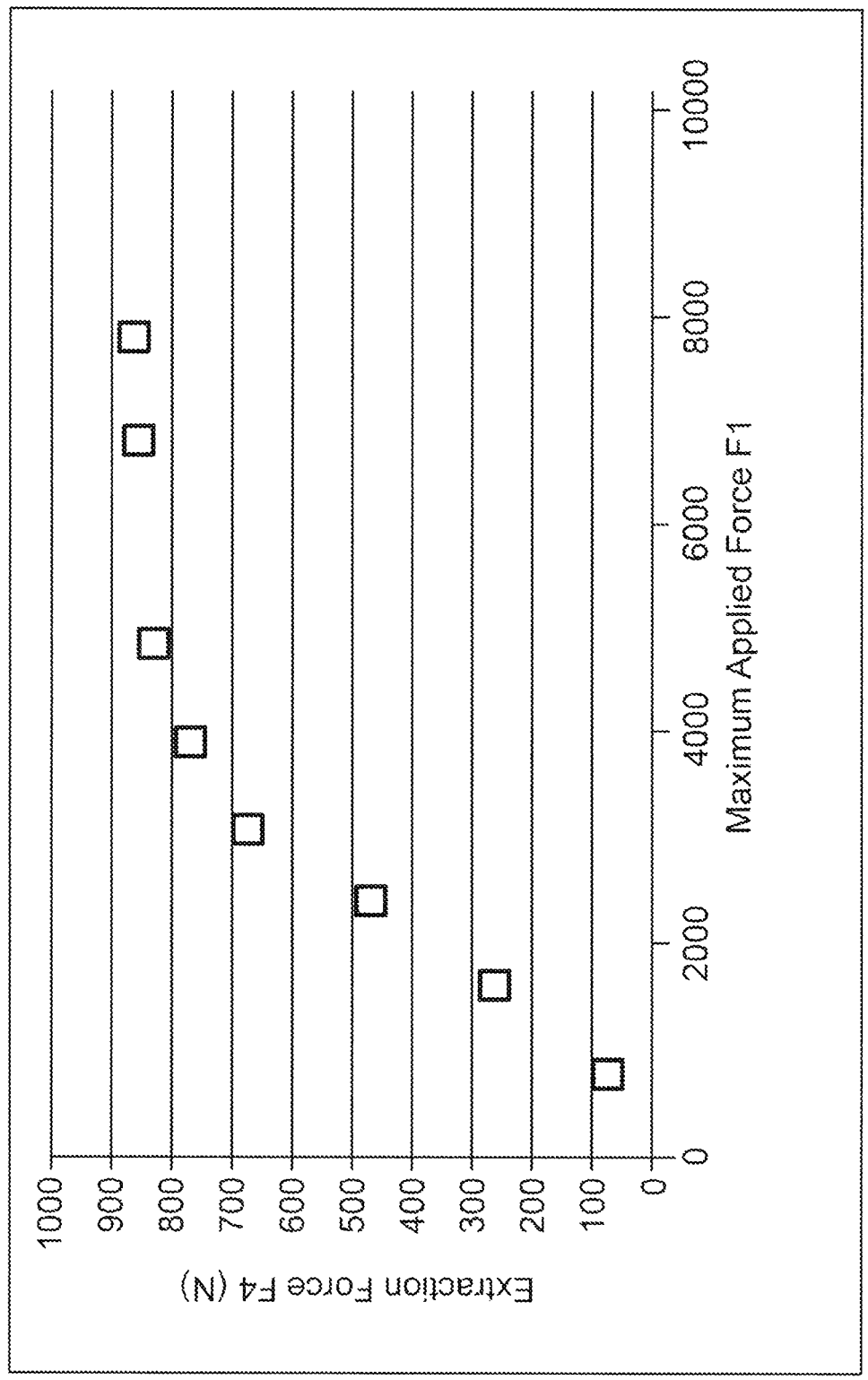
FIG. 8 illustrates a relationship between maximum applied force (e.g., F1) and an extractive force (e.g., F4)

FIG. 7 illustrates a relationship between maximum applied force (e.g., F1) and cup insertion (CI) and FIG. 8 illustrates a relationship between maximum applied force (e.g., F1) and an extractive force (e.g., F4). The relationships of applied force F1 and cup insertion CI as well as applied force F1 and extractive force F4 were evaluated and showed characteristic non-linear curves.

Of note was the observation that an inflection point or (range) exists above which increased applied force F1 (impact energies) did not appear to provide any meaningful increase in cup insertion CI or extraction force F4. As example 1.8 joules of impact energy produced 5.6 mm (89%) of cup insertion CI and 827N (88%) of extraction force F4. An additional 3.3 joules of impact energy was required for a marginal insertion gain of 0.7 mm and extraction force gain of 102N.

Questions were posed as to how much force is required for optimal press fit fixation? Does the insistence to fully seat the cup work against the patients and surgeon? Do surgeons risk fracturing the acetabulum in the desire to fully seat the cup? The existence of polar gaps in acetabular press fit fixation have been clinically studied and shown no adverse outcomes.

It was contemplated that a point or (a small range), defined by the parametric values above, exists which could produce the best fixation short of fracture (BFSF) and an embodiment may propose BFSF as an ideal endpoint for all press fit joint replacement surgery. BFSF may, in some situations, act not only as a point of optimal press fit, but also define a sort of speed limit or force limit for the surgeon.

In this application an embodiment may develop a method described as the invasive sensing mechanism (ISM), by which the end point BFSF can be defined in four chosen systems. Additionally, an embodiment may develop an Automatic Intelligent Prosthesis Installation Device (AI-PID) that can quantitatively access this point. The following concept is proposed for a fixation algorithm to achieve BFSF for any implant/cavity interface. (A Double Binary Decision)

Figure 9:
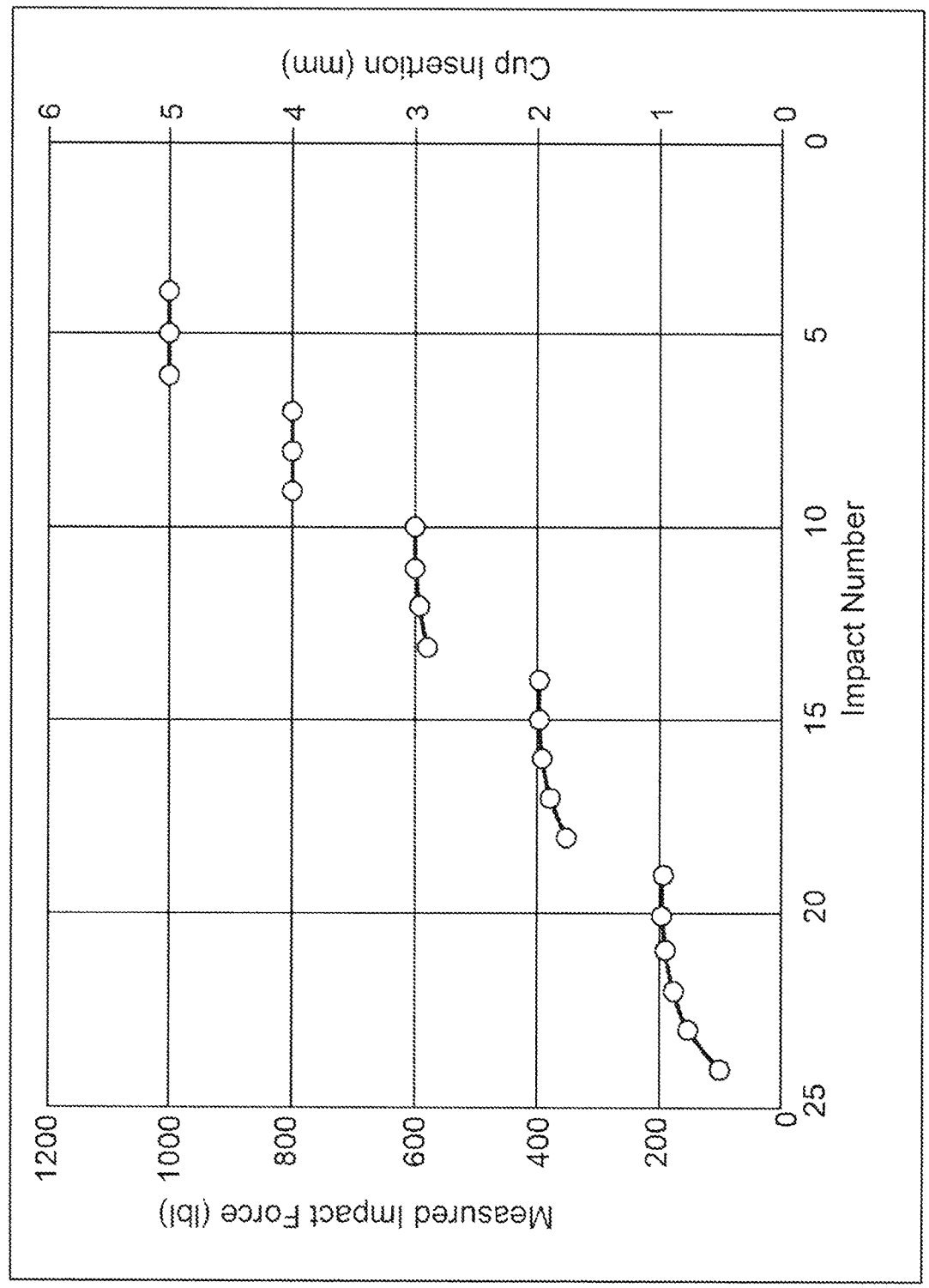
FIG. 9 illustrates a representative force response for incrementing impact energies.

FIG. 9 illustrates a representative force response for incrementing impact energies. The rigidity factor represented by plateauing levels of force in bone (e.g., F5) can be used to guide incremental increase in impact energy J. For any impact energy J, as the force in bone plateaus to a maximum, no further insertion is occurring; a decision can be made as to whether impact energy should be increased or not. This is the first binary decision. The elasticity factor represented by the speed of insertion of an implant (e.g., inversely related to number of impacts (NOI) required for insertion) can be used to guide the surgeon as to whether application of force should continue or not. This is the second binary decision. Two binary decisions for BFSF which may not include full seating.

Figure 10:
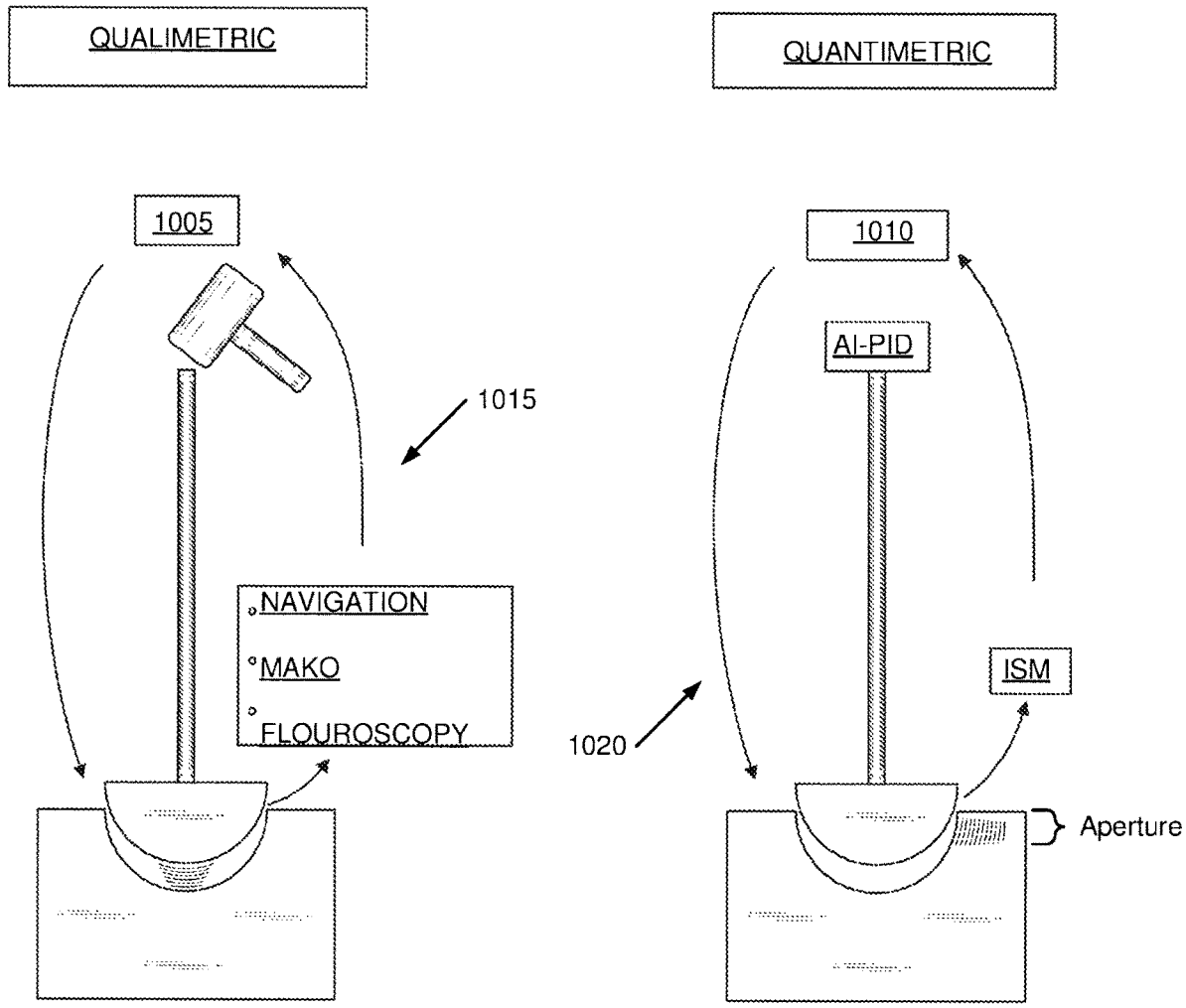
FIG. 10 illustrates a comparison of a quantitative system versus a qualimetric system for evaluating a real time non-visually tracked press fit fixation.

FIG. 10 illustrates a comparison of a quantimetric system (including a measured quantitative determination/use of BFSF) versus a qualimetric system (typically based on a visual qualitative assessment of a depth of insertion) for evaluating a real time non-visually tracked press-fit fixation. An invasive sensing mechanism (ISM) and an automatic intelligent prosthesis installation device (AI-PID) may standardize an application of force and an assessment of a measured quality of fixation in joint replacement surgery, through exploitation of the relationships between the force responses in the installation tool, bone and the interface.

The qualimetric system includes various visual tracking mechanisms (e.g., computer navigation, MAKO assistant, fluoroscopy, and the like) in which an uncontrolled force is applied manually such as by a mallet 1005. The quantitative system operates an insertion agency 1010 which enables application of controlled forces (e.g., force vectors of controlled direction and/or controlled magnitude). The insertion agency may involve ISM which, in some implementations, may assess the stress response of bone at the implant/bone interface as opposed to qualimetric discussed in the above paragraph that does visual tracking.

The qualimetric system includes a striking-evaluation system 1015 in which a mallet strikes a rod which drives a prosthesis into a prepared cavity. The surgeon then qualitatively assesses the placement using secondary cues (audio, tactile, visual imaging) to estimate a quality of insertion and assume a quality of fixation. This cycle of strike and assess continues until the surgeons stop, often wondering whether stopping is appropriate and/or whether they have struck the rod too many times/too hard.

In contrast, a quantitative cycle 1020 in the quantimetric system includes operation of an insertion agency, measurement of force response(s) to determine elastic and rigidity factors, and use these factors to determine whether to continue operation and whether to modify the applied force from the insertion agency. The quantitative system assumes BFSF and optimal press-fit fixation relies primarily on a cavity aperture of a relatively oversized prosthesis/relatively undersized cavity which provides a contact area around a "rim" of the cavity where bone contacts, engages, and fixates the prosthesis. A depth of the aperture region may depend upon a degree of lateral compression of the prepared bone as the prosthesis is installed.

The parametric values of the quantimetric system provide meaningful actionable information to surgeons as to when to increment the magnitude of force, and as to when to stop application of force. Additionally, surgeons currently utilize qualitative means (auditory and tactile senses) as well as auxiliary optical tracking means (fluoroscopy, navigation) to assess the depth of insertion and estimate a quality of fixation during press fit arthroplasty. Application of force to achieve press fit fixation is uncontrolled and based on human proprioceptive and auxiliary optical tracking means. The optimal endpoint for press fit fixation remains undefined and elusive.

An embodiment may include development of a reliable quantitative technique for real-time intra-operative determination of optimal press fit, and the development of a smart tool to obtain this point automatically. The ability to base controlled application of force for installation of prosthesis in joint replacement surgery on the force response of the implant/bone interface is an innovative concept allowing a quantimetric evaluation of the implant/bone interface.

An embodiment for a quantimetric system may include a hand-held tool (See, e.g., FIG. 1) that can produce impact energies of the necessary magnitude and accuracy. A variety of actuation methods can be used to create controlled impacts, including pneumatic actuators, electro magnetics actuators, or spring-loaded masses. An example implementation using pneumatic, vibratory, motorized, controlled, or other actuation. The device shall have industry standard interfaces in order to allow for use with a variety of cup models.

A slide hammer pneumatic prototype is created to allow precise and incremental delivery of energy E. It is equipped with inline force sensors in order to measure resulting forces F1 and F2 and controlled by integrated electronics that provides analysis of F1, F2, $\Delta$F2, number of impacts, and impact energy E. Programed algorithms based on the double binary system described herein will produce successive impacts of a known energy, making two simultaneous binary decisions before each impact: (a) modify energy or not; and (b) apply energy or not. These two binary decisions will be based on parametric values produced by the control electronics, which provides an essential feedback of the implant/bone interface, and the elastic response of bone at the aperture. The following algorithm provides a basic example of the double binary decision making process.

A method for assessing a seatedness and quality of press fit fixation includes a series of operations for installing a prosthesis into a relatively undersized cavity prepared in a portion of bone, including communicating, using an installation agency, a quantized applied force to a prosthesis being press-fit into the cavity; monitoring a rigidity metric and an elasticity metric of the prosthesis with respect to the cavity (some embodiments do this in real-time or near real-time without requiring imaging or position-determination technology); further processing responsive to the rigidity and elasticity metrics, including continuing to install the prosthesis at present level of applied force while monitoring the metrics when the metrics indicate that installation change is acceptable and a risk of fracture remains at an acceptable level, increasing the applied force and continuing applying the installation agency while monitoring the metrics when the metrics indicate that installation change is minimal and a risk of fracture remains at an acceptable level, or suspending operation of the installation agency when the metrics indicate that installation change is minimal when a risk of fracture increases to an unacceptable level.

1. Apply energy E1 and measure F2, number of impacts (NOI), $\Delta$F2.
2. Monitor F2 over number of impacts (NOI), and/or monitor $\Delta$F2 as it approaches zero.
3. When $\Delta$F2 approaches zero, insertion is not occurring for that particular energy E1. If NOI required to achieve this point is sufficiently large (low speed of insertion) as determined by the control algorithm, then E1 is increased to E2
4. Continue steps 1 through 3 until the NOI required for $\Delta$F2 to approach zero is sufficiently small (high speed of insertion) as determined by the control algorithm.
5. The smart tool may be implemented so it will not generate automated impacts after this level is reached. Additional increase in energy E is not recommended but can be produced manually or after a considered override by the surgeon. For example, it may be that no more than one incremental manual increase is recommended or established as a best practice.

Validation of the tool may be performed by comparing the quality of insertion (extractive force F4) produced by AI-PID with those produced by a mallet and standard impaction techniques. Specifically, the two distinct endpoints of (i) BFSF (achieved through AI-PID) and (ii) full seating (achieved through mallet strikes) will be compared to determine differences in the extractive force F4 and fracture incidence. A risk benefit analysis will be done to determine whether additional impacts and insertion beyond BFSF provided any significant value as to implant stability, or conversely led to increased incidence of fracture of the cavity. (As noted herein, it may be the case that BFSF may be achieved without full seating, a stated goal of many conventional procedures.)

It is anticipated that the measurements of F2, and ΔF2 and its comparative analysis with respect to number of impacts NOI will provide a principled and organized process for application of energy to achieve a desired endpoint of fixation BFSF. We expect that the first order relationship of ΔF2 will provide the information as to whether, for any particular level of applied energy, insertion is occurring or not; providing a guidance as to whether applied energy should be increased. We expect the rate of ΔF2 decay to zero will provide information about elastic/plastic behavior of the aperture, indicating when the maximum strain X, normal force FN, and extractive force F4 at the aperture of the bone cavity have been achieved. We anticipate reproducing the results of phase I aim 1, namely that there is a strong correlation between pull force F4 and rate of decay of ΔF2, that an inflection point exists in the elasticity factor, beyond which addition of impact energy will lead to marginal gains in extraction force F4 and depth of insertion, mitigating against goal of full seating as the best policy.

We have indicated that the grasp of bone (bone substitute) on an implant at the aperture can be modeled in some cases by formula such as FN*Us where FN represents the normal forces at the interface, and Us represents the coefficient of static friction. FN is estimated by Hooke's Law and is represented by K.X, where K represents the material properties of bone including the elastic and compressive moduli and X represents the difference in diameter between the implant and the cavity. We note that the value of K can vary dramatically between different ages and sexes. We anticipate this tool to be capable of automatically producing the proper amount of impact energy E, cup insertion CI, stretch on bone X, normal force FN, and extractive force F4 to achieve optimal press fit for patients of various ages and sexes, eliminating an over reliance on surgeon senses and experience.

Having access to this interface sensing phenomena, an embodiment may develop a simple controlled impaction process that allows the surgeon to quantize the impact energy, and deliver it in a controlled and modulatable fashion based on the above two parametric value representing the stress/strain behavior of bone. Some embodiments may develop the concept of controlled force application based on an evaluation of the interface force phenomena (forces felt at the prosthesis/cavity interface). This is in stark contradistinction of uncontrolled application of force with a mallet based on a VISUAL assessment/tracking of the depth of prosthesis insertion (MAKO, all navigation techniques, Fluoroscopy, Nikou—a navigation technique).

There may be many different ways to assess rigidity factor and to assess an elasticity factor. FIG. 11-FIG. 14 illustrates F2 approaching F1 and F5 approaching F1, as well as (ΔF2 approaching 0) and (ΔF5 approaching 0). Additional non-illustrated ways include F3 approaching F1 and ΔF3 approaching 0). As noted herein, data fusion may produce a fusion variable that can measure, evaluate, or indicate rigidity and/or elasticity. For example, one or more of F2, F3, and F5, appropriately weighted, may be fused into a variable that may be used such as by comparing to F1 or delta fused variable compared to a threshold value (such as zero).

Figure 11:
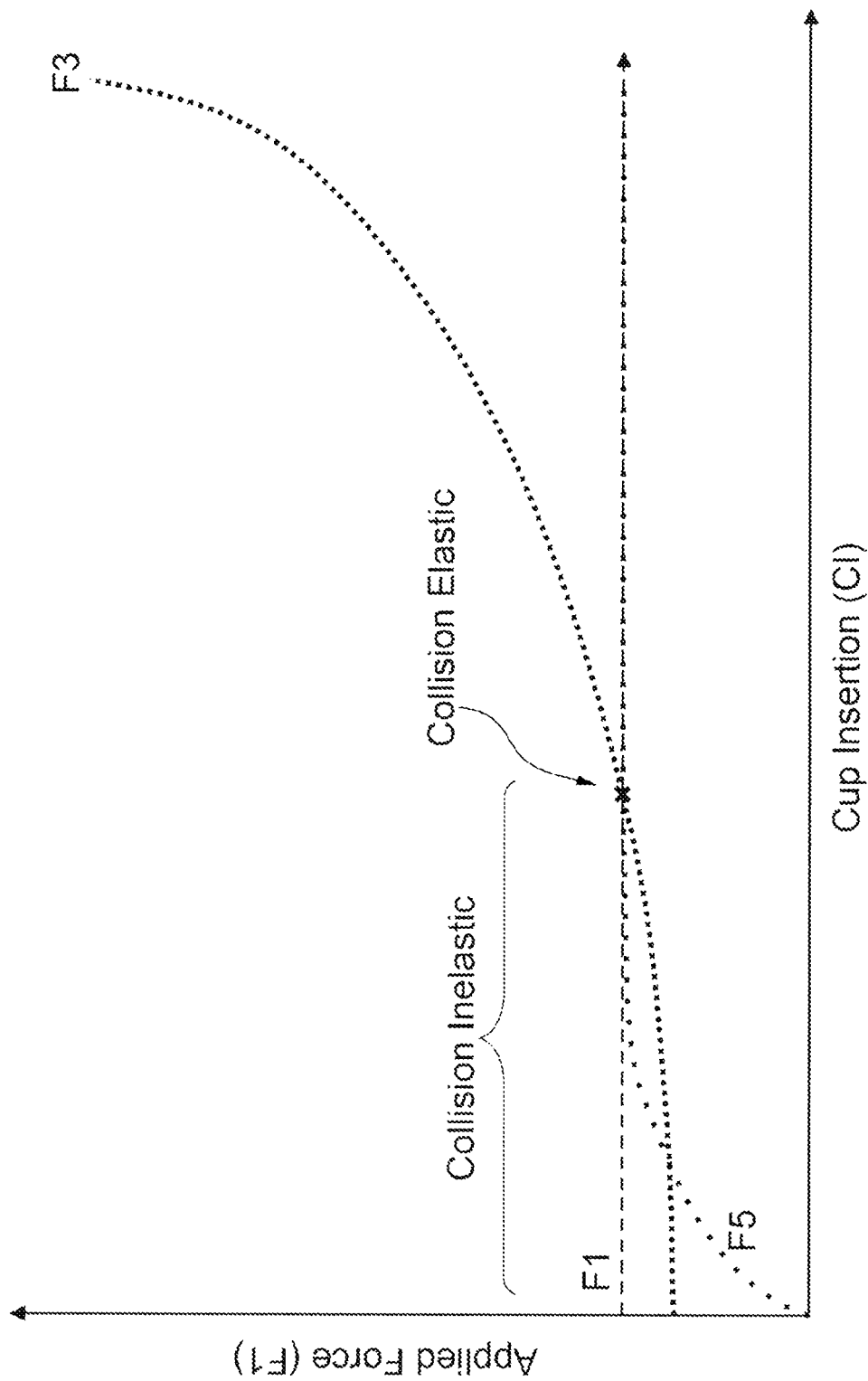
FIG. 11-FIG. 14 illustrate a set of rigidity metric measurements.
Figure 12:
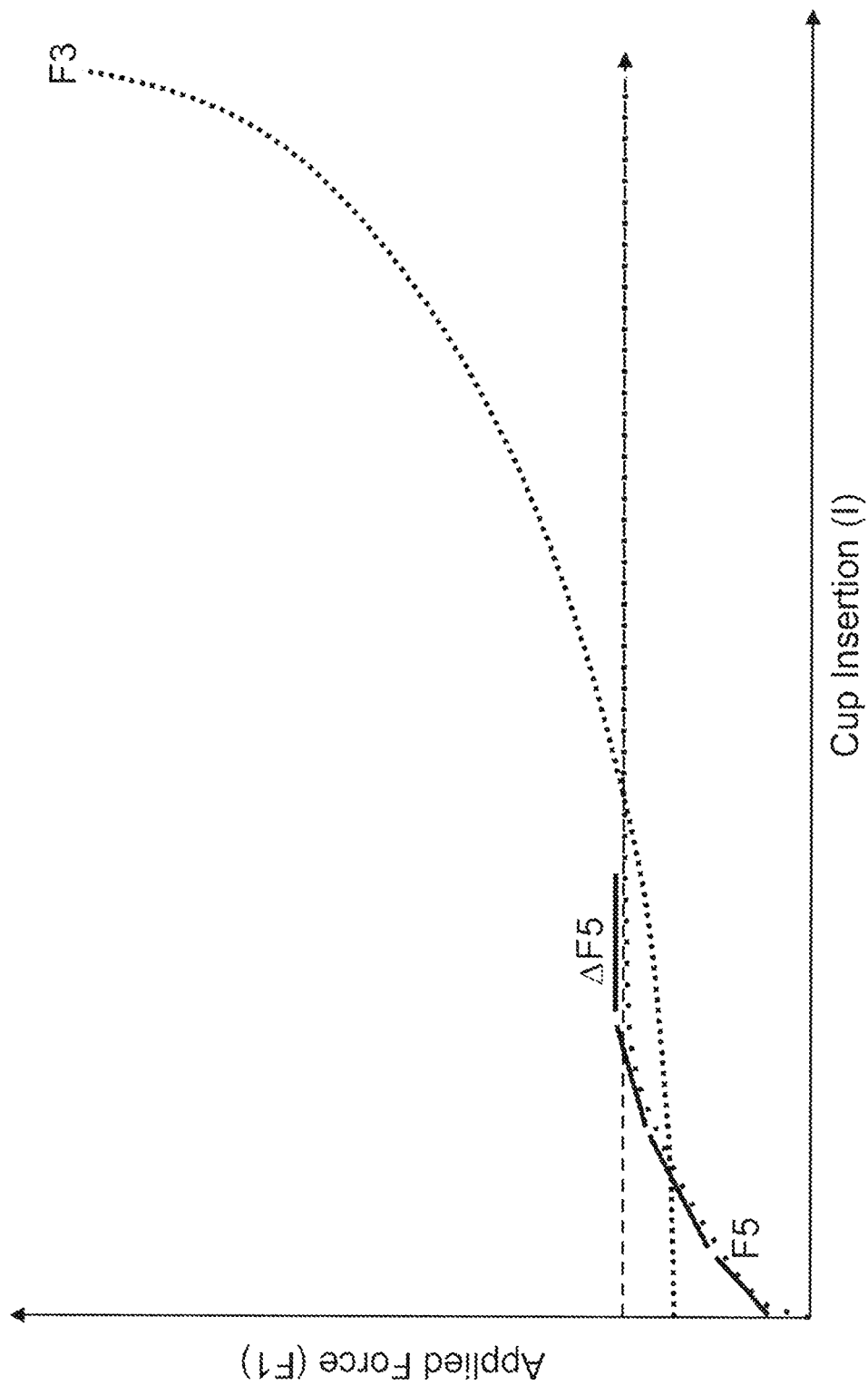
Figure 13:
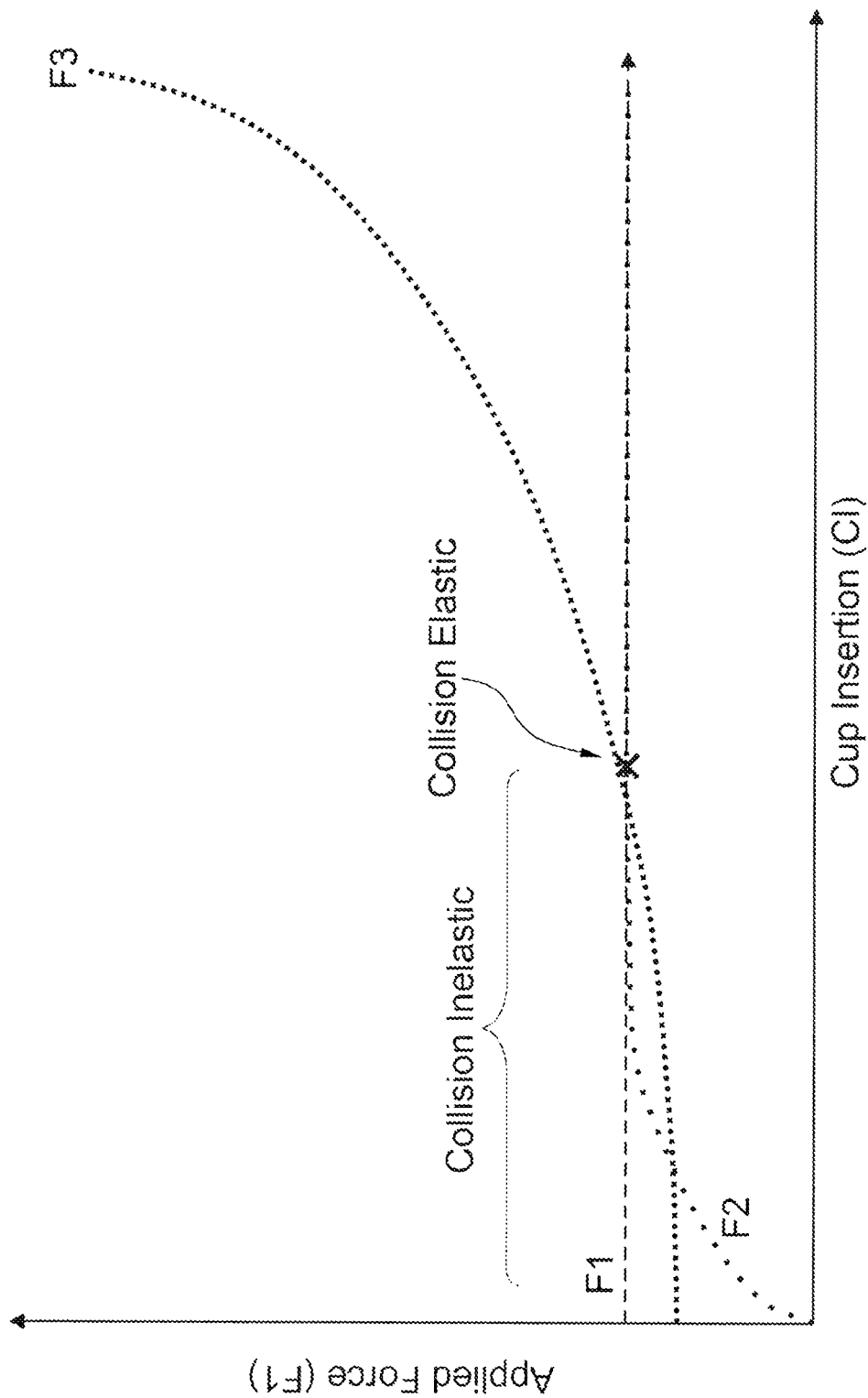
Figure 14:
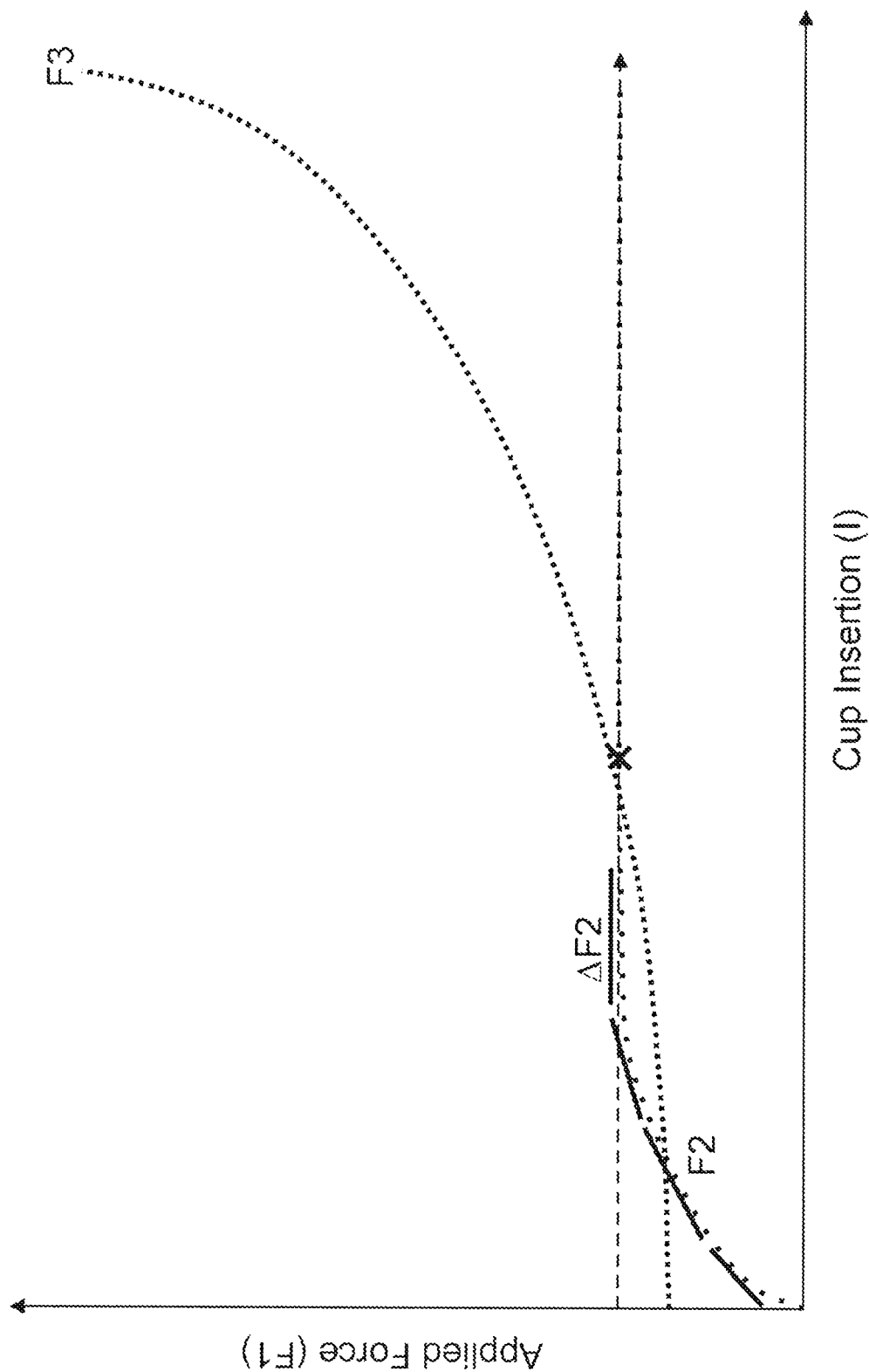

FIG. 11-FIG. 14 illustrate a set of rigidity metric measurements that may be used in the methods and systems described herein. FIG. 11 illustrates a comparison of F5 to F1; FIG. 12 illustrates a comparison of ΔF5 to a predetermined threshold (e.g., 0.0); FIG. 13 illustrates a comparison of F2 to F1; and FIG. 14 illustrates a comparison of ΔF2 to a predetermined threshold (e.g., 0.0).

Figure 15:
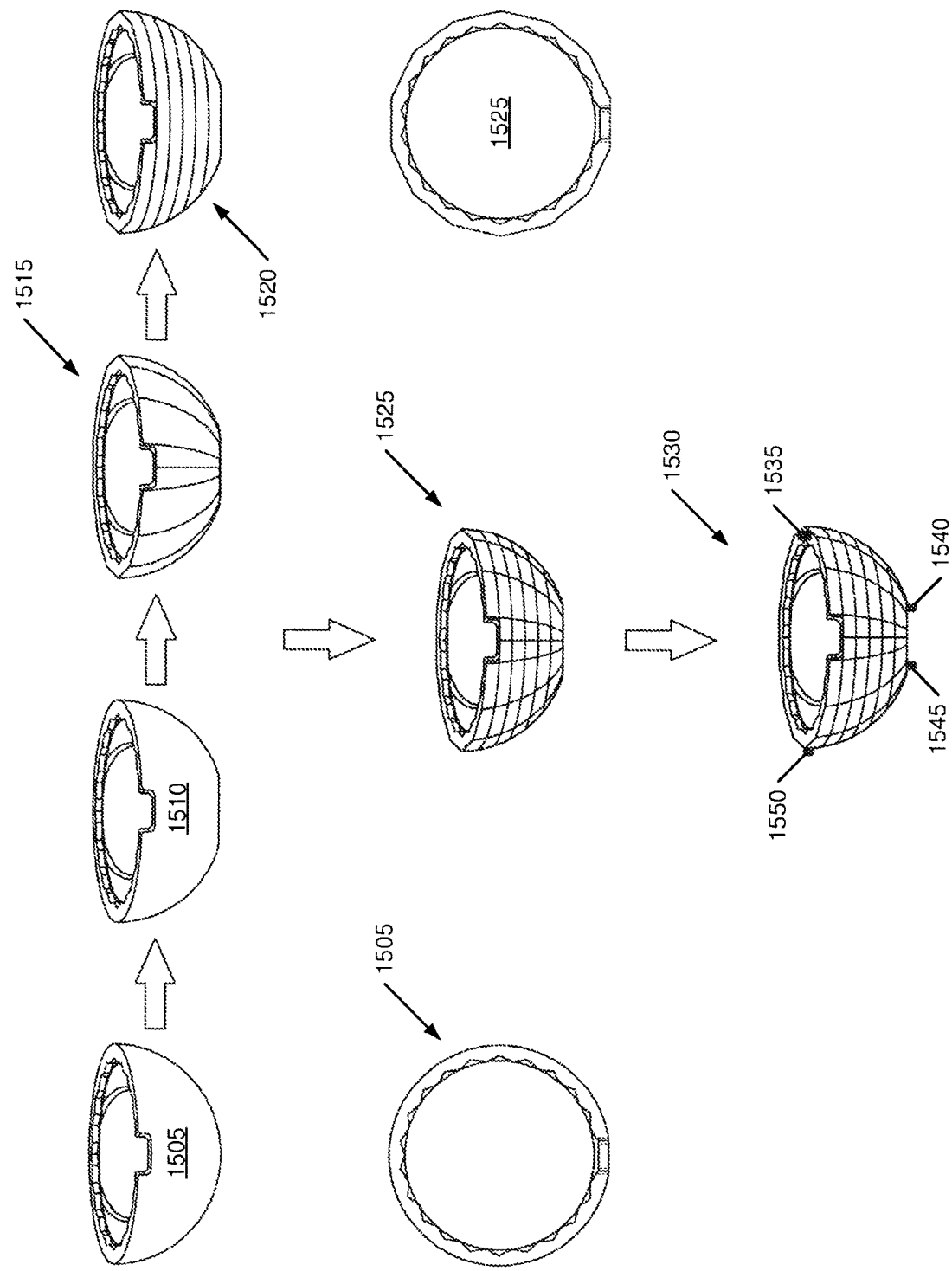
FIG. 15 illustrates an evolution of an acetabular cup consistent with improving press fit fixation.

FIG. 15 illustrates a possible evolution of an acetabular cup 1505 consistent with improving press fit fixation. As noted, a conventional acetabular cup for an implant includes a hemispherical outer surface designed to be installed/impacted into a prepared bone cavity (also hemispherical produced from a generally hemispherical reamer for example).

Different stages of evolution illustrate possible improvements to prosthesis embodiments that are responsive to assumptions and embodiments of the present invention. An assumption of some conventional systems is that full depth of insertion results in a maximum extractive press fit fixation. In contradiction to this assumption, it may be the case that embodiments of the present invention achieve maximum/optimal press fit fixation (BFSF) short of full insertion (i.e., intentional presence of a polar gap).

There may be advantages to reducing polar gaps, and rather than full insertion, a modification to the prosthesis may include a truncated hemisphere (snub nosed) cup 1510. There is a desire to reduce insertion forces while maximizing press fit fixation. Evolution of the prosthesis may incorporate several different ideas, including asymmetric deformation control using a truncated cup with longitudinally extending ribs 1515 and laterally extending planks 1520—the combination of ribs and planks cup 1525 may produce an asymmetric deformation to improve installation (such as making it easier to install and more difficult to remove). Further, a perimeter of an improved cup may include a discrete polygon having many sides. The reduced surface area contacting the prepared cavity may reduce force needed to install while the vertices of the polygon may provide sufficient press-fit fixation. Cup 1525 may include tuned values of the snub, different stiffnesses of ribs and planks, a perimeter configuration of the regular/irregular non-hemispherical polygonal outer surface. These vertices themselves may be angular and/or rounded, based upon design goals of a particular implementation of an embodiment to achieve the desired trade-offs of installation efficiency and press-fit fixation to improve the possibility of achieving BFSF.

These concepts have implications on how the acetabular (all press fit prosthesis) prosthesis are made. If it holds true that the dome of the cup mostly acts like a wedge to cause fracture, it may be best to eliminate the dome (flatten the cup) and change the geometry of the cup to be more like a frustum polygon with nth number of sides, or a hemisphere with a blunted dome.

A. With the ability to provide a proportional amount of force for any particular (implant/bone) interface, we can expect to use just the right amount of force for installation of the prosthesis (not too much and not too little). Additionally we have previously in U.S. patent application Ser. No. 15/234,927, expressly incorporated herein, discussed methods to manufacture prosthesis with an inherent tendency for insertion, MECHANICAL ASSEMBLY INCLUDING EXTERIOR SURFACE PREPARATION. Specifically, we have descried the concept of two dimensional stiffness incorporated within the body of the prosthesis, which would produce a bias for insertion due to the concept of undulatory motion, typically observed in Eel and fish skin.

FIG. 15 includes a side view of a prosthesis including a two-dimensional asymmetrical stiffness configuration, and illustrates a top view of prosthesis. The prosthesis may include a set of ribs and one or more planks disposed as part of a prosthetic body, represented as an alternative acetabular cup. The body may be implemented in conventional fashion or may include an arrangement consistent with prosthesis P. The ribs and plank(s) are configured to provide an asymmetric two-dimensional (2D) stiffness to body that may be more conducive to transmission of force and energy through the longitudinal axis of the cup as opposed to circumferentially. Ribs are longitudinally extending inserts within body (and/or applied to one or more exterior surfaces of body). Plank(s) is/are laterally extending circumferential band(s) within body (and/or applied to one or more exterior surfaces of body). For example, planks may be "stiffer" than ribs (or vice-versa) to produce a desired asymmetric functional assembly that may provide for an undulatory body motion as it is installed into position.

Based on our understanding of the acetabular prosthesis/bone interface in our Invasive sensing studies in one or more incorporated patent applications and in conjunction with the incorporated '927 application of MECHANICAL ASSEMBLY INCLUDING EXTERIOR SURFACE PREPARATION, we anticipate that the prosthesis of the future may have different characteristics.

A. The acetabular component may be shaped more like a frustum with Nth (e.g., 160 sides) and an amputated dome. The snubbed dome of the new prosthesis would not engage the acetabular fossa (Cotyloid fossa) allowing the new prosthesis fully engage the stronger acetabular walls/rim (constituted by the ilum, ischium and pubic bones). This shape of prosthesis avoids the possibility of a wedge type fracture which can be produced by the dome of a hemispherical implant.

B. Each angle of the frustum may produce longitudinal internal rib extending from the rim distally, (developed within the structure of the prosthesis by additive manufacturing by controlling the material properties of crystalline metal), that is more flexible than the horizontal stiffer planks that extend from the rim to the snub distally in a circumferential fashion. (See the incorporated '927 application). This shape of prosthesis will have a strong bias for insertion due to undulatory motion, and will require less force for installation.

Permanent or Removable Sensors on the surface of the Prosthesis.

A. As described herein, in some experiments that when F2 approaches F1, that in fact F1=F2=F3=F5. That is, when the implant/bone collision becomes elastic, the resistive force at the interface F3 and the forces felt in bone F5 can be inferred from applied force F1 and force felt in tool F2. This can provide the surgeon valuable information about the forces she is imparting to the bone. We also contemplate that F3 and F5 can be directly measured by application of mechanical and biologic sensors directly on a sensing prosthesis 1530. We believe given the mass production and ubiquitously available sensors, at some point, the prosthesis of the future would be equipped with its own sensor (biologic and or mechanical) to convey to the surgeon the forces being imparted into the bone, to prevent excessive forces on bone, as well as to prevent loose fitting prosthesis. Sensors on the applied on the surface of the prosthesis to measure interface or dome pressure (F3 or F5) can be permanent or removable i.e., a slot on the side of the prosthesis can allow incorporation of a small sliding sensor to provide information about the interface to the system. Examples of incorporated sensors, one or more which may be used, may include an internal sensor 1535, a mechanical sensor 1540, a biologic sensor 1545, and an external sensor 1550.

B. Data Fusion of F2, F5, F3 for most sensitive evaluation of stress response of Bone at the Implant Bone Interface—multiple parameters are weighted and merged or fused that may provide a robust parameter offering improved performance over reliance on a single parameter.

2. Application of Force based on a Sensory (Not Visual) Evaluation of Implant/Bone Interface.

A. For years surgeons have applied uncontrolled force to impact prosthesis into bone, and have assessed the quality of insertion by human visual, tactile and auditory means. More recently surgeons have begun to use visual tracking means such as fluoroscopy, computer navigation (including Nikou), and MAKO techniques to assess depth of insertion. We are the first to suggest that the application of force for installation of prosthesis should be predicated on the force sensing activity of the prosthesis/bone interface. This is a new technique that predicates application of force for installation of prosthesis to be based (NOT VISUAL TRACKING MEANS—depth of insertion) but rather (FORCE SENSING MEANS OF THE INTERFACE—proof resilience). This is a novel concept that will eliminate too tight and too loose press fit fixation of all prosthesis, and associated problems such as subsidence, loosening, and infection.

Figure 16:
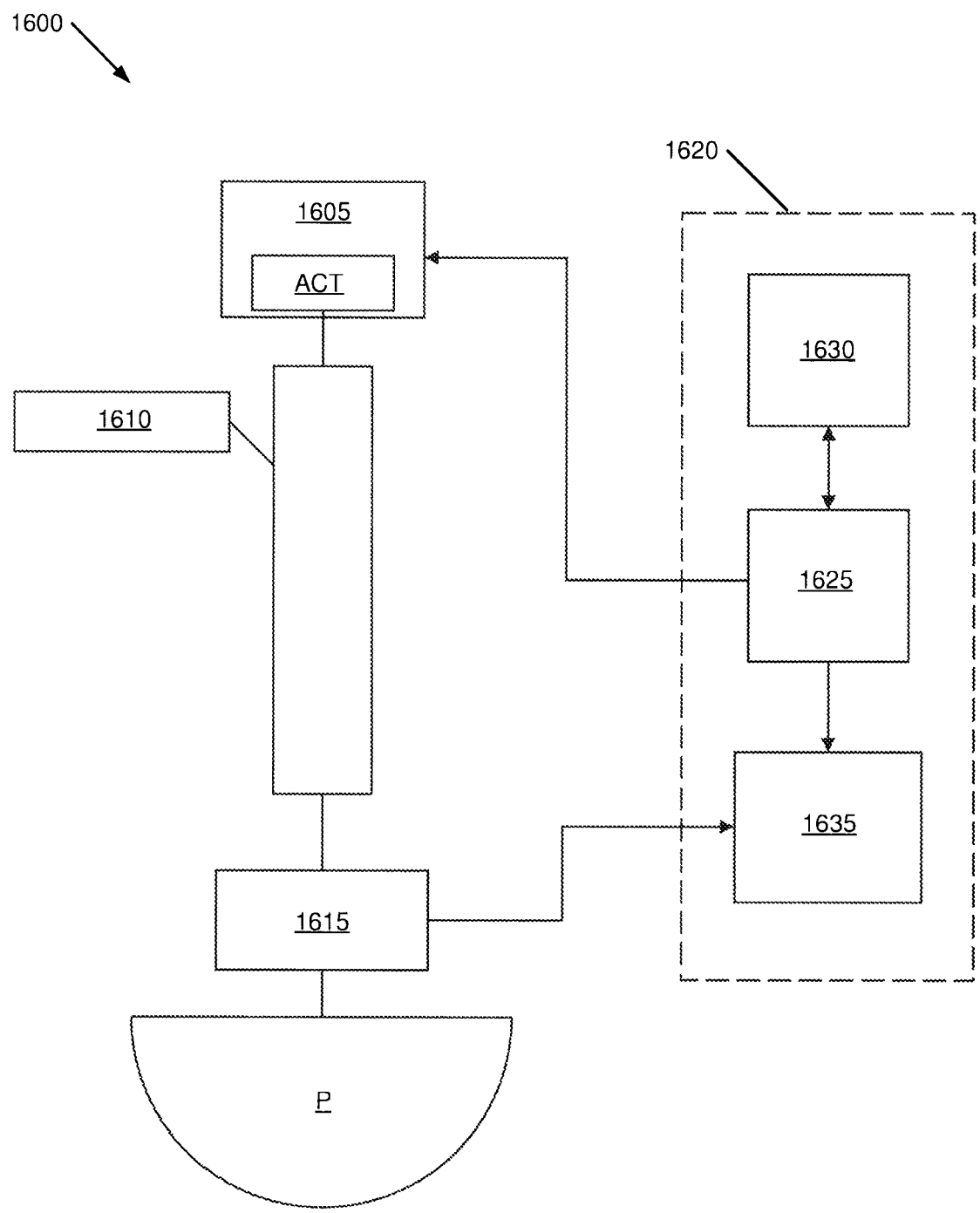
FIG. 16 illustrates a particular embodiment of a $BMD_X$ force sensing tool.

FIG. 16 illustrates a particular embodiment of a $BMD_X$ force sensing tool 1600. Tool 1600 allows indirect measurement of a rate of insertion of an acetabular cup and may be used to control the impact force being delivered to a prosthesis based upon control signals and the use of features described herein. Tool 1600 may include a controllable force applicator (e.g., an actuator) 1605, an impaction transfer structure 1610 (e.g., impaction rod), and a force sensor 1615.

Applicator 1605 may include a force sensor to measure/determine F1 (in some cases applicator 1605 may be designed/implemented to apply a predetermined and known_a priori force.

Structure 1610 transfers force as an insertion agency (for prosthesis implant applications) to prosthesis P and sensing system 1615 measures a realtime (or near realtime) force response of prosthesis P to the insertion agency while it is being implanted into the implant site. There are many different possible force response mechanisms as described herein. For example, F2, F3, F5, and first/second order derivatives and combinations thereof as noted herein. In some cases, sensing system 1615 may include in-line or external sensor(s) associated with or coupled to structure 1610. In other cases, some embodiments of system 1615 may include sensor(s) associated with the bone or cavity or other aspect of the cavity, prosthesis, cavity/prosthesis interface or other force response parameter. System 1615, as noted herein, may include multiple concurrent sensors from different area including one or more of tool, prosthesis and bone/cavity.

One representative method for force measurement/response would employ such a tool 1600. Similar to the impaction rod currently used by surgeons, tool 1600 may couple to an acetabular cup (prosthesis P) using an appropriate thread at the distal end of structure 1610. Applicator 1605 may couple to a proximal end of structure 1610, and create an insertion agency (e.g., controlled and reproducible impacts) that would be applied to structure 1610 and connected cup P. A magnitude of the impact(s) would be controlled by the surgeon through a system control 1620, for example using an interface such as a dial or other input mechanism on the device, or directly by the instrument's software. System control 1620 may include a microcontroller 1625 in two-way communication with a user interface 1630 and receiving inputs from a signal conditioner 1635 receiving data from force sensing system 1615. Controller 1625 is coupled to actuator 1605 to set a desired impact profile including a set of force applications that may change over time as described herein.

Sensing system 1615 may be mounted between structure 1610 and acetabular cup P. System 1615 may be of a high enough sampling rate to capture the peak force generated during an actuator impact. It is known that for multiple impacts of a given energy, the resulting forces increase as the incremental cup insertion distance decreases/

This change in force given the same impact energy may be a result of the frictional forces between cup P and surrounding bone of the installation site. An initial impact may have a slow deceleration of the cup due to its relatively large displacement, resulting in a low force measurement. The displacement may decrease for subsequent impacts due to the increasing frictional forces between the cup and bone, which results in faster deceleration of the cup (the cup is decelerating from the same initial velocity over a shorter distance). This may result in an increase in force measurement for each impact. A maximum force for a given impact energy may be when the cup P can no longer overcome, responsive to a given impact force from the actuating system, the resistive (e.g., static friction) forces from the surrounding bone. This results in a "plateau", where any subsequent impact will not change either the insertion of cup P or the force measured.

In some embodiments, this relationship may be used to "walk up" the insertion force plot, allowing tool 1600 to find the "plateau" of larger and larger impact energies. By increasing the energy, the relationship between measured impact force and cup insertion should hold until the system reaches a non-linear insertion force regime. When the non-linear regime is reached, a small linear increase in impact energy will not overcome the higher static forces needed to continue to insert the cup. This will result in an almost immediate steady state for the measured impact force (mIF of a force application X is about the same as MIF of a force application X+1).

A procedure for automated impact control/force measurement may include: a) Begin operation of an insertion agency with a static, low energy; b) Record the measured force response (MIF); c) continue operation of the insertion agency until the difference in measured impact force approaches zero (dMIF=>0), inferring that the cup is no longer displacing; d) increase the energy of the operation of the insertion agency by a known, relatively small amount; and e) repeat operation of the modified insertion agency until plateau and increasing energy in a fashion (e.g., a linear manner) until a particular plateau patterning is detected. Instead, an increase in energy results in a "step function" in recorded forces, with an immediate steady-state. The user could be notified of each increase in energy, allowing a decision by the surgeon to increase the resulting impact force.

A goal of a validated ISM concept is to produce a sophisticated tool for a surgeon that provides automatic, intelligent prosthesis installation, with the capacity to provide access to an optimal best fixation short of fracture (BFSF) endpoint inherent in any implant/cavity system. This tool will allow surgeons of all walks of life, regardless of level of experience, to obtain the best possible press fit fixation of any cup/cavity system, without fear of too loose or tight press fit, as well as obviating the need for screw fixation with all its attendant problems.

The tool may include a handheld pneumatic instrument with a sliding mass component. It may have the following features: 1) ability to deliver precisely controlled axial impacts of known impact energy E, 2) ability to increase or modify applied force (F1) over the course of use, 3) ability to acquire the resulting F1, F2, F3, and F5 for each impact, 4) ability to automatically control the application of impact energy to optimally seat an acetabular cup (implant) using the algorithms determined in Phase I, 5) communicate data pertaining to ISM and BFSF to the surgeon, 6) allow for manual override and selection of impact energy by the surgeon.

Actuators of applicator 1605 may include a one or more of a wide variety of devices (or combinations thereof), including pneumatic actuators, electro-magnetic actuators, spring-loaded masses, and the like.

The device may have industry standard interfaces in order to allow for use with a variety of cup models. For the example implementation, the impact energy is controlled through a piston actuation control mechanism and by additional adjustments of sliding mass and travel distance. Once a final actuation method is selected, a working prototype will be designed and fabricated to allow for controlled insertion of acetabulum cups.

The instrument may be equipped with inline force sensors and wireless connectivity in order to determine resulting forces F1, F2, F3, F5 within the system. Applied force F1 and felt force within the tool (F2) will be measured using internal sensors, whereas the forces felt in bone (F5) and at the implant/bone interface (F3) will be measured separately with appropriately placed sensors in the system and the data conveyed to the central processing unit (CPU) through wireless (intranet) systems.

The tool will be controlled by integrated electronics that provide analysis of the inter-relationships between F1, F2, F3, F5 with respect to number of impacts (NOI) to full insertion, and impact energy. The magnitude of the impacts will be controlled by a CPU (FIG. 16) and associated software, where the system control may include a microcontroller in two-way communication with a user interface and receive inputs from a signal conditioner, which receives data (directly or indirectly) from the sensors within the system. The microcontroller will be coupled to the actuator to set a desired impact energy and run a fixation algorithm to obtain endpoint BFSF.

Programmed algorithms based on the binary decision system described in Phase I Specific Aim #1 will produce successive impacts of known energy, making two simultaneous decisions before each impact: 1. Continue applying force or not, and if so, then 2. Increase energy or not. These binary decisions will be based on parametric values produced by the control electronics, which provide essential feedback of the implant/bone interface, and the elastic response of bone at the aperture. The following algorithm provides a basic example of the binary "fixation algorithm" to be incorporated in the control mechanism: (i) apply energy E1 and measure F2, NOI, $\Delta$F2; (ii) monitor F2 over NOI, and/or monitor $\Delta$F2 as it approaches 0; (iii) when $\Delta$F2 approaches 0, insertion is not occurring for that particular energy E1. If NOI required to achieve this point is sufficiently large (low rate of insertion), as determined by the control algorithm, then E1 is increased to E2; (iv) continue steps (i) through (iii) until the NOI required for $\Delta$F2 to approach 0 is sufficiently small (high rate of insertion), as determined by the control algorithm; (v) the sophisticated tool will not generate automated impacts after this level is reached. Additional increase in energy E is not recommended but can be produced manually at the surgeon's discretion. No more than one incremental manual increase is recommended.

As noted earlier, preliminary data indicates that force measurements directly at the interface (F3), and in bone (F5) will show similar trends and characteristics as F2, such that although independent, they may be considered redundant, complimentary and/or cooperative. It is expected to be able to incorporate these data into an independent system architecture and utilize existing data fusion algorithms to potentially produce a higher resolution evaluation of the stress (force) field around the implant/bone interface than with each individual sensor alone.

Validation of the tool will be performed at Excelen and at the University of Minnesota Department of Engineering by comparing the quality of insertion (extractive force F4) produced by AI-PID—which automatically achieves endpoint BFSF—with the quality produced by a mallet and standard impaction techniques accomplished by a board certified orthopedic surgeon blinded to the study. Specifically, the two distinct endpoints of 1. BFSF (achieved through AI-PID) and 2. Full Seating (achieved through mallet strikes) will be compared to determine differences in F4 and fracture incidence. All parameters associated with these two endpoints will be compared and evaluated. Specifically, a risk benefit analysis will be performed to determine whether higher impact energies were required to obtain full seating, and if so, whether the additional impacts provided any significant value as to CI or F4, and whether there was any increase in fracture incidence (failure of the cavity) with either technique.

Interpretation of Results:

Measurements of F2 and ΔF2 and their first and second order derivatives and comparative analysis with respect to NOI to insertion may provide a principled and organized process for application of energy to achieve the desired optimal endpoint BFSF. It is anticipated that the second order relationship of ΔF2 to NOI, alternatively stated as the rate of decay of ΔF2 (how fast ΔF2 approaches 0) may provide an evaluation of elastic/plastic deformation and also contribute to achieving BFSF.

Figure 17:
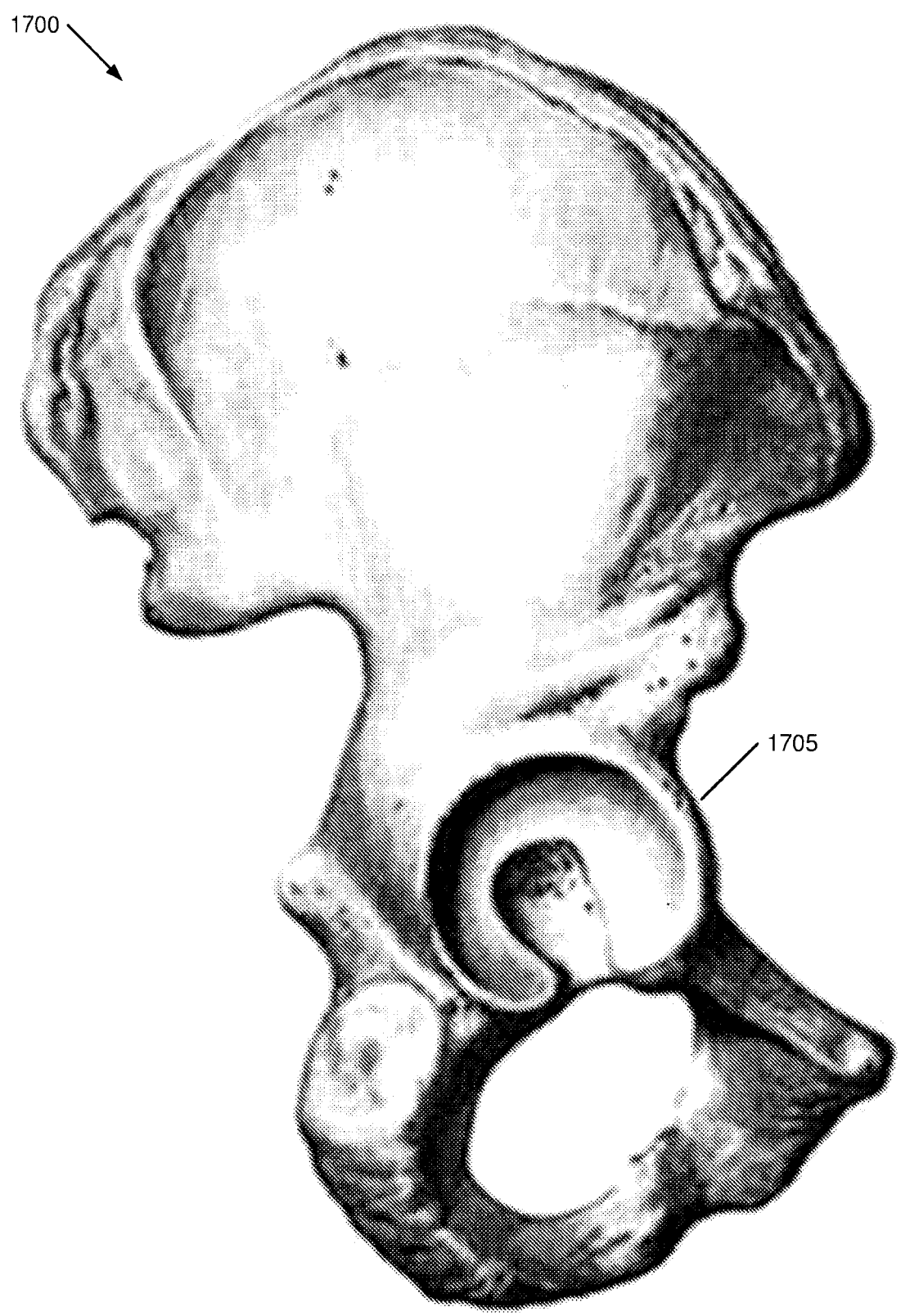
FIG. 17 illustrates a pelvis defining a non-hemispheric acetabulum.

FIG. 17 illustrates a pelvis 1700 defining a non-hemispheric acetabulum 1705. In conventional primary (non-revision) hip replacement, acetabulum 1705 is prepared using a hemispherical reamer and the acetabular cup is installed into the prepared cavity. The acetabular cup conventionally includes a circular perimeter about the opening and may include a hemispherical or elliptical body implanted into the hemispherical cavity. As seen in FIG. 17, acetabulum 1705 includes a much more complex three-dimensional volume with each acetabulum 1705 unique for each person.

Figure 18:
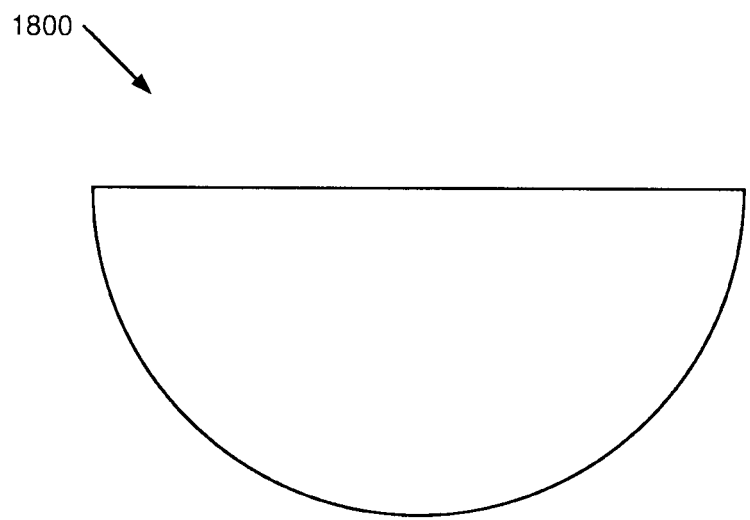
FIG. 18 illustrates a side view of an acetabular cup for an acetabulum.
Figure 19:
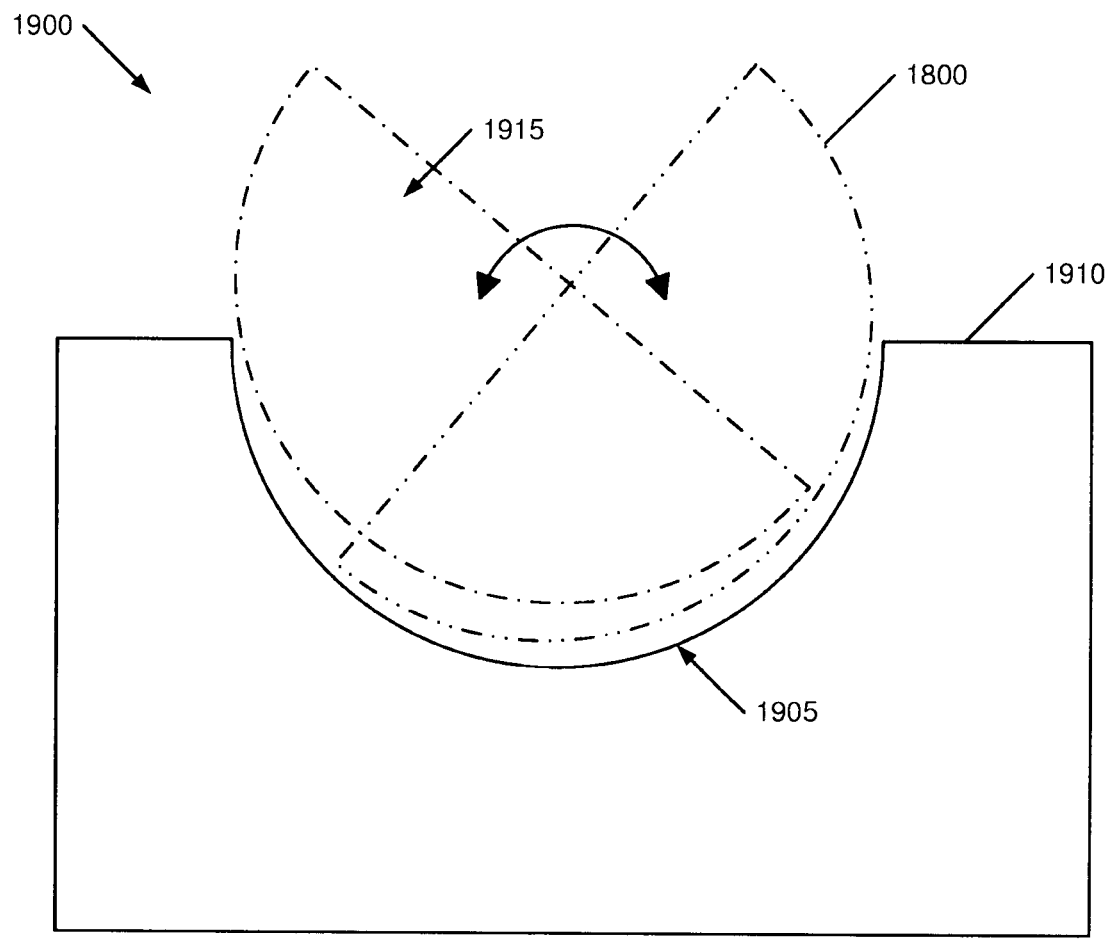
FIG. 19 illustrates a side view of the acetabular cup installed into a hemispherically-reamed cavity in the acetabulum.

FIG. 18 illustrates a side view of a hemispherical acetabular cup 1800 for a hemispherically-prepared cavity commonly used in conventional complete hip replacement surgery. FIG. 19 illustrates a side view of a hip replacement 1900 with acetabular cup 1800 installed into a hemispherically-reamed cavity 1905 reamed in a portion of acetabulum 1910.

Installation of cup 1800 into cavity 1905 requires that cup 1800 is installed to the proper depth with a proper three-dimensional orientation of an opening 1915 with respect to acetabulum 1910. Many risks to the patient may be traced to consequences associated with hip replacement 1900.

Figure 20:
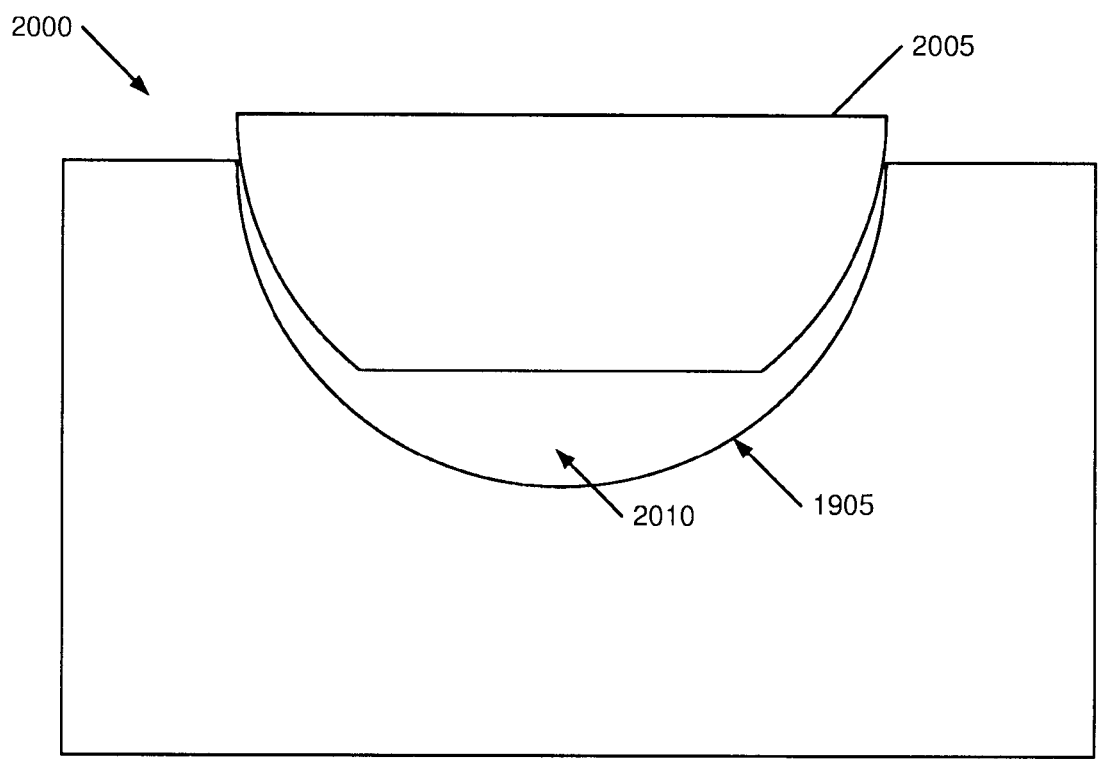
FIG. 20 illustrates a side view of an installation of a snubbed acetabular cup from FIG. 15 installed into the hemispherically-reamed cavity.

FIG. 20 illustrates a side view of an installation of a hip replacement 2000 using a snubbed acetabular cup 2005 corresponding to one of the embodiments illustrated in FIG. 15 installed into hemispherically-reamed cavity 1905. As described herein and in some of the incorporated patent applications, one goal of installation of cup 2005 is to avoid bottoming out to allow maximizing fixation of cup 2005 short of fracture. Cup 2005 installed into cavity 1905 may result in a void 2010 proximate a polar apex of cup 2005. In some cases it may be desirable to reduce a volume of void 2010.

Figure 21:
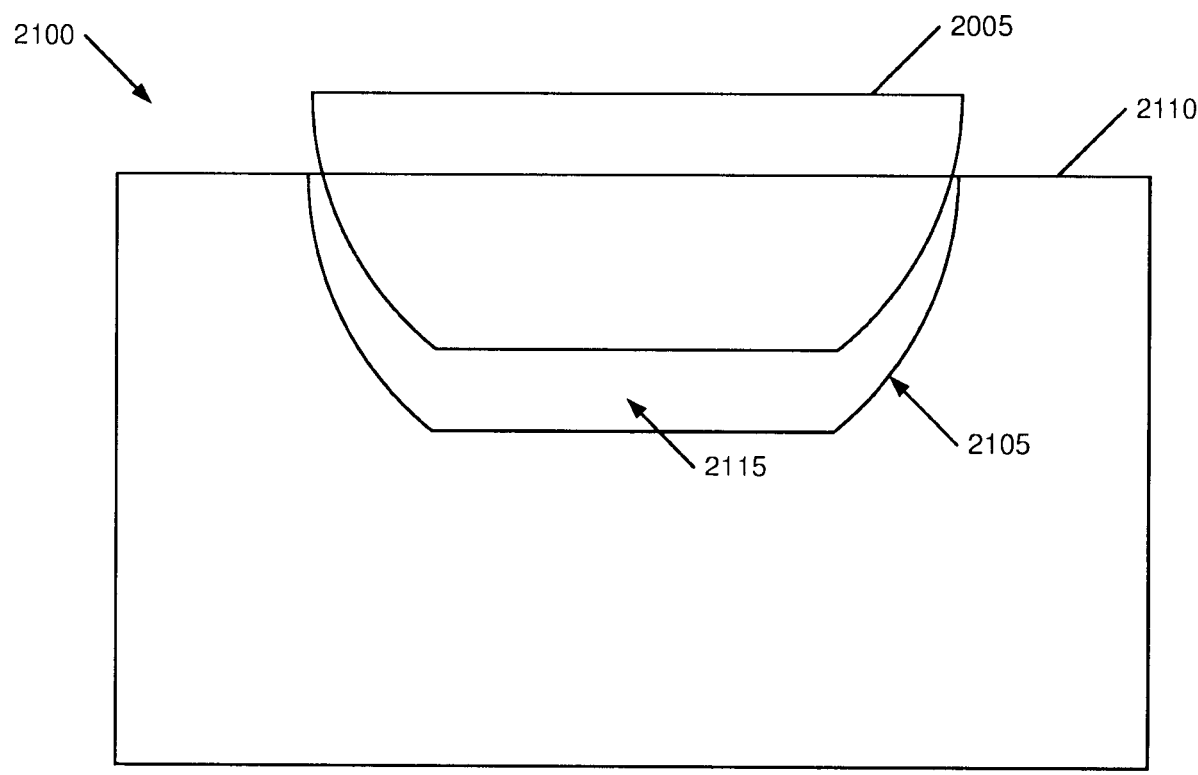
FIG. 21 illustrates a side view of an installation of the snubbed acetabular cup installed into a snub-prepared or sculpted cavity in the acetabulum.

FIG. 21 illustrates a side view of an installation of a hip replacement 2100 using snubbed acetabular cup 2005 installed into a snubbed cavity 2105 in acetabulum 2110. Cup 2005 installed into cavity 2105 has a reduced volume for a void 2115. Cavity 2105 may be prepared in several ways including use of a snub-nosed reamer or use of a bone sculpting tool as further described herein, for example, illustrated in FIG. 32 and FIG. 33 and in the associated text.

Figure 22:
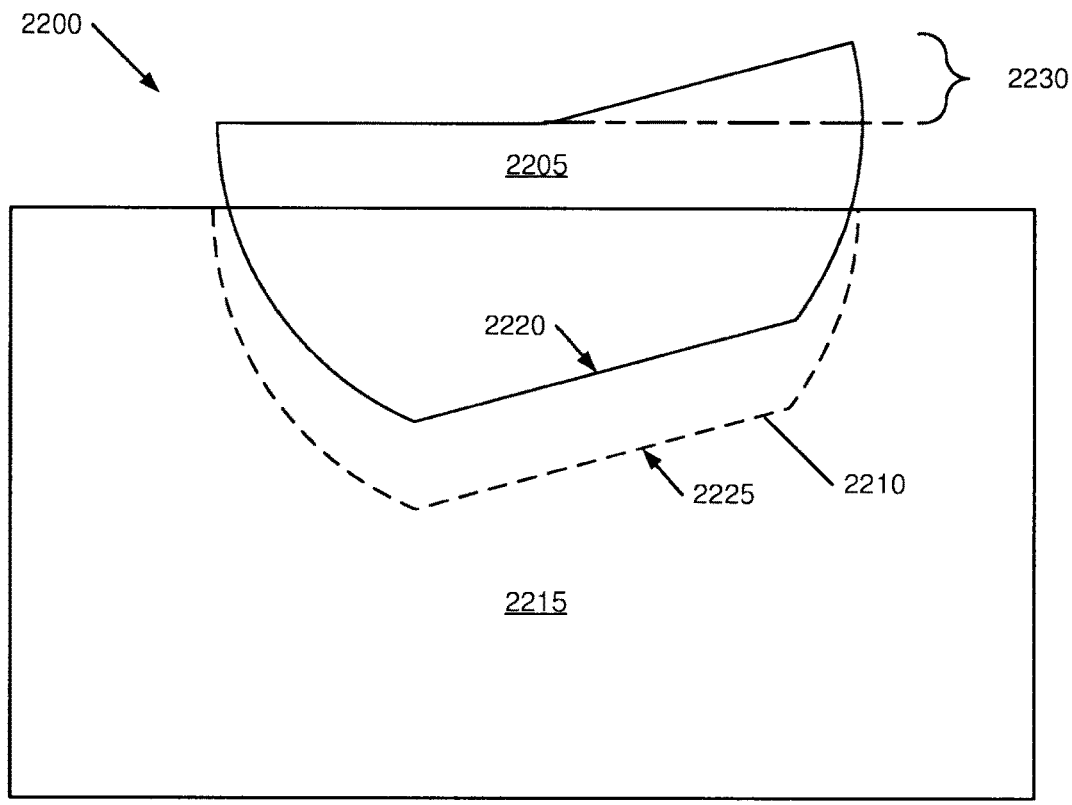
FIG. 22 illustrates a side view of a first embodiment for an orientation-keyed custom implant installed into a snub-prepared or sculpted cavity in the acetabulum.
Figure 23:
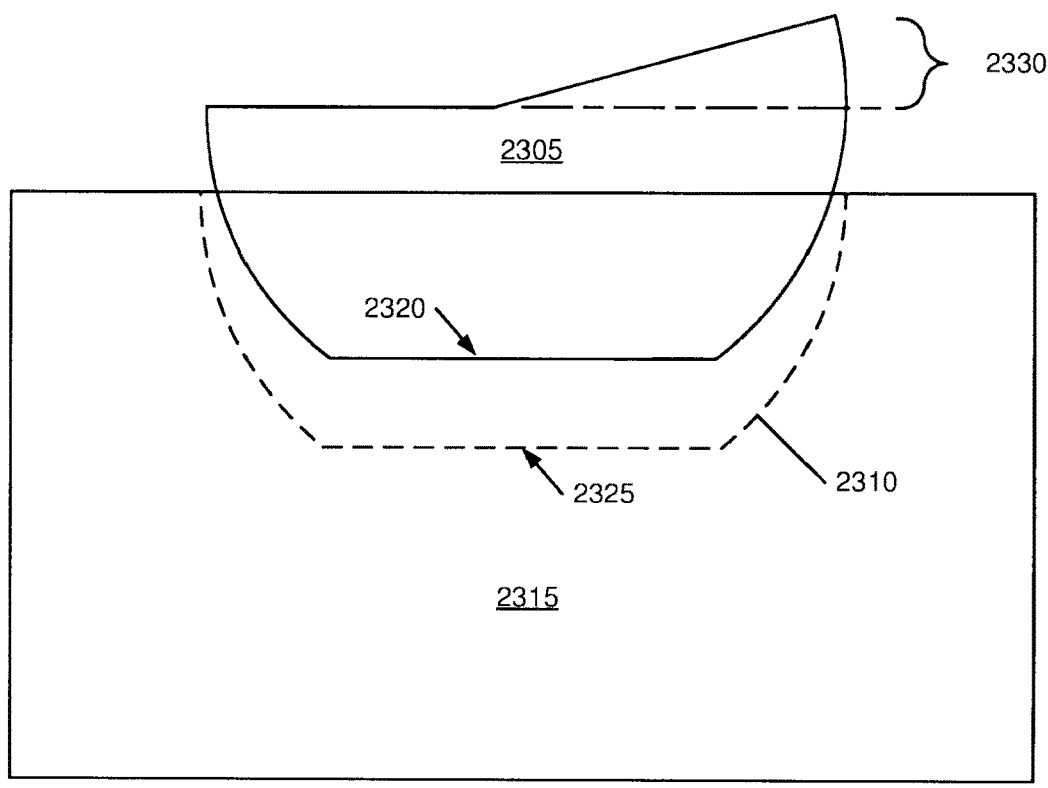
FIG. 23 illustrates a side view of a second embodiment for an orientation-keyed custom implant installed into a snub-prepared or sculpted cavity in the acetabulum.

FIG. 22 illustrates a side view of an installation of a hip replacement 2200 using a first embodiment for an orientation-keyed implant 2205 (e.g., custom acetabular cup) installed into a special snub-prepared or sculpted cavity 2210 in acetabulum 2215. FIG. 23 illustrates a side view of an installation of a hip replacement 2300 using a second embodiment for an orientation-keyed implant 2305 (e.g., custom acetabular cup) installed into a special snub-prepared or sculpted cavity 2310 in acetabulum 2315.

As noted herein, one challenge associated with installation of an acetabular cup into a prepared cavity in an acetabulum is to achieve a desired post-operative orientation. Generally, implant orientation may include variables in cup position such as depth, height, and angular position (anteversion and inclination/abduction—e.g., 41° inclination and 16° anteversion). An interaction of a special orientation-keyed implant within a specially prepared cavity may be used to help achieve the desired post-operative orientation. Either the cavity or the implant (or in more complex implementations both cavity and implant) may be produced so that the desired orientation is achieved when the complementary keyed components are mated together (e.g., keyed implant installed in complementarily keyed cavity).

Implant 2205 may be a standard implant having a pre-configured keying surface 2220 that properly orients implant 2205 when interacting with a custom orientation surface 2225 prepared in acetabulum 2215, upon installation of implant 2205 within cavity 2210. In hip replacement 2200, particular attention is used in preparation of cavity 2210 with the correct positioning of orientation surface 2225. The preparation is informed by a predetermined orientation of keying surface 2220.

In contrast, implant 2305 may be a custom implant have a custom keying surface 2320 that properly orients implant 2305 when interacting with a "standard" orientation surface 2325 prepared in acetabulum 2315. In hip replacement 2300, particular attention is used in preparation of implant 2305 (e.g., a special additive manufacturing process to produce the implant) with the correct orientation of keying surface 2320. The preparation of keying surface 2320 is informed by a predetermined orientation of standard orientation surface 2325.

In these examples, either the implants are provided with a standard custom surface and the cavity orientation surface is customized to achieve the desired final orientation of the implant when installed in the prepared cavity or the cavities are provided with a standard orientation surface and the keying surface of each implant is customized as desired or needed for the particular installation.

Particularly with use of a sculpting tool, and further particularly when combined with custom produced primary implants, a total hip arthroplasty may include a very wide variety of options to allow a surgeon to achieve optimal desired installations for each patient.

For example, cup 2205 may include a portion 2230 that extends above acetabulum 2215 when properly installed and similarly cup 2305 may include a portion 2330 that extends above acetabulum 2315 when properly installed. These above-acetabulum portions are provided in order to enhance stability of the hip articulation, for example to prevent anterior and posterior hip dislocations.

Figure 24:
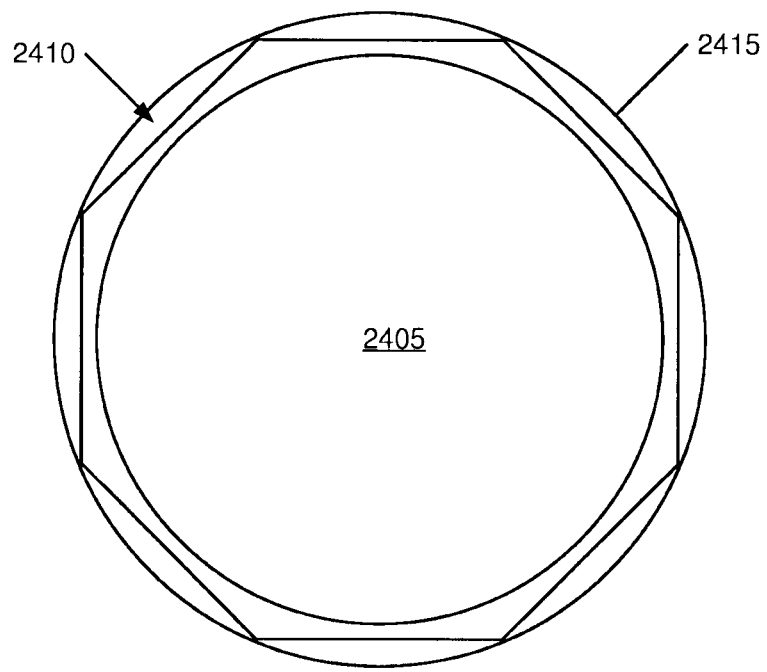
FIG. 24 illustrates a top view of a multi-vertex acetabular cup from FIG. 15 installed into a cavity having a circular perimeter.
Figure 25:
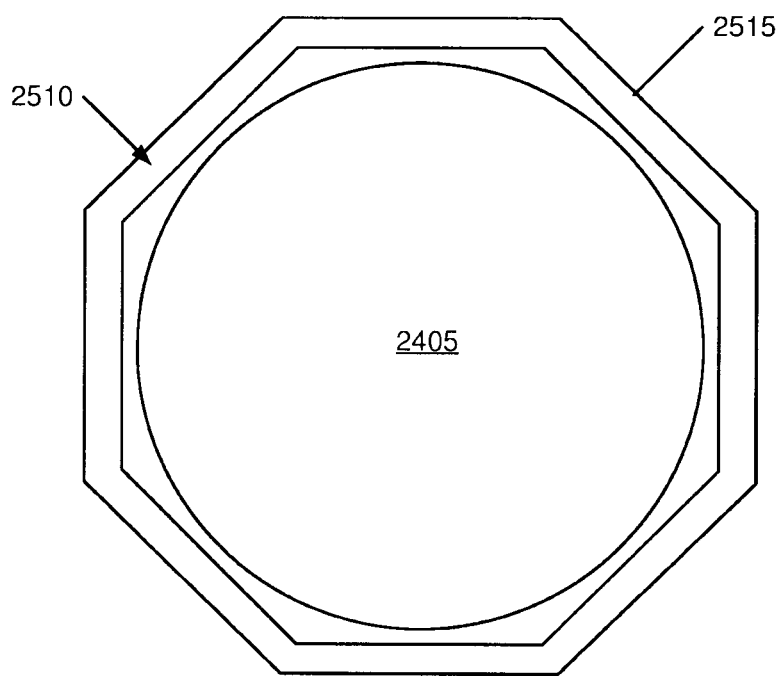
FIG. 25 illustrates a top view of the multi-vertex acetabular cup from FIG. 24 installed into a multi-vertex sculpted cavity in the acetabulum.

FIG. 24 illustrates a top view of a multi-vertex acetabular cup 2405 from FIG. 15 installed into a cavity 2410 having a circular perimeter 2415 and FIG. 25 illustrates a top view of multi-vertex acetabular cup 2405 installed into a multi-vertex sculpted cavity 2505. FIG. 25 illustrates that at least some portion of any orientation keying may be achieved by custom keyed complementary perimeters of an implant and an opening at an installation site. Not shown explicitly but some embodiments may include a unique perimeter keying feature such that the implant may be inserted into the cavity in a limited number of ways (e.g., a single unique orientation).

Figure 26:
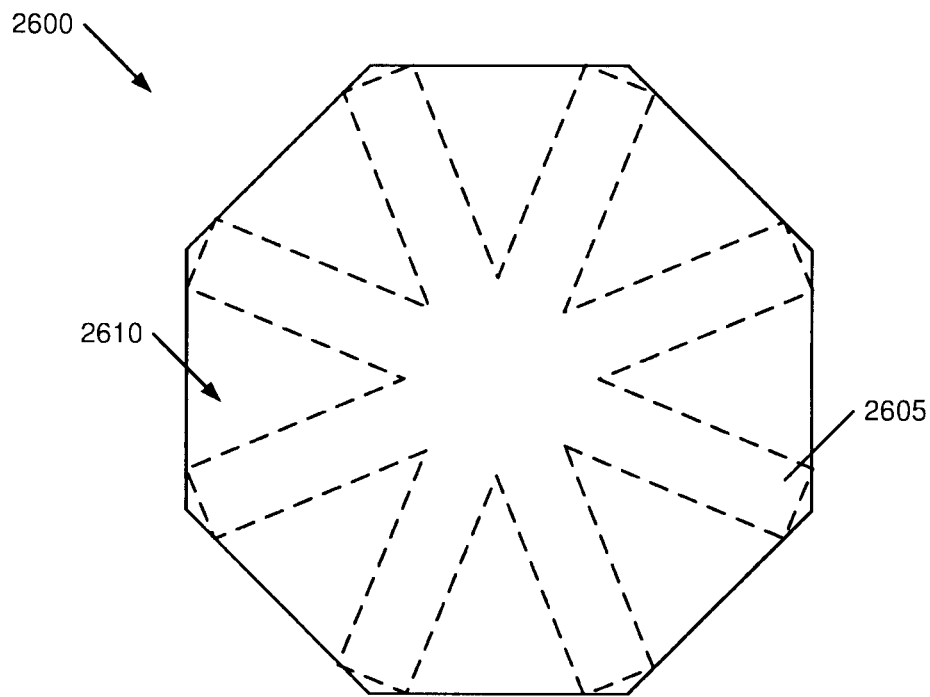
FIG. 26 illustrates a top view of the multi-vertex sculpted cavity without an implant installed.
Figure 27:
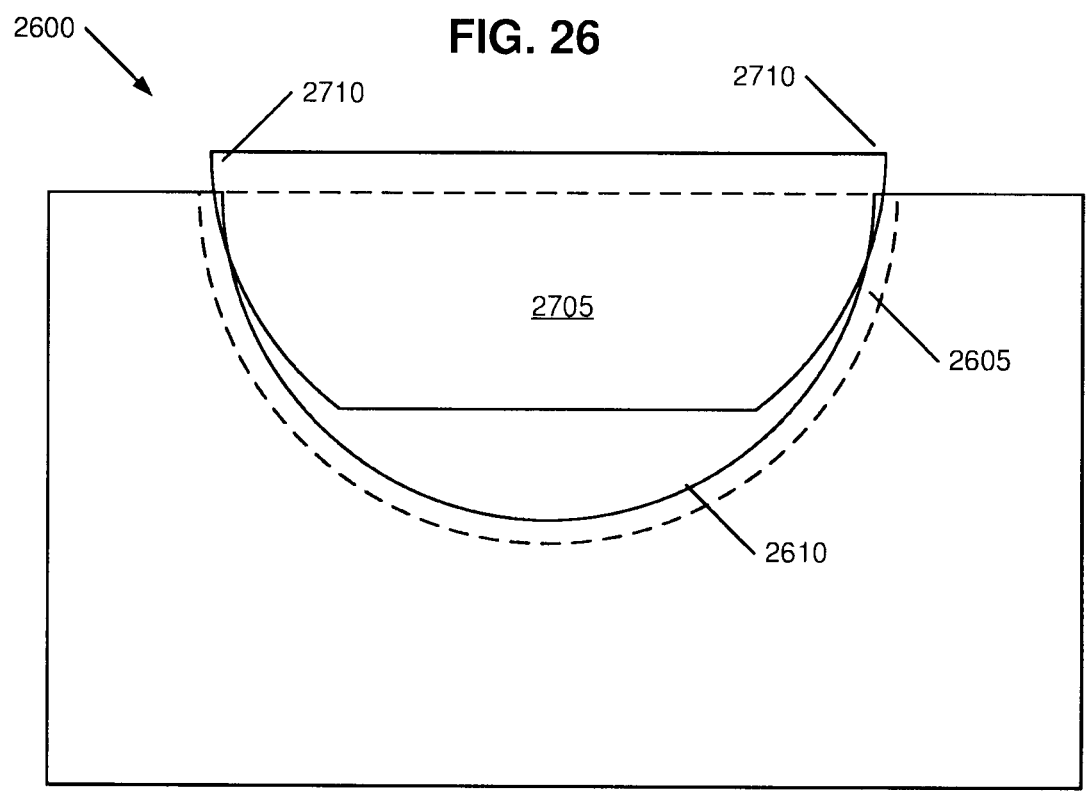
FIG. 27 illustrates a side view of the multi-vertex sculpted cavity receiving a multi-vertex acetabular cup.

FIG. 26 illustrates a top view of an alternate multi-vertex sculpted cavity 2600 without an implant installed, and FIG. 27 illustrates a side section view of multi-vertex sculpted cavity 2600 receiving a multi-vertex acetabular cup 2705. Cavity 2600 includes one or more channels 2605 prepared within an interior surface 2610 of cavity 2600.

In FIG. 26, cavity 2600 is prepared for receipt of a regular octagonally-prepared perimeter (e.g., eight vertices 2710) there are eight channels 2605, though any particular implementation may include a greater or lesser number of channels 2605 as vertices of an intended implant. As illustrated, channels 2605 completely span interior surface 2610 from an edge to a center. These channels may serve a number of purposes to aid a surgeon in treatment options and implant installation. A particular configuration of channels 2605 may be determined based upon its intended use.

In some cases, during installation of an implant, the insertion and orientation tools may cause an implant to skid or shift during processing. Vertex/channel interactions may reduce or eliminate such skidding or shifting, and as well, allow exact desired alignment of the implant to be coded within the implant and the prepared bone channels.

In some cases, as discussed elsewhere herein, the surgeon often spends significant resources in installing, measuring, reorienting, repeating, until the surgeon concludes the operation. Properly sculpted channels interacting with the vertices of a multi-vertex implant may provide some installation keying (e.g., implant orientation) during installation to reduce some of the resources expended in installation and it may also reduce risks of improper or unintended installation/orientation.

In some implementations, the channel/vertex keying is configured for a unique solution that may set the implant at the intended orientation once installed. When there is a unique solution, there is only one outcome from the installation, which desirably includes orientation of the implant at the intended/desired orientation. For example, the surgeon may want the acetabular implant to be positioned exactly (not generally or approximately) at 43° of inclination and 17° of abduction. This level of accuracy and precision is able to be accomplished when the desired alignment information is embedded in the angularity provided by the vertex/channel interaction of the implant and prepared bone, where when the vertices of the implant precisely fit the channels of the prepared bone, one can be assured that the pre-operatively planned alignment has been precisely achieved.

An otherwise hemispherical acetabular cup may include one or more orientation structures fixed to an exterior surface to be used with a set of cavity channels as an alternative to keying vertices. Thus these exterior keying structures may be used with a wide variety of implants and not just multi-vertex implants. Not all the vertices and/or orientation keying structures are required to be used for orientation (e.g., other vertices may be present without channels or channels may be present without corresponding vertices) such as for configuring a propensity for installation as discussed herein.

Figure 30:
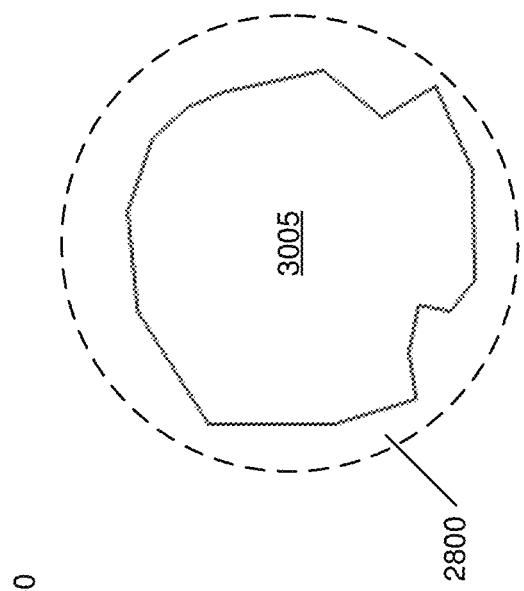
FIG. 28-FIG. 30 illustrate top views of a set of prepared acetabular cavity openings.
Figure 29:
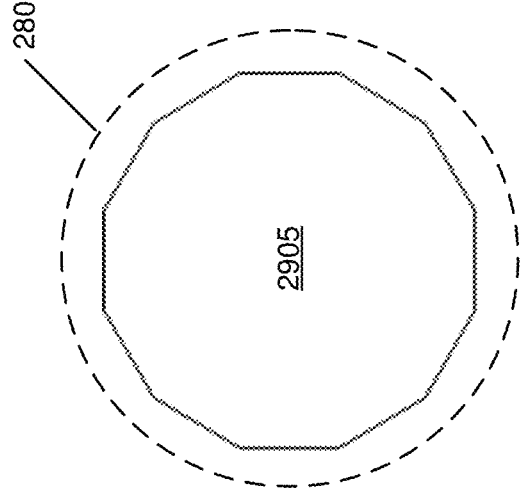
Figure 28:
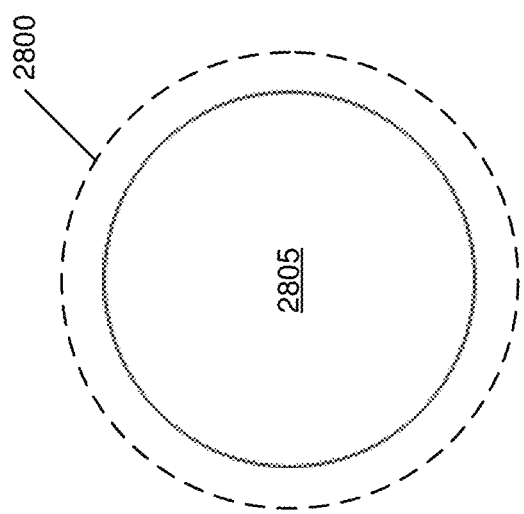

FIG. 28-FIG. 30 illustrate top views of a set of prepared acetabular cavity openings depicting another benefit that may be associated with custom sculpting of an implant installation site in contrast to a conventional hemispherical reaming. In these figures a conventional reamed circular opening 2800 is included for comparison. FIG. 28 illustrates a top view of a conventionally-reamed circular acetabular cavity opening 2805 for receipt of an implant having a circular perimeter opening; FIG. 29 illustrates a top view of a regular polygonal custom-sculpted acetabular cavity opening 2905; and FIG. 30 illustrates a top view of an irregular polygonal custom-sculpted acetabular cavity opening 3005. When the implant includes an acetabular cup, all the implants include an arcuate interior surface volume for receipt of a complementary ball (femoral head) component of a corresponding prosthesis used with the implant. The exterior surface volume of these customized implants however may be produced with virtually any desired or necessary format while preserving the arcuate interior surface volume. A comparison of circularly reamed cavity opening 2805 to irregularly sculpted cavity opening 3005 illustrates that the sculpting process may result in removal of less bone and tissue which is preferable as it is offers less trauma which may improve healing.

Figure 31:
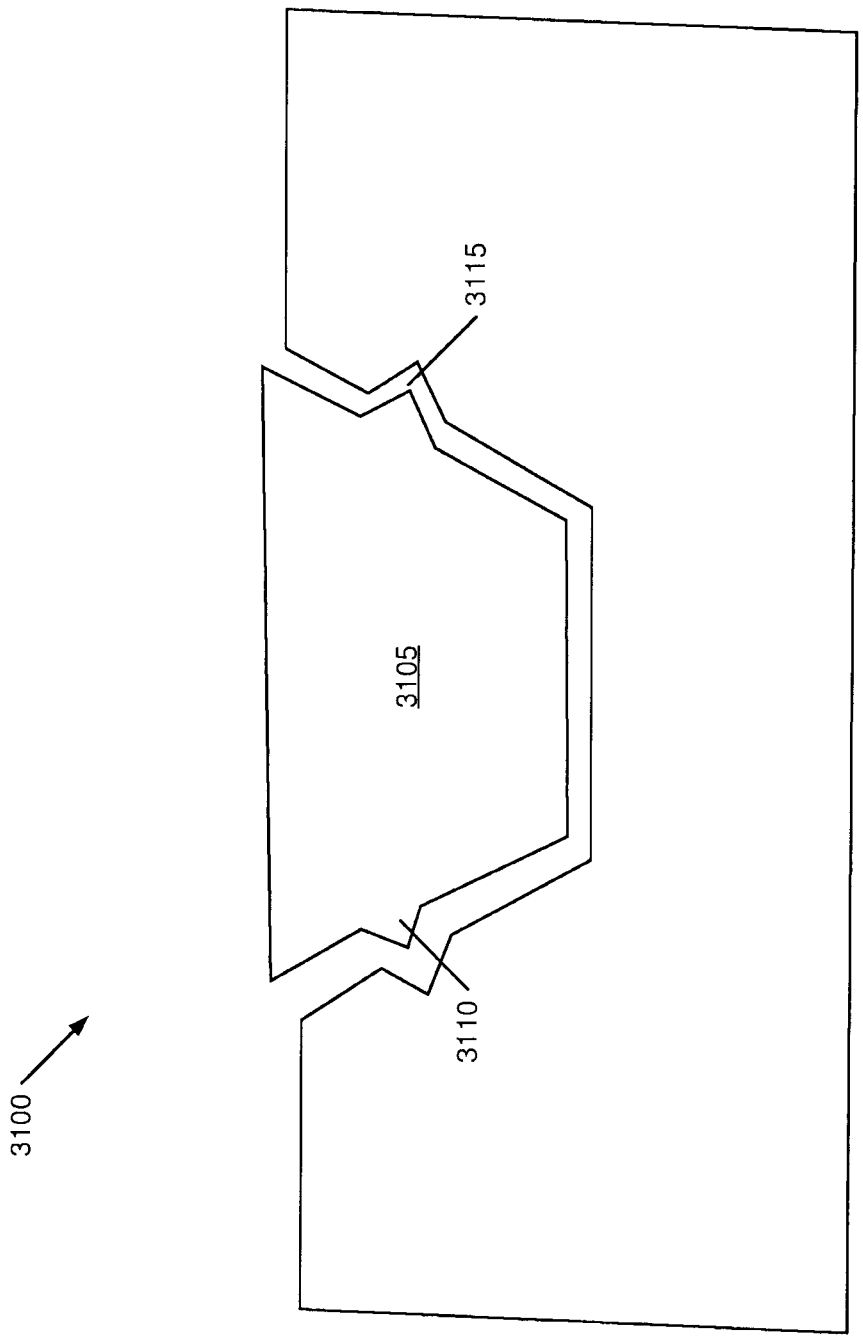
FIG. 31 illustrates a side view of a set of complementary dimples and fasteners in an implant system.

FIG. 31 illustrates a side view of an implant system 3100 including a sculpted cavity 3105 using a set of fasteners 3110 and complementary dimples 3115. The sculpting tool may form dimples in the cavity (or less desirably in an exterior surface of the implant) to aid with orientation keying. The set of dimples and fasteners may also, or alternatively, serve another function of providing an indication to the surgeon to register that the implant has been inserted to the desired depth at the desired orientation. Bone at an installation site has some elasticity and the implant will "snap" into position when the set of dimples and complementary fasteners engage during installation.

As discussed herein, realtime ISM (invasive sensing measurement) may monitor an installation force while the implant is being installed. One goal of this ISM to help install the implant with the best (interference fit–press fit) fixation short of fracture "BFSF" (within a "B" cloud).

Figure 32:
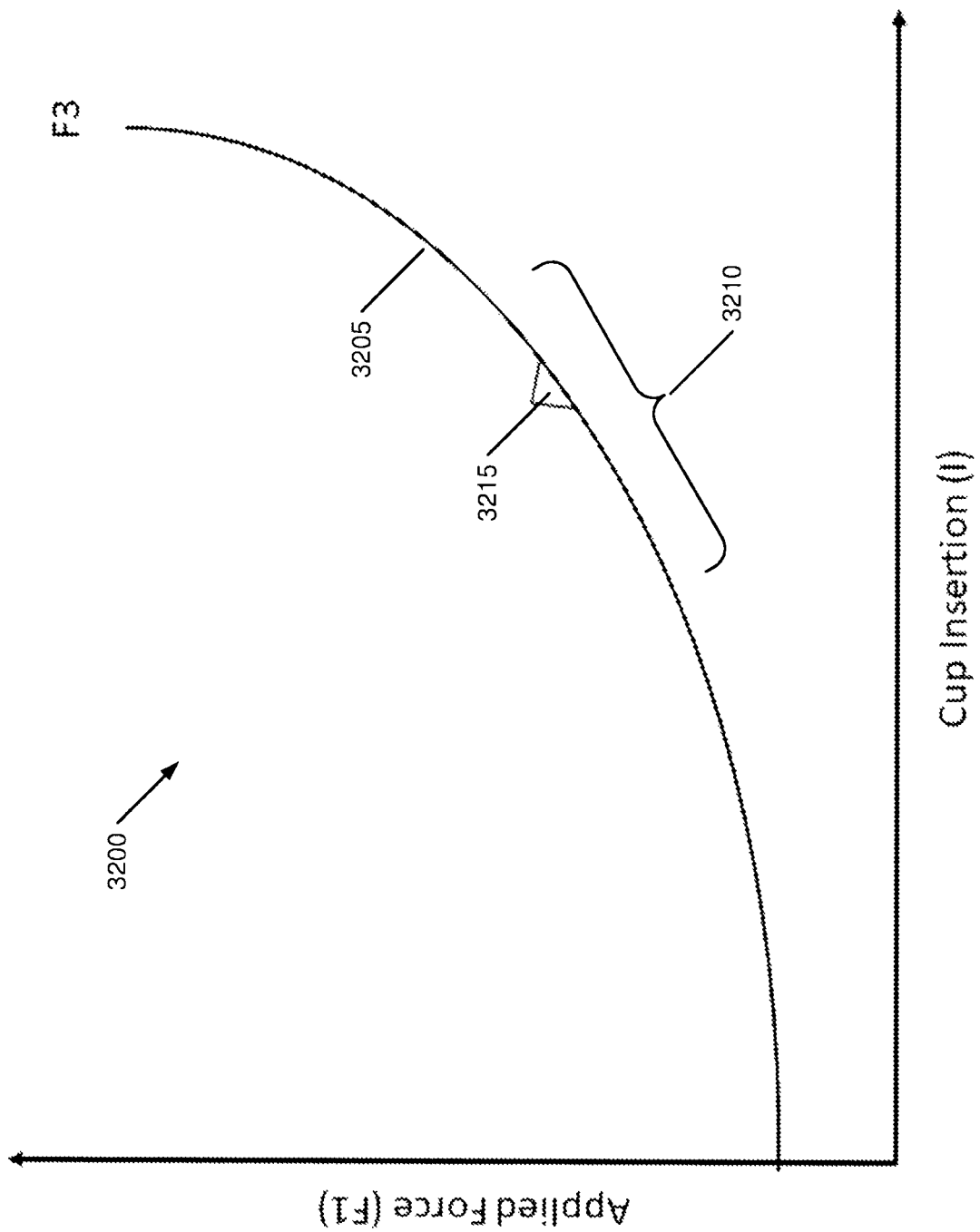
FIG. 32 illustrates an embodiment of an invasive sense measurement chart including a response to a use of the implant system of FIG. 31.

FIG. 32 illustrates an embodiment of an invasive sense measurement chart 3200 including an ISM response 3205 during use of implant system 3100. A goal of the installation, particularly using an ISM embodiment, is to install the implant into the installation site to achieve a best fixation short of fracture (BFSF). A B-cloud 3210 may provide a target region response 3205 to be reasonably close to the BFSF goal. With the set of dimples and complementary fasteners, the ISM response is modified by inclusion of a force spike 3215 responsive to the contact and engagement of the dimples and fasteners.

Spike 3215 may be a check to evaluate the installation of the implant. In some embodiments, it may be the case that it is possible to determine a placement of dimples and fasteners to ensure that the installation is in the B-cloud. Alternatively, or in addition, it may be possible to determine a desired position of the implant at the implant site and use of the fasteners/dimples to mark that desired position (e.g., depth and/or orientation). The surgeon may use the ISM system to independently gauge the BFSF during installation. The surgeon may encounter spike 3215 during the ISM and determine whether the spike 3215 (reflective of reaching an intended installation goal) is in fact in the B-cloud. In an event that spike 3215 occurs in B-cloud 3210, this information could be used to confirm the pre-operative plan and its execution. When spike 3215 occurs outside B-cloud 3210, the surgeon may reassess and reevaluate the installation process and/or the pre-operative plan as this event may indicate an increased risk of some type of failure of the installation.

Figure 33:
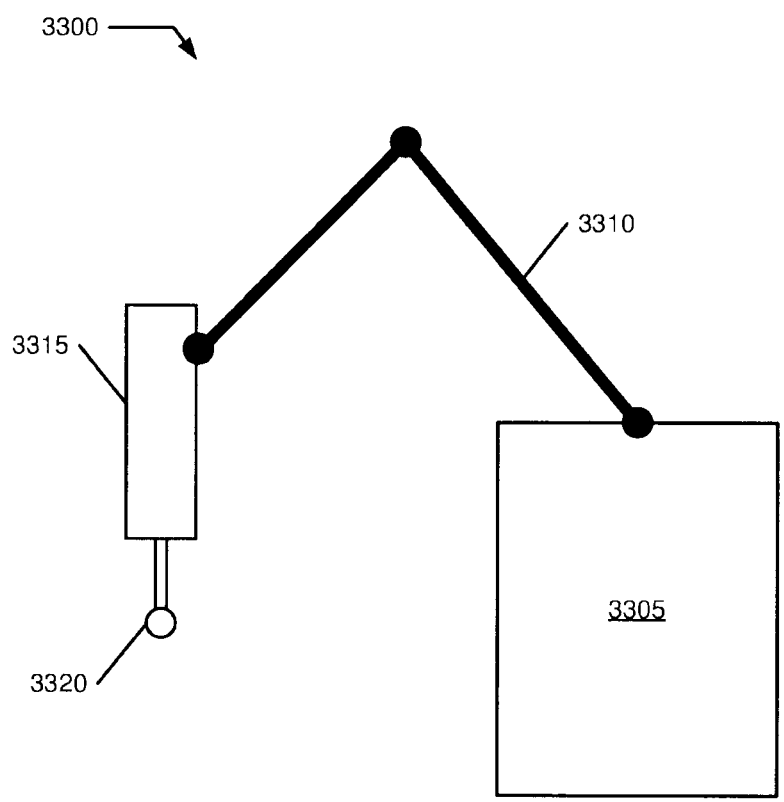
FIG. 33 illustrates a plan diagram of a smart tool robot used as a sculpting implement.

FIG. 33 illustrates a plan diagram of a smart tool robot 3300 which may include a type of three-dimensional bone sculpting tool. Further details of robot 3300 are provided in U.S. patent application Ser. No. 15/398,996 filed 5 Jan. 2017, the contents of which are hereby expressly incorporated by reference thereto in their entirety for all purposes. Robot 3300 includes a controller 3305 coupled to a linkage 3310 which is coupled to a high-efficiency bone preparation tool 3315, with tool 3315 including a bone processing implement 3320. Controller 3305 includes systems and methods for establishing and monitoring a three-dimensional spatial location for implement 3320. Controller 3305 further includes governance systems for linkage 3310. Collectively controller 3305 and linkage 3310 may be a type of constraint, other systems and methods for another type of constraint and providing feedback may be included in some embodiments of the present invention.

Linkage 3310, illustrated as including a mechanically limited articulating arm, is coupled to both controller 3305 and tool 3315. In some cases when processing a particular in-patient bone, controller 3305 may predefine a set of bone regions of the in-patient bone for a processing (e.g., a cutting, a removing, a reaming, a sawing, a broaching, a burring, and the like). Controller 3305 may monitor a relative location of implement 3320 relative to a particular portion of the in-patient bone to be processed and compare that particular portion with the predefined regions. Those predefined regions may include a first subset of regions to be processed by implement 3320 and in some cases also include (or alternatively substitute for the first subset) a second subset of regions not to be processed by implement 3320. Controller 3305 provides a realtime feedback to the user regarding an appropriateness or desirability of processing each the particular portion of bone at the location of implement 3320.

In some cases, the realtime feedback may include a realtime haptic signal imparted from controller 3305 through linkage 3310 to tool 3315. That haptic signal may be of sufficient strength to significantly restrict an ability of an operator to casually move implement 3320 to a region of the in-patient bone that is not to be processed, and some cases may essentially prevent or inhibit the locating of implement 3320 to those regions of the in-patient that are not to be processed.

Other feedback signals may be included in addition, or in lieu of, the haptic system. Audio feedback may in some cases be sufficient to provide feedback to an operator.

Tool 3315 may be an embodiment of an ultrasonically enhanced bone preparation tool which operates implement 3320. Tool 3315 includes a motive system that operates implement 3320 with a bone processing motion. The bone processing motion includes a primary motion having a primary freedom of motion (e.g., for a burr as illustrated, the primary motion may include a rotation about a longitudinal axis, this primary motion having a freedom of motion that includes the rotation about the longitudinal axis). The bone processing motion includes a secondary motion having a secondary freedom of motion, the secondary freedom of motion different from the first freedom of motion. The secondary motion includes an ultrasonic vibratory motion that enhances the bone-preparation of implement 3320 than would be the case of the primary motion alone.

Different implements and tools may include varying primary and secondary motions, there generally being six freedom of motion possibilities for the primary or secondary motions: x, y, and z translations and rotations about any of the x, y, and z axes. Typically the primary motion will include a repetitive (and sometimes reciprocating) component.

An operator grips tool 3315 and manipulates it by hand. Controller 3305 automatically monitors these manipulations to establish a relative location of implement 3320 with respect to a particular portion of an in-patient bone. Comparison of the relative location to predetermined/premapped regions of the in-patient bone that identify processable/non-processable regions results in controller 3320 is used to provide appropriate realtime feedback signals to the operator for each particular portion of bone.

Figure 34:
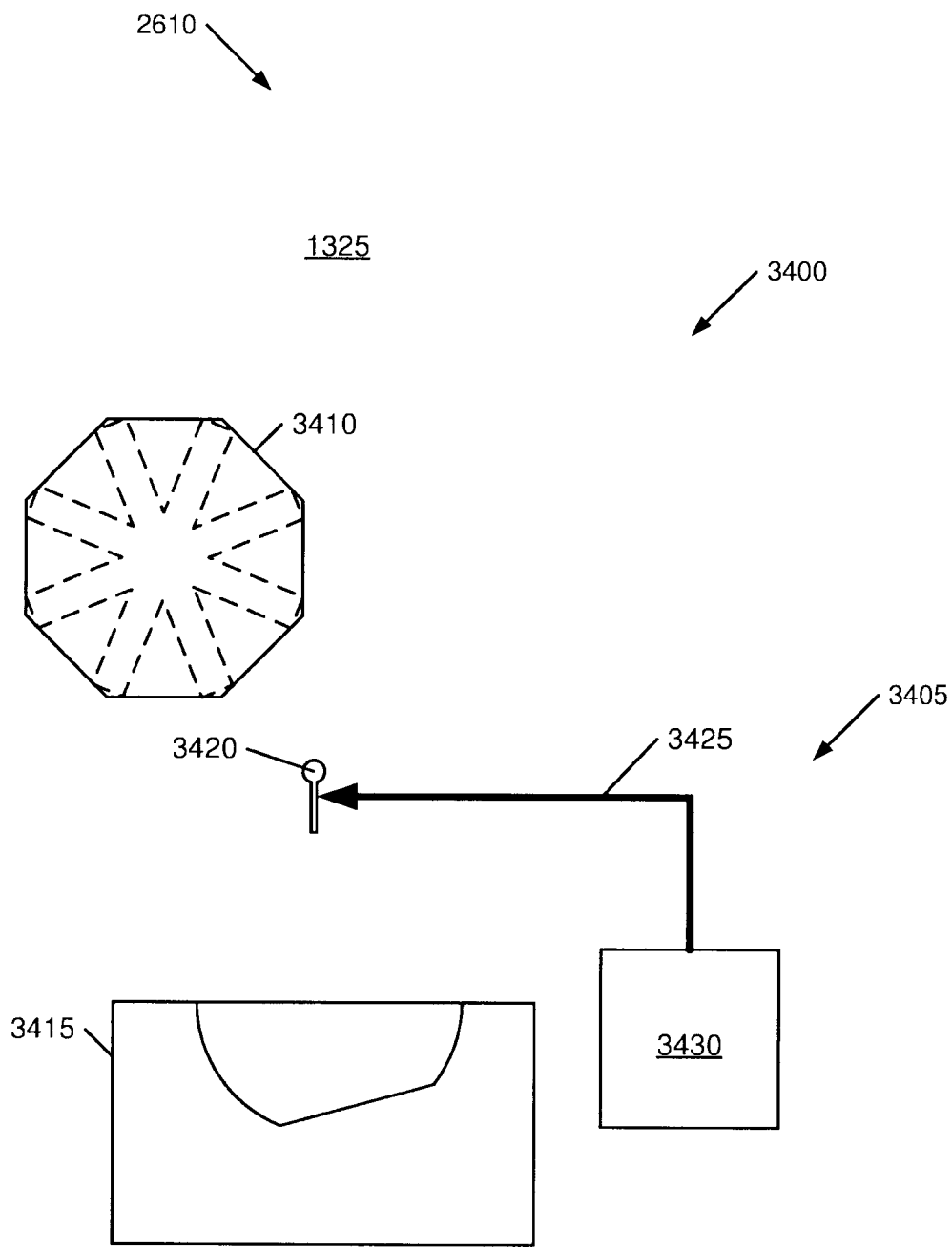
FIG. 34 illustrates a preparation of a set of sculpted bone cavities and attendant orientation structures as described herein by an automated surgical apparatus such as the smart tool robot of FIG. 33.

FIG. 34 illustrates an application of a bone sculpting system 3400 using an implementation of smart tool robot 3300 for preparation of one or more of the special sculpted cavities, cavity features, and implant structures described herein. System 3400 includes an automated/semi-autonomous cavity sculpting apparatus 3405 for a preparation of a sculpted cavity, and attendant structures. In FIG. 34, apparatus 3405 may produce a first sculpted cavity 3410 in a portion of an acetabulum and/or may produce a second sculpted cavity 3415 in another acetabulum. Apparatus 3405 includes a bone preparation implement 3420 having a mechanical coupling 3425 (direct or indirect) coupling implement 3420 to a controller 3430 (e.g., a stored program computing system including processor executing instructions from a memory including a user interface to set user options and parameters and sculpting parameters).

There are automated assistive surgical devices which may partially fill the role of apparatus 3405, such as robotic assisted surgical platforms (e.g., MAKO, da Vinci, Verb, Medtronic, TransEnterix, Titan Medical systems, NAVIO blue belt, and the like). These platforms provide positional control/limitation of surgical implements operated by a surgeon, such that the robotic tools (some of which utilize custom software and CT data) resist the movements by the surgeon that may attempt to deviate from a planned procedure, bone preparation, sculpting operation, or other processing. These platforms are often installed into a known reference frame shared by the patient so precise position control/limitation may be imposed. Installing bone preparation implement 3420 (e.g., a high speed rotating burr or the like) the surgeon may operate the platform to form a precisely sculpted cavity and associated cavity elements as described herein (e.g., first sculpted cavity 3410 or second sculpted cavity 3415). A sculpted cavity may be initiated from a bit-prepared cylindrical precursor cavity and then profiled from there or apparatus 3405 may prepare the entirety of the sculpted cavity. Alternatively, the preparation and fine tuning of the sculpted cavity may occur with various other sources of energy such as laser.

Apparatus 3405 may be used to produce internal ridges, dimples, or other irregularities inside a cavity or other component used in the implant procedure (e.g., a prosthesis or structures illustrated in FIG. 31).

Figure 35:
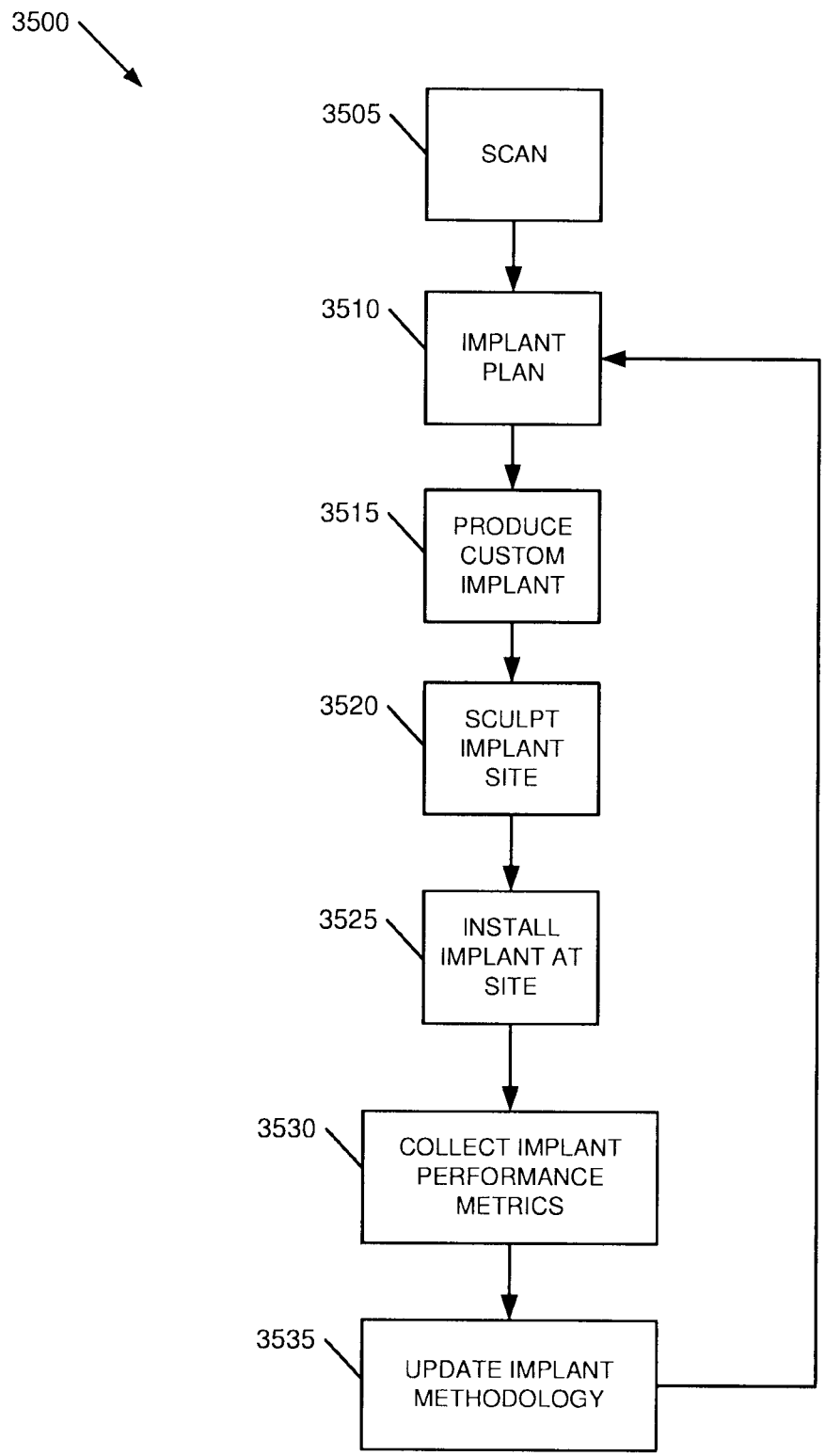
FIG. 35 illustrates a sequence for a series of processes for definition, preparation, installation, and feedback of custom implant installations.

FIG. 35 illustrates a flow chart for a series of processes for definition, preparation, installation, and feedback of custom implant installations, collectively an implant method 3500. Method 3500 includes steps 3505-3535 as follows.

A scan step 3505 images the installation site and patient anatomy to establish parameters for the location, implant, and orientation—X-ray, CT and MRI scans, Access Patient Anatomy for Image based Navigation and Robotics requirements.

An implant plan step 3510 determines a proper size and proper shape of implant, such as by use of virtual templates and other information regarding best practices for the scanned installation site and intended process.

An implant production step 3515 additively manufacture (e.g., three-dimensional printing) a polygonal and/or irregular shaped implant for primary (not revision) total hip replacement.

A sculpt installation site step 3520 may implement the installation plan and sculpt the cavity, keying structures, and other elements. Vertices (angularity) incorporated in an implant functions as a guidance system to key implant in exact desired position; Angularity provides ability to translate positional and alignment information from (CT/MRI/X-ray scans and navigation robotic software) to: (a) bone which is to be sculpted and (b) custom implant to be printed for the planned sculpted cavity. Using haptic robotics and ultrasonic assisted burrs to sculpt the bone cavity creates grooves for polygonal and/or irregular implants. Grooves/channels may confer positional information to bone cavity/implant interaction upon installation. The irregular implant and the prepared bone cavity will precisely match each other's shape. Step 3520 may optionally add dimples and fasteners, such as a stop gap mechanism to allow for a "snap in" sensation when insertion has reached a desired intermediate or final installation milestone. For example, a desired depth and alignment has been achieved, as was preoperatively planned. In some implementations, multiple milestone indicators may be employed to provide installation feedback as successive sets are engaged.

An install implant step 3525 places the custom implant into the sculpted cavity, and any mutually interacting keying and/or indicating structures assist in achieving the implant plan (e.g., a desired depth and orientation).

A collect implant installation/performance metrics step 3530 assesses post-operative implant metrics. Collect Data Base for implant performance associated with different implant alignments. As an example, it would be of great interest to know whether 45° abduction and 20° anteversion produces a better long term performance of the implant than 35° abduction and 15° anteversion. The use of sculpting system and orientation keying structure interaction allow for definition and implementation of a specific implant plan. As the plan data is known along with enhanced confidence that the identified plan was implemented accurately provides increased confidence in the collected metrics that they are associated with specific implant plan parameters. For example, the alignment of (45° abduction and 20° anteversion) commonly desired may be associated with poorer long-term survivorship of the implant (due to variety of factors such as osteolysis, instability, polyethylene wear) than 35° of abduction and 15° of anteversion. The only means of distinguishing the performance difference between specific alignments is through: (i) accumulation of database regarding alignment vs. performance of the implant; (ii) algorithmically building a statistical model based on the dataset. The production of mathematical models can subsequently predict and prescribe the best alignments for a given patient with specific postural conditions. In this manner mathematical modeling can be introduced to enhance implant survivorship.

An update step 3535 aggregates and processes the known implant plans and associated performance metrics to evolve best practices associated with the implant installation, implant plans, and templates used in the implant plans. Compare implant alignment with long term implant performance. Develop data base to provide a basis for introduction of Artificial Intelligence and Machine learning in orthopedics. What has happened=Descriptive Analytics and What will happen=Predictive Analytics and What should be done next=Prescriptive Analytics. Method 3500 includes this quantitative and qualitative feedback to step 3510 (in some cases back to step 3505 when the assessment determines a different or additional imaging paradigm would assist with development and implementation of future implant plans.

Sculpting Summary

A polygonal acetabular cup (implant) with many sides (e.g., a two-dimensional perimeter around an opening and/or a three-dimensional volumetric surface inserted into a prepared cavity at the installation site) can closely estimate the shape of a perfect hemisphere. A polygonal cup also has an advantage of supporting asymmetric stiffness structures (for example, configured for a propensity for insertion such as rib and plank elements or counter-rotating helical elements) due to incorporation of angularity and multiple vertices within its structure. The asymmetric stiffness structures have been previously described for creation of a multi-dimensional asymmetrical stiffness, implementing increased propensity for insertion, and has been described in U.S. patent application Ser. No. 15/406,752 hereby expressly incorporated by reference thereto in its entirety.

A polygonal cup or implant further allows for additional functionalities to be conferred to an acetabular cup or any implant, including reduction of installation force while retaining sufficient pressfit fixation and an addition of positional information and stop gap mechanisms, protecting against micromotion.

Vertices of a virtually planned implant and bone cavity allow for transfer of positional information from (X-ray, MRI, CT scan of robotic and navigational systems) to the bone bed that is to be sculpted and the cup (implant) that is to be additively printed. The vertices of the printed implant and the grooves of the sculpted bone cavity can be created to match each other in a complementary fashion, and therefore collectively translate positional information from robotic and navigational systems directly to the implant and bone. Some embodiments may allow the surgeon to "key" the prosthesis into the bone cavity exactly as preoperatively determined by the computer software. In this manner there is an eliminated or reduced potential for skidding and rotating out of position during impaction.

A polygonal implant additionally has the capacity to "lock" the implant into position. A hemispherical implant can rotate out of desired position in multiple different planes during the impaction process. In addition to having positional information embedded in its structure a polygonal implant will not rotate out of position. The angularity of a polygonal implant provides protection against gross motion during impaction and micromotion with cyclic loading.

It is also well known that the acetabulum, typically considered a hemispherical structure, is not a true hemisphere as illustrated in FIG. 17. The acetabulum is a complex geometric structure made of both cortical and cancellous bone with spring like qualities. The shape of the acetabulum is more like the letter C, or a ⅚ or 300° semicircular structure. Currently CT based and MRI based data is utilized to produce molds of the patient's bone to produce patient specific instrumentation (PSI jigs) which essentially use patient's anatomic data to produce jigs that allow precise cutting of bone.

Image based (CT, MRI, X-rays) robotic systems can produce precise bone cuts through haptically controlled systems. Some embodiments of the present invention may use this same information obtained through X-ray, CT and MRI to additively print implants complementary to the bone cuts produced by these haptic systems.

It is an aspect of some of these embodiments that the implants and the bone cuts of various shapes including hemispheres, oblong shapes, irregular shapes and polygonal shapes can be printed and sculpted, and may include the same information to improve precision and inter-operability.

Polygonal and irregular (angular) implants may have an advantage of including positional information embedded within their structure due to their shape, which contains multiple vertices.

Additionally, since not all acetabular cavities are alike (some are oblong, some are dysplastic, and some have irregular shapes) an irregular and non-spherical cup (implant) can be produced (e.g., additively manufactured), while in a complementary fashion, an irregular bony acetabular cavity can be sculpted.

Further, a concept of complementary implant printing/bone sculpting as described and enabled herein brings forth a possibility of providing tighter and more precise tolerances between the prepared bone and press fit implant. For example, current techniques force the surgeons to under ream the acetabular bone cavity by at least 1 mm to obtain reasonable interference fixation of the implant. Reaming by 0.5 mm is not industry standard nor recommended. Reaming line to line forgoes interference fit fixation and generally relies on screw fixation. As "complementarity techniques" between sculpted bone and printed cup further develop, it is conceivable that the surgeons will desire much tighter tolerances than current (1 mm under ream) techniques allow. With the advent of polygonal and irregular acetabular cups, it maybe undesirable to under-ream the cavity by 1 mm or 2 mm. It may be further advantageous to under-prepare a polygonal and irregular cavity by 0.3 mm or 0.5 mm or 0.75 mm. It is well known that much of the fixation of a press fit implant (metal acetabular cup) occurs at the aperture (rim), which may have mechanical properties that are stiffer and more brittle than the dome of the acetabulum. The capacity to fine tune the rim of the acetabulum (and any other bony cavity) is therefore made possible by the "complementary" custom bone sculpting and implant printing process.

This is a significant innovation since many acetabular bony cavities are deficient with irregular and dysplastic shapes. Current techniques force all acetabular bony cavities to be made into a hemispheres with hemispherical reamers (which can be considered an unnecessary constraint), in order to accommodate a hemispherical cup (the only implant available in the market today for primary hip replacements). This has led to the concept of "Jumbo Cups" which not only destroy significant amount of host bone (see FIG. 30) but also are generally non-anatomic and tend to raise a center of rotation superiorly, adversely affecting musculoskeletal biomechanics of the hip.

A solution to this problem involves production of a customized irregular shaped acetabular cup made in conjunction with a customized and complimentarily prepared bone bed.

Robotic systems can utilize preoperative image-based data to plan precise bone cuts through haptic systems, such as done with the MAKO robot. However, current technology does not allow rapid removal of bone with a burr. It is anticipated that the ultrasonic assisted burrs will add significant capacity to allow rapid and precise removal (sculpting) of bone as discussed in U.S. patent application Ser. No. 16/276,639 filed 15 Feb. 2019 (ultrasonic assisted burr sculpting), the contents of which are hereby expressly incorporated by reference thereto in its entirety for all purposes. Sculpting and irregular cavity production systems may include a stored program computing system including one or more processors executing instructions retrieved from a memory, these systems may include interfaces to control and define operations, these operations may be achieved by execution of instructions using the one or more processors to control other structures such as bone preparation implements (e.g., special burrs or laser systems) to produce the cavities and other goals described, explicitly or implicitly, herein.

Existing robotic haptic technology in combination with ultrasonic assisted burrs (or similar enhanced bone cutting technologies) can rapidly and safely sculpt a bony bed with any proposed irregular shape, slightly under sizing the bony bed for press fit fixation, while a custom irregular cup (implant) is additively printed in advance, slightly relatively oversized (with respect to the intended cavity dimensions) for press fit fixation.

The implant and the bony bed are complementary with grooves within the bony bed matching the vertices of the implant to help implement and constrain a desired orientation for the implant.

Surgeons are typically uncertain as to whether the acetabular cup has achieved the proper seating. Some embodiments may incorporate a concept of Fastener/Dimple to allow the implant (spherical, polygonal or irregular) to "snap into place". This is accomplished with creation of dimples in the bone close to the rim of the acetabulum, and fasteners on the implant that are complementary to the dimples. This construct allows a tactile snapping sensation as the cup is fully inserted to the proper depth.

Current techniques which involve impaction of the hemispherical cups into the acetabulum cannot assure that the obtained alignment of the cup is the same as the desired alignment of the cup because the cup rotates and slides as it is impacted into place (even with haptically controlled robotic systems). The reporting of cup positioning in current literature is stated in "ranges" and not exact numbers. For example, a surgeon maybe happy if the cup is between 35° to 50° of abduction and 10° to 30° of anteversion. Alignments beyond these ranges have higher likely hood of problems including dislocation, polyethylene wear, impingement and osteolysis.

Therefore, there is currently no means to assure EXACT alignment of the acetabular cup in total hip arthroplasty. Furthermore, our only means of measuring cup alignment is with post-operative methods including X-rays and CT scans.

The concept of angularity in customized acetabular cups (polygonal, irregular, spherical) complementarily keyed with customized sculpted bone provides the capability of keying in a prosthesis into exact alignment, or at least allow for significant reduction of gross misorientation or malpositioning.

This capability provides a new era of information gathering for total hip replacement. Until now, any discussion of acetabular cup alignment involved "ranges". With proposed technology, more exact and exact alignments can be achieved. For example, one may want to know what the difference in long term performance of a cup is placed in 45° abduction and 20° anteversion compared to one placed in 35° abduction and 15° anteversion, and many variations of the above question. These questions can now be contemplated because exact implant alignments can now be achieved.

The ability to achieve precise positional alignments of the acetabular cup (or any prosthetic implant utilized in orthopedic surgery) provides ability to produce large data base with regards to cup position and long-term cup performance. Such data base allows cross referencing and comparisons to allow for modeling and abstractions, which in turn allows production of better systems and recommendations. The ability to produce these calculations provides a basis for introducing artificial intelligence and machine learning in orthopedics. If we can know precisely "what has happened" (descriptive analytics) we can anticipate "what will happen" (predictive analytics) which will give us the capacity to determine what we should do next time (prescriptive analytics). Acetabular cup alignment in total hip replacement can significantly benefit from introduction of data analytical processes to enhance long term survivorship of implants.

The following references, expressly incorporated by reference hereto in their entireties for all purposes, support one or more of the concepts or ideas presented herein, including: 1) Udomkiat P, Dorr L D, Wan Z. Cementless hemispheric porous-coated sockets implanted with press-fit technique without screws: average ten-year follow-up. J Bone Joint Surg. 2002; 84A:1195.; 2) Takedani H, Whiteside L A, White S E, et al. The effect of screws and pegs on cementless acetabular fixation. Trans Orthop Res Soc 1991; 16:523; 3) 1 Ahnfelt, L., P. Herberts, H. Malchau, and G. Andersson. Prognosis of total hip replacement: a swedish multicenter study of 4664 revisions. Acta Orthop. Scand. 61:2-26, 1990; 4) Corbett, K. L., E. Losina, A. A. Nti, J. J. Prokopetz, and J. N. Katz. Population-based rates of revision of primary total hip arthroplasty: a systematic review. PLoS ONE 5:e13520, 2010; 5) Huiskes, R. Failed innovation in total hip replacement: diagnosis and proposals for a cure. Acta Orthop. Scand. 64:699-716, 1993; 6) Harris, W. Aseptic loosening in total hip arthroplasty secondary to osteolysis induced by wear debris from titanium alloy modular femoral heads. JBJS. 73:470-472, 1991; 7) Kobayashi, S., K. Takaoka, N. Saito, and K. Hisa. Factors affecting aseptic failure of fixation after primary charnley total hip arthroplasty multivariate survival analysis. JBJS. 79:1618-1627, 1997; 8) Lombardi Jr, A. V., T. Mallory, B. Vaughn, and P. Drouillard. Aseptic loosening in total hip arthroplasty secondary to osteolysis induced by wear debris from titanium-alloy modular femoral heads. JBJS. 71:1337-1342, 1989; 9) Huiskes, R. Failed innovation in total hip replacement: diagnosis and proposals for a cure. Acta Orthop. Scand. 64:699-716, 1993; 10) Clohisy, J. C., G. Calvert, F. Tull, D. McDonald, and W. J. Maloney. Reasons for revision hip surgery: a retrospective review. Clin. Orthop. Relat. Res. 429:188-192, 2004; 11) Kim, Y. S., J. J. Callaghan, P. B. Ahn, and T. D. Brown. Fracture of the acetabulum during insertion of an oversized hemispherical component. JBJS. 77:111-117, 1995; 12) Sharkey, P. F., W. J. Hozack, J. J. Callaghan, Y. S. Kim, D. J. Berry, A. D. Hanssen, and D. G. LeWallen. Acetabular fracture associated with cementless acetabular component insertion: a report of 13 cases. J. Arthro-plast. 14:426-431, 1999; 13) Weeden, S. H. and W. G. Paprosky. Minimal 11-year follow-up of extensively porous-coated stems in femoral revision total hip arthroplasty. J. Arthroplast. 17:134-137, 2002; 14) Ulrich A D, Seyler T M, Bennett D, Celanois R E, Saleh K J, Thongtrangan I, Kuskowski M, Cheng E Y, Sharkey P F, Parvizi J, Stiehl J B, Mont M A. Total hip arthroplasties: What are the reasons for revision? International Orthopedics (SICOT) (2008) 32: 597-604; 15) Olory, B., E. Havet, A. Gabrion, J. Vernois, and P. Mertl. Comparative in vitro assessment of the primary stability of cementless press-fit acetabular cups. Acta Orthop. Belg. 70:31-37, 2004; 16) Meneghini, R. M., C. Meyer, C. A. Buckley, A. D. Hanssen, and D. G. Lewallen. Mechanical stability of novel highly porous metal acetabular components in revision total hip arthroplasty. J. Arthroplast. 25:337-341, 2010; 17) Fehring, K. A., J. R. Owen, A. A. Kurdin, J. S. Wayne, and W. A. Jiranek. Initial stability of press-fit acetabular components under rotational forces. J. Arthroplast 29:1038-1042, 2014; 18) Georgiou, A., and J. Cunningham. Accurate diagnosis of hip prosthesis loosening using a vibrational technique. Clin. Biomech. 16:315-323, 2001; 19) Balch C M, Freischlag J A, Shanafelt T, Stress and Burnout Among Surgeons. ARCH SURG/VOL 144 (NO. 4) April 2009; 20) Shanafelt T D, Balch C M, Bechamps G J, Tussell T, Dyrbye L, Satele D, Collicott P, Novotny P J, Sloan J, Freischlang J A Burnout and Career Satisfaction Among American Surgeons Ann Surg 2009; 250: 107-115; 21) Ulrich A D, Seyler T M, Bennett D, Celanois R E, Saleh K J, Thongtrangan I, Kuskowski M, Cheng E Y, Sharkey P F, Parvizi J, Stiehl J B, Mont M A. Total hip arthroplasties: What are the reasons for revision? International Orthopedics (SICOT) (2008) 32: 597-604; 22) Kurtz S, Ong K, Lau E, Mowat F, Halpern M, Projections of Primary and Revision Hip and Knee Arthroplasty in the United States from 2005 to 2030 JBJS (2007) Am 89: 780-785; 23) Nakasone S, Takao M, Nishii T, Sugano N, Incidence and Natural Course of Initial Polar Gaps in Birmingham Hip Resurfacing Cups. J of Arthroplasty Vol 27, (9) 1676-1682; and 24) Springer B D, Griffin W L, Fehring T K, Suarez J, Odum S, Thompson C Incomplete Seating of Press-Fit porous Coated Acetabular Components (2008) J of Arthroplasty Vol 23 (6) 121-126.

The system and methods above has been described in general terms as an aid to understanding details of preferred embodiments of the present invention. In the description herein, numerous specific details are provided, such as examples of components and/or methods, to provide a thorough understanding of embodiments of the present invention. Some features and benefits of the present invention are realized in such modes and are not required in every case. One skilled in the relevant art will recognize, however, that an embodiment of the invention can be practiced without one or more of the specific details, or with other apparatus, systems, assemblies, methods, components, materials, parts, and/or the like. In other instances, well-known structures, materials, or operations are not specifically shown or described in detail to avoid obscuring aspects of embodiments of the present invention.

Reference throughout this specification to "one embodiment", "an embodiment", or "a specific embodiment" means that a particular feature, structure, or characteristic described in connection with the embodiment is included in at least one embodiment of the present invention and not necessarily in all embodiments. Thus, respective appearances of the phrases "in one embodiment", "in an embodiment", or "in a specific embodiment" in various places throughout this specification are not necessarily referring to the same embodiment. Furthermore, the particular features, structures, or characteristics of any specific embodiment of the present invention may be combined in any suitable manner with one or more other embodiments. It is to be understood that other variations and modifications of the embodiments of the present invention described and illustrated herein are possible in light of the teachings herein and are to be considered as part of the spirit and scope of the present invention.

It will also be appreciated that one or more of the elements depicted in the drawings/figures can also be implemented in a more separated or integrated manner, or even removed or rendered as inoperable in certain cases, as is useful in accordance with a particular application.

Additionally, any signal arrows in the drawings/Figures should be considered only as exemplary, and not limiting, unless otherwise specifically noted. Combinations of components or steps will also be considered as being noted, where terminology is foreseen as rendering the ability to separate or combine is unclear.

The foregoing description of illustrated embodiments of the present invention, including what is described in the Abstract, is not intended to be exhaustive or to limit the invention to the precise forms disclosed herein. While specific embodiments of, and examples for, the invention are described herein for illustrative purposes only, various equivalent modifications are possible within the spirit and scope of the present invention, as those skilled in the relevant art will recognize and appreciate. As indicated, these modifications may be made to the present invention in light of the foregoing description of illustrated embodiments of the present invention and are to be included within the spirit and scope of the present invention.

Thus, while the present invention has been described herein with reference to particular embodiments thereof, a latitude of modification, various changes and substitutions are intended in the foregoing disclosures, and it will be appreciated that in some instances some features of embodiments of the invention will be employed without a corresponding use of other features without departing from the scope and spirit of the invention as set forth. Therefore, many modifications may be made to adapt a particular situation or material to the essential scope and spirit of the present invention. It is intended that the invention not be limited to the particular terms used in following claims and/or to the particular embodiment disclosed as the best mode contemplated for carrying out this invention, but that the invention will include any and all embodiments and equivalents falling within the scope of the appended claims. Thus, the scope of the invention is to be determined solely by the appended claims.

What is claimed as new and desired to be protected by Letters Patent of the United States is:

1. An acetabular cup for an installation into an irregularly-profiled cavity in a portion of bone, the installation having a desired orientation profile for the acetabular cup, comprising:
    an irregularly-profiled exterior shell portion defining a generally hemispherical interior cavity, said irregularly-profiled exterior shell portion configured to be complementary to the irregularly-profiled cavity;
    wherein said irregularly-profiled exterior shell portion is configured for a press fit fixation into the irregularly-profiled cavity; and
    wherein a composite of the irregularly-profiled cavity and said irregularly-profiled exterior shell cooperatively define a unique orientation key producing the desired orientation profile for the acetabular cup when installed into the irregularly-profiled cavity.

2. The acetabular cup of claim 1 wherein an outer surface of said irregularly-profiled exterior shell portion is configured to define a complementary irregular polygonal cross-section with an inner surface of the irregularly-profiled cavity.

3. The acetabular cup of claim 1 wherein an outer surface of said irregularly-profiled exterior shell portion is configured to define a complementary irregular non-polygonal cross-section with an inner surface of the irregularly-profiled cavity.

4. A kit for an installation of an implant into an irregularly-profiled cavity in a portion of bone, the kit including:
    a preoperatively-determined orientation for the implant;
    a body of the implant defining a body portion configured for fixation within the irregularly-profiled cavity, said body portion including a body keying structure; and
    a bone-preparation tool configured to produce the irregularly-profiled cavity in the portion of bone, the cavity having an interior wall surface defining a cavity portion configured for receiving said body portion, said cavity portion including a cavity keying structure complementary to said body keying structure;
    wherein a composite of said keying structures cooperatively produce said preoperatively-determined orientation by defining a unique key imparting said preoperatively-determined orientation when said body portion is fixated within said cavity portion.

5. The kit of claim 4 wherein the implant includes an acetabular cup.

6. The kit of claim 4 further comprising a premanufactured set of non-custom-manufactured implants and wherein the implant includes a particular implant from said set of non-custom-manufactured implants, said particular implant including said body keying structure.

7. The kit of claim 6 wherein the implant includes an acetabular cup.

8. The kit of claim 4 further comprising a post-preoperatively-determined-orientation-accessible additive manufacturing system configured to produce the implant, the implant including a custom body keying structure responsive to said preoperatively-determined orientation for the implant.

9. The kit of claim 8 wherein the implant includes an acetabular cup.

10. The kit of claim 4 wherein said cavity keying structure includes a predetermined cavity keying structure without customization of said cavity keying structure responsive to said preoperatively-determined orientation and wherein said bone preparation tool is operable to produce said predetermined cavity keying structure.

11. The kit of claim 10 wherein the implant includes an acetabular cup.

12. The kit of claim 4 wherein said cavity keying structure includes a custom cavity keying structure including a customization of said cavity keying structure responsive to said preoperatively-determined orientation and wherein said bone preparation tool is operable to produce said custom cavity keying structure.

13. The kit of claim 12 wherein the implant includes an acetabular cup.

\* \* \* \* \*